United States Patent
Dobson

(10) Patent No.: US 9,125,929 B2
(45) Date of Patent: Sep. 8, 2015

(54) TRAUMA THERAPY

(71) Applicant: Geoffrey Phillip Dobson, Wulguru (AU)

(72) Inventor: Geoffrey Phillip Dobson, Wulguru (AU)

(73) Assignee: Hibernation Therapeutics, A KF LLC, Camden, DE (US)

( * ) Notice: Subject to any disclaimer, the term of this patent is extended or adjusted under 35 U.S.C. 154(b) by 0 days.

(21) Appl. No.: 13/749,214

(22) Filed: Jan. 24, 2013

(65) Prior Publication Data

US 2013/0190264 A1 Jul. 25, 2013

Related U.S. Application Data

(63) Continuation of application No. 12/375,182, filed as application No. PCT/AU2007/001029 on Jul. 25, 2007, now abandoned.

(30) Foreign Application Priority Data

Jul. 25, 2006 (AU) ................................ 2006904007
Jan. 19, 2007 (AU) ................................ 2007900283

(51) Int. Cl.
*A61K 31/7076* (2006.01)
*A61K 31/167* (2006.01)
*A61K 45/06* (2006.01)

(52) U.S. Cl.
CPC ........... *A61K 31/7076* (2013.01); *A61K 31/167* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 4,798,824 A | 1/1989 | Belzer et al. |
| 5,006,512 A | 4/1991 | Ohnishi |
| 5,145,771 A | 9/1992 | Lemasters et al. |
| 5,206,222 A | 4/1993 | Forman et al. |
| 5,256,770 A | 10/1993 | Glaser et al. |
| 5,370,989 A | 12/1994 | Stern et al. |
| 5,407,793 A | 4/1995 | Del Nido et al. |
| 5,432,053 A | 7/1995 | Berdyaev et al. |
| 5,514,536 A | 5/1996 | Taylor |
| 5,656,420 A | 8/1997 | Chien |
| 5,679,706 A | 10/1997 | D'Alonzo et al. |
| 5,693,462 A | 12/1997 | Raymond |
| 6,011,017 A | 1/2000 | Marangos et al. |
| 6,187,756 B1 | 2/2001 | Lee et al. |
| 6,358,208 B1 | 3/2002 | Lang et al. |
| 6,372,723 B1 | 4/2002 | Martin et al. |
| 6,569,615 B1 | 5/2003 | Thatte et al. |
| 6,586,413 B2 | 7/2003 | Liang et al. |
| 6,921,633 B2 | 7/2005 | Baust et al. |
| 6,955,814 B1 | 10/2005 | Dobson |
| 6,992,075 B2 | 1/2006 | Hill et al. |
| 7,223,413 B2 | 5/2007 | Dobson |
| 7,749,522 B2 | 7/2010 | Dobson |
| 2001/0041688 A1 | 11/2001 | Waeber et al. |
| 2003/0216775 A1 | 11/2003 | Hill et al. |
| 2004/0229780 A1 | 11/2004 | Olivera |
| 2005/0176763 A1 | 8/2005 | Boy et al. |
| 2006/0034941 A1 | 2/2006 | Dobson |

FOREIGN PATENT DOCUMENTS

| | | |
|---|---|---|
| CN | 1176738 A | 3/1998 |
| CN | 1057192 | 10/2000 |
| CN | 101019529 | 8/2007 |
| DE | 39 26287 | 2/1991 |
| GB | 2 436 255 A | 9/2007 |
| JP | 09-151134 | 6/1997 |
| SU | 0878297 | 11/1981 |
| WO | WO-92/20346 A1 | 11/1992 |
| WO | WO-98/37886 | 9/1998 |
| WO | WO-00/03716 A1 | 1/2000 |
| WO | WO-00/24378 A1 | 5/2000 |
| WO | WO-00/56145 A1 | 9/2000 |
| WO | WO-01/54679 A2 | 8/2001 |
| WO | WO-01/82914 A2 | 11/2001 |
| WO | WO-03/063782 A2 | 8/2003 |
| WO | WO-03/088978 A1 | 10/2003 |
| WO | WO-04/000331 A1 | 12/2003 |
| WO | WO-2004/056180 A1 | 7/2004 |
| WO | WO-2004/056181 A1 | 7/2004 |
| WO | WO-2004/060286 A2 | 7/2004 |
| WO | WO-2004/108666 A2 | 12/2004 |
| WO | WO-2006/069170 A2 | 6/2006 |
| WO | WO-2007/030198 A2 | 3/2007 |
| WO | WO-2007/137321 A1 | 12/2007 |

(Continued)

OTHER PUBLICATIONS

Ar-Rajab, et al., "Improved Liver Preservation for Transplantation Due to Calcium Channel Blockade", *Transplantation*, 51(5):965-967, May 1991.

(Continued)

*Primary Examiner* — Sue Liu
*Assistant Examiner* — Luke Karpinski
(74) *Attorney, Agent, or Firm* — Venable LLP; Keith G. Haddaway; Miguel A. Lopez

(57) ABSTRACT

The invention provides a method of reducing injury to cells, tissues or organs of a body following trauma by administering a composition to the body following trauma, including: (i) a potassium channel opener or agonist and/or an adenosine receptor agonist and (ii) a local anaesthetic. Also provided is a composition for reducing injury to cells, tissues or organs of a body following trauma including: (i) and (ii). The composition may be hypertonic.

18 Claims, 19 Drawing Sheets

(56) References Cited

FOREIGN PATENT DOCUMENTS

| WO | WO-2008/011670 A1 | 1/2008 |
|---|---|---|
| WO | WO-2008/106724 A1 | 9/2008 |
| WO | WO-2009/012534 A1 | 1/2009 |

OTHER PUBLICATIONS

Beyersdorf, F., "The use of controlled reperfusion strategies in cardiac surgery to minimize ischaemia/reperfusion damage" *Cardiovascular Research*, 83, 262-268 (2009).

Brett, CL et al., "Evolutionary origins of eukaryotic sodium/proton exchangers" *Am J Physiol Cell Physiol*, 288, C223-C239 (2005).

Canyon, SJ, et al., "Protection Against Ventricular Arrhythmias and Cardiac Death Using Adenosine and Lidcaine During Regional Ischemia in the In Vivo Rat," *Am J. Physiol Heart Circ Physiol* 287:H1286-H1295; American Physiological Society 2004.

Canyon, SJ, et al., "Pretreatment with an Adenosine Al Receptor Agonist and Lidocaine: A Possible Alternative to Myocardial Ischemic Preconditioning," The Journal of Thoracic and Cardiovascular Surgery, vol. 130, No. 2, pp. 371-377, 2005.

Canyon, SJ, et al., "The Effect of Adenosine and Lidocaine Infusion on Myocardial High-Energy Phosphates and pH During Regional Ischemia in the Rat Model in vivo", Canadian Journal of Physiology and Pharmacology, vol. 84, 903-912, Oct. 18, 2006.

Chien, S, et al., "Extension of Tissue Survival Time in Multiorgan Block Preparation With a Delta Opioid DADLE (D-Ala2, D-Leu5)-enkephalin)," The Journal of Thoracic and Cardiovascular Surgery, 107:965967, 1994.

Corvera, JS, et al., "Polarised Arrest With Warm or Cold Adenosine/Lidocaine Blood Cardioplegia is Equivalent to Hypothermic Potassium Blood Cardioplegia," *The Journal of Thoracic and Cardiovascular Surgery*, 129(3):599-606, May 2005.

Das, et al., "Myocardial preservation during cardiac surgery", *Annals of Cardiac Anaesthesia*, vol. 5, pp. 25-32, 2002.

Dobson, G.P., "Organ Arrest, Protection and Preservation: Natural Hibernation to Cardiac Surgery," Comparative Biochemistry and Physiology, 139 (Part B):469-485; Elsevier Inc., 2004.

Dobson, G.P., et al., "Adenosine and Lidocaine: A New Concept in Nondepolarizing Surgical Myocardial Arrest, Protection and Preservation," The Journal of Thoracic and Cardiovascular Surgery 127:794-805, Mar. 2004.

Ely, S.W., et al., "Protective Effects of Adenosine in Myocardial Ischemia", Circulation, 85(3): 893-904, Mar. 1992.

Forman, et al., "Mechanisms and Therapy of Myocardial Reperfusion Injury". Circulation, 81(3 Suppl):IV69-78, Mar. 1990.

Forman, et al., "Adenosine Therapy at Reperfusion on Myocardial Infarct Size," Cardiovascular Research, 33:497-498, 1997.

Garratt, et al., "Intravenous Adenosine and Lidocaine in Patients with Acute Myocardial Infarction," American Heart Journal, 136(2): 196-204, Aug. 1998.

Goto, et al., "Adenosine Infusion During Early Reperfusion Failed to Limit Myocardial Infarct Size in a Collateral Deficient Species" Cardiovascular Research, 25(11):943-9, Nov. 1991.

Granger, C.B., "Adenosine for Myocardial Protection in Acute Myocardial Infarction", The American Journal of Cardiology, 79(12A): 44-48, Jun. 1997.

Hearse, et al., "Protection of the Myocardium during ischemic arrest," J. Thorac. Cardiovasc. Surg., vol. 81, No. 6, pp. 873-879, 1981.

Hicks, et al., "ATP-Sensitive Potassium Channel Activiation Mimics the Protective Effect of Ischaemic Preconditioning in the Rat Isolated Working Heart After Prolonged Hypothermic Storage," Clinical and Experimental Pharmacology and Physiology 26:20-25, 1999.

Homeister, et al., "Combined Adenosine and Lidocaine Administration Limits Myocardial Reperfusion Injury," Circulation, 82(2):595-608, Aug. 1990.

Huang, T.F., "Drug Effects on the Ischemia- and Reperfusion-induced Arrhythmias in the Conscious Rats", Chinese Journal of Physiology 35(1): 9-19,1992.

International Preliminary Examination Report, dated Mar. 5, 2001, issued in related International Application No. PCT/AU00/00226.

International Preliminary Examination Report, dated Oct. 12, 2004, issued in related International Application No. PCT/AU2003/000771.

International Preliminary Report on Patentability, dated Dec. 3, 2008, issued in related Internatibnal Application No. PCT/AU2006/000717.

International Preliminary Report on Patentability, dated Jan. 27, 2009, issued in related International Application No. PCT/AU2007/001029.

International Preliminary Report on Patentability, dated Sep. 8, 2009, issued in related International Application No. PCT/AU2008/000289.

International Preliminary Report on Patentability, dated Jan. 26, 2010, issued in related International Application No. PCT/AU2008/001086.

International Search Report dated Jun. 9, 2000, issued in related International Application No. PCT/AU00/00226.

International Search Report dated Aug. 4, 2003, issued in related International Application No. PCT/AU03/00771.

International Search Report dated Feb. 13, 2004, issued in related International Application No. PCT/AU2003/001710.

International Search Report dated Feb. 13, 2004, issued in related International Application No. PCT/AU2003/001711.

International Search Report dated Jul. 21, 2006, issued in related International Application No. PCT/AU2006/000717.

International Status Report, Dated Sep. 25, 2007, issued in related International Application No. PCT/AU2007/001029.

International Search Report, dated May 7, 2008, issued in related International Application No. PCT/AU2008/000289.

International Search Report dated Sep. 25, 2008, issued in related International Application No. PCT/AU2008/001086.

Jakosben, et al., "Adenosine instead of supranormal potassium in cardioplegic solution improves cardioprotection," *European Journal of Cardio-thoracic Surgery*, vol. 32, pp. 493-500, 2007.

Jakosben, et al., "Adenosine instead of supranormal potassium in cardioplegic solution preserves endothelium-derived hyperpolarization factor-dependent vasodilation", *European Journal of Cardio-thoracic Surgery*, vol. 33, pp. 18-24, 2008.

Jayawant, et al., "Advantages of Continuous Hyperpolarized Arrest with Pinacidil Over St. Thomas' Hospital Solution During Prolonged Ischemia," *J. Thoracic and Cardiovascular Surgery*, 11(1): 131-138, 1998.

Jayawant, AM et al "Potassium-channel opener cardioplegia is superior to St. Thomas' solution in the intact animal" Ann Thorac Surg, 68, 67-74 (1999).

Jin, et al, "The myocardial protective effects of a moderate-potassium adenosine-lidocaine cardioplegia in pediatric cardiac surgery", The Journal of Thoracic and Cardiovascular Surgery, vol. 136, No. 6, pp. 1450-1455, 2008.

Karck, M., et al, "Myocardial protection by ischemic preconditioning and -opioid receptor activiation in the isolated working rat heart" The Journal of Thoracic and Cardiovascular Surgery, 122, 986-992 (2001).

Kinoshita, H., et al "Mild alkalinisation and acidification deifferentially modify the effects of lidocaine or mexiletine on vasorelaxation mediated by ATP-sensitive K+ channels" Anesthesiology, 95, 200-206 (2001).

Kusano T. et al., "Organ Preserving Effect of lidocaine Administration in the Model of Orthopic Liver Transplantation from Non-heart Beating Donors", Transplantation Proceedings, 28(3): 1928-1929, Jun. 1996.

Lee et al., "Retrograde infusion of liocaine or L-arginine before reperfusion reduces myocardial infarct size", Ann. Thorac. Surg 65:1353-1359, 1998.

Mahaffey, et al., "Adenosine as an Adjunct to Thrombolytic Therapy for Acute Myocardial Infarction," JACC 34(6): 1711-20, Nov. 1999.

Neely, et al., "A1 Adenosine Receptor Antagonist Block Ischemia-reperfusion Injury of the Heart", Circulation, Supplement 94(9):11376-11380, 1996, abstract.

O'Rullian, et al., "Excellent Outcomes in a Case of complex Re-do Surgery Requiring Prolonged Cardioplegia Using a New

(56) References Cited

OTHER PUBLICATIONS

Cardioprotective Approach: Adenocaine," *The Journal of ExtraCorporeal Technology,* vol. 40, pp. 203-205, 2008.

Rogriguez-Reynoso, et al "Effect of exogenous melatonin on hepatic energetic status during ischemia/reperfusion: possible role of tumor necrosis factor-a and nitric oxide" *J Surgical Research,* 100(2), 141-149 (2001).

Rudd, DM, et al. "Toward a New Cold and Warm Nondepolarizing, Normokalemic Arrest Paradigm for Orthotopic Heart Transplantation", Journal of Thoracic and Cardiovascular Surgery, 137(1): 198-207, Jan. 2009.

Schubert, et al., "Adenosine cardioplegia," J. Thorac. Cardiovasc. Surg., vol. 98, No. 6, pp. 1057-1065, 1989.

Segal, et al., "On the Natriuretic Effect of Verapamil: Inhibition of EnaC and Transephithelial Sodium Transport", Am J. Physiol Renal Physiol, 283: F765-F770, 2002.

Sigg, et al "Role of d-opioid receptor agonists on infarct size reduction in swine" Am. J. Physiol. Heart Circ. Physiol, 282, H1953-H1960 (2002).

Silber, et al "A rapid hemodynamic monitor of acute ischemia during cardiac procedures: changes in relaxation via a continuous left ventricular pressure-derivative loop" J Surg Res, 134(1), 107-113 (2006) with Medline entry Acc No. 2006367738.

Sloots, K, et al, "Warm nondepolarizing adenosine and lidocaine cardioplegia: Continuous versus intermittent delivery," The Journal of Thoracic and Cardiovascular Surgery, vol. 133, No. 5, pp. 1171-1178. 2007.

Su, T-P., "Delta Opioid Peptide [D-Ala2, D-Leu5] Enkephalin Promotes Cell Survival," J. Biomed. Sci., 7:195-199, 2000.

Sultan, et al., "Heart Preservation: Analysis of Cardioprotective Infusate Characteristics, Membrane Stabilization, Calcium Antagonism, and Protease Inhibition on Myocardial Viability: A Biochemical, Ultrastructural, Functional Study," The Journal of Heart and Lung Transplantation 11(4):607-18, 1992.

Takeuchi, et al. "Prolonged Preservation of the Blood-Perfused Canine Heart with Glycolysis-Promoting Solution," Ann Thorac Surgery 68:903-7, 1999.

Ulusal, et al., "The Effect of A2a Adenosine Receptor Agonist on Composite Tissue Allotransplant Survival: An In Vitro Preliminary Study", J. Surgical Research 131: 261-266, 2006.

Vander Heide, et al., "Adenosine Therapy at Reperfusion and Myocardial Infarct Size," Cardiovascular Research, 33:499-500, 1997.

Vinten-Johansen, J., et al. "Preconditioning and postconditioning: innate cardioprotection from ischemia-reperfusion injury." Journal of Applied Physiology, 103(4). pp. 1441-1448, 2007.

Wu, et al., "Mechanism of cardiac protection by preconditioning and postconditioning for hypoxia-reoxygenation injury is different" Jpn J Physiol, 54, S96, item 127 (2004).

Dobson GP, Membrane polarity: A target for myocardial protection and reduced inflammation in adult and pediatric cardiothoracic surgery, The Journal of Thoracic and Cardiovascular Surgery, vol. 140, No. 6, pp. 1213-1217, 2010.

Dobson, Geoffrey, "Bloody Battle" Australian Science, pp. 14-16, 2011.

Rudd et al., Early reperfusion with warm, polarizing adenosine-lidocaine cardioplegia improves functional recovery after 6 hours of cold static storage, The Journal of Thoracic and Cardiovascular Surgery, vol. 141, No. 4, pp. 1044-1055, 2011.

Thourani et al., "Myocardial Protection with Adenosine Given at Reperfusion is Superior to Adenosine-Enhanced Cardioplegia," Insulin Cardioplegia for Coronary Bypass Surgery, Supplement I, 3217, pp. 1-2.

Thourani et al., "Adenosine-Supplemented Blood Cardioplegia Attenuates Postischemic Dysfunction After Severe Regional Ischemia," Circulation, 1999, pp. II-376-II-383.

Gao et al., "Cardioprotective Effects of Melatonin on Recovery of Rat Donor Hearts after 12-Hour Preservation," Journal of Huazhong University of Science and Technology [Med Sci], 2003, pp. 407-410, vol. 23 (4), Wuhan.

TRAUMA THERAPY

FIELD OF THE INVENTION

This invention relates to a method of reducing injury to cells, tissues or organs of a body following trauma, including injury to cells, tissues or organs resulting from shock, stroke, heart conditions or other injuries that may occur as a consequence of trauma.

BACKGROUND OF THE INVENTION

In the western world, many deaths occur suddenly and unexpectedly, particularly as a consequence of trauma. Medically, "trauma" refers to a serious or critical bodily injury, wound, or shock which in some cases may require resuscitation therapy. Trauma is often associated with trauma medicine practiced in hospital (such as in hospital emergency rooms), in emergency transport environments (such as in ambulances), or at out-of-hospital environments where a trauma has occurred, such as domestic or industrial accidents, transport accidents, the battlefield, and terrorist attacks.

Trauma is a leading cause of death among children and all individuals to age 34 years and a major cause of death in the older population resulting in loss of productive life-years with substantial societal costs. This includes deaths resulting from burns, heart attacks, strokes and other cardiovascular events. Deaths can also result from shock or other complications that may occur as a consequence of trauma.

Less than 3% of these unconscious trauma patients will advance to acceptable outcomes. Many survivors require institutional care after 3 months and a significant proportion remain permanently disabled. About 20% of soldiers injured in the battlefield will die, and 90% of deaths occur before reaching a hospital because of shock during emergency transport. More recent statistics suggest that 50% of deaths in potentially treatable combat injuries are due to acute blood loss, making it the leading cause of death on the battlefield.

Shock is a circulatory dysfunction causing decreased tissue oxygenation and accumulation of oxygen debt, which can ultimately lead to multi-organ system failure if left untreated. The most common form of shock in both paediatric and adult trauma patients is hemorrhagic or hypovolemic shock (not enough blood volume). Cardiogenic shock (not enough output of blood by the heart, see below) is also a common form of shock. Shock as a result of blood loss is a frequent complication of trauma. About half of trauma deaths occur during the first hour after injury from a profound compromise in cardiopulmonary and cerebral function. The signs and symptoms of shock include low blood pressure (hypotension), overbreathing (hyperventilation), a weak rapid pulse, cold clammy greyish-bluish (cyanotic) skin, decreased urine flow (oliguria), and mental changes (a sense of great anxiety and foreboding, confusion and, sometimes, combativeness). When blood is lost, the greatest immediate need is replacing the lost volume with blood or blood volume expanders. Provided blood volume is maintained by volume expanders, a trauma patient can safely tolerate very low blood haemoglobin levels, less than one third of a healthy person.

During trauma, the electrical properties of vital organs and tissues cannot be maintained. Falls in resting cell voltage occur during trauma and can lead to the triggering of highly injurious arrhythmias in the heart and activation of systemic inflammatory, coagulative and free radical generating processes that can lead to multiple organ failure and death. During severe haemorrhage, patients become unconscious when the mean arterial perfusion pressure decreases to about 40 mm Hg and the pulse is no longer palpable in the large arteries. When breathing stops and pulsations are no longer palpable, cardiac arrest is assumed. The mortality rate for trauma patients who become pulseless from massive blood loss and undergo emergency department thoracotomy is around 97%.

One form of shock is called "cardiogenic shock". This may be caused by the failure of the heart to pump effectively due to, for example, damage to the heart muscle (as may result from a large myocardial infarction (heart-attack), disorders of the heart muscle (including rupture), disturbances to the electrical excitation-relaxation (or conduction) system and tamponade. Cardiogenic shock may also be caused by arrhythmias (eg ventricular tachycardia and ventricular fibrillation), cardiomyopathy, cardiac valve problems, ventricular outflow obstruction and the like. Cardiogenic shock is a medical emergency requiring immediate treatment to save the patient's life.

One cause of cardiogenic shock is a so-called "heart-attack". This term is used to refer to a number of different conditions which lead to heart ischaemia, which leads to the death of heart muscle (typically caused by blockage of a coronary artery). The muscle death causes chest pain and electrical instability of the heart muscle tissue. This electrical instability may manifest as "ventricular tachycardia" and "ventricular fibrillation". Ventricular tachycardia is a tachydysrhythmia originating from a ventricular ectopic focus and characterized by a rate typically greater than 120 beats per minute and must be treated quickly to avoid morbidity or mortality as it may deteriorate rapidly into ventricular fibrillation. Ventricular fibrillation is a condition in which there is chaotic electrical disturbances of the ventricles, such that they no longer beat regularly, nor pump blood effectively, but simply quiver. During ventricular fibrillation the heart muscle is affected by a poor supply of oxygen or by specific heart disorders and the ventricles contract independently of the atria, and some areas of the ventricles contract while others are relaxing, in a disorganized manner. Ventricular fibrillation leads to widespread ischaemia. Unless treated immediately, ventricular fibrillation causes death and is responsible for 75% to 85% of sudden deaths in persons with heart problems. In the USA alone there are nearly 450,000 sudden deaths per year, and in the united kingdom around 70,000-90,000 sudden deaths per year. Ventricular tachycardia and ventricular fibrillation are therefore medical emergencies because if they persist more than a few seconds, the blood circulation will cease, there will be no pulse, no blood pressure and no respiration and death will occur. Typically, medications and procedures at this time are directed towards stabilising the rhythm of the heart and, in the case of the unconscious subject with no measurable pulse, resuscitating the subject by restarting the heart, opening the airways and restoring spontaneous breathing. Amiodarone can be used to treat life-threatening heart arrhythmias, however, the drug can have serious side effects including causing cardiac rhythm irregularities and cardiac arrest itself. Other side effects of amiodarone include lung infiltration, neuropathy, tremors, thyroid disorders, nausea, low blood pressure and liver damage. Effective medications for stabilizing the heart or restarting the heart and restoring the spontaneous circulation in these emergency situations are therefore very limited or non-existent. Noradrenalin or adrenalin (with or without vasopressin) can be used in conjunction with cardiopulmonary resuscitation, however, epinephrine can exacerbate heart contractions and promote heart dysfunction by increasing myocardial oxygen consumption during ventricular fibrillation, as well as eliciting microvascular disorders. If the treatments are successful in stabilising the heart after ventricular tachycardia or ventricular fibrillation, a number of medications are then administered such as oxygen (if available to help breathing), beta-blockers (to help relax the heart), vasodilators (to help deliver more blood to the heart), blood agents (anti-coagulants, anti-platelet agents, thrombolytics and the like) and pain relievers. Apart from a few drugs to treat the heart as well as other tissues and organs, the medications are not directed to treating the cardiac tissue specifically. There is no effective pharmaceutical treatment for the failing heart muscle itself, nor for common ventricular fibrillation. If treated, this is usually treated by electrical shock (cardioversion).

Damage may also be caused to a heart upon reperfusion. One example of reperfusion damage is when a heart becomes "stunned". In this condition, the bloodflow has been restored but the heart is functioning abnormally and may result in a further heart-attack (such as ventricular fibrillation) if not treated. Cardiac reanimation inevitably involves reperfusion of the heart with the consequent dangers associated with reperfusion injury, particularly to heart muscle. Where the muscle cells die, this is regarded as an infarction. If blood flow is restored to the cells within a short period of about 15 to 20 minutes the cells may respond to the reperfusion and survive (thus not forming an infarction) but may be "stunned" in the sense that they do not operate normally nor perform their usual function during reperfusion.

In patients who survive resuscitation where the initial event may be less traumatic, they remain at a significant risk from systemic and local inflammatory and immune activation followed by multiple organ dysfunction and failure. Multiple organ failure is believed to be the result of an excessive self-destructive systemic inflammation and immunologic functions, in which hypoxemia, tissue hypoxia/nonviable tissue, micro-organisms/toxins and antigen/antibody complexes may be involved. In particular, the activation of a number of humoral (e.g. complement, coagulation) and cellular systems (endothelium activation, neutrophils, platelets, macrophages) are believed to be involved. Neutrophils play a key role in injury to the lung, heart, kidney, liver, and gastrointestinal tract, often seen after major trauma. As a consequence there is synthesis, expression and release of numerous mediators (toxic oxygen species, proteolytic enzymes, adherence molecules, cytokines), which may produce a generalized inflammation and tissue damage in the body.

The critical core body temperature also can aggravate many of these post-traumatic secondary complications. Below 34° C. mortality increases significantly. Despite this, a number of investigators have suggested a beneficial effect of deliberate hypothermia because this may prolong the "golden hour" of trauma victims by preventing hypoxic organ dysfunction and initiation of the inflammatory response. Organ failure is also the leading cause of death in the postoperative phase after major surgery. An excessive inflammatory response followed by a dramatic depression of cell-mediated immunity after major surgery appears to be responsible for the increased susceptibility to subsequent sepsis.

Resuscitation therapy is generally regarded as any procedure which improves the management of sudden states of life-threatening illnesses or traumatic injuries, such as those from cardiac arrest, respiratory failure, hemorrhagic blood loss, neurological injury, and traumatic injuries to the soft tissues and body skeleton. Generally, resuscitation therapy deals with treating whole body oxygen deprivation. As such, current resuscitation strategies aim to optimize tissue supply and demand ratio and avoid complications of overaggressive volume replacement, which exacerbate haemorrhage, pulmonary oedema, and intracranial hypertension following brain injury.

Resuscitation therapy is very different from treating a localized "big heart attack" or a localized "big stroke". It involves a complex interplay between multiple organ-tissue responses via poorly understood actions, which separates this science from treatments to preserve particular organs or tissues. Resuscitation is known to involve a complex biological system, with many interactions. These cannot be predicted from study of individual components. Injured organs have secondary effects on other organs, which affects the whole body and can lead to debilitating injuries and death.

Current therapies involve fluid or volume replacement that can either be crystalloid or colloidal. Crystalloids are commonly used for resuscitation therapy because they appear to be safe and help with the negative side effects of coagulation. Crystalloids have been shown to increase coagulation, an effect which seems to be independent of the type of crystalloid used. A crystalloid-induced hypercoagulable state appears to be due to an imbalance between naturally occurring anticoagulants and activated procoagulants. Crystalloids used for volume replacement can be three main types: 1) hypotonic (eg. dextrose in water), 2) isotonic (normal saline or Ringers solution with lactate or acetate) or 3) hypertonic (eg 7.5% saline). Since crystalloids are freely permeable to the vascular membrane, only about 25% remain in the blood compartment and the remainder in the body's interstitial and/or intercellular compartment leading to tissue oedema. Crystalloid resuscitation is therefore less likely to achieve adequate restoration of microcirculatory blood flow compared to a colloidal-based volume replacement strategy.

Colloid replacement therapies employ colloids, such as dextran-70, dextran-40, hydroxyethyl starch, pentastarch, lactobionate, sucrose, mannitol and a modified fluid gelatine as artificial colloids, for this purpose. There is much controversy as to the most appropriate solution for volume replacement.

Currently there is no optimal fluid composition or fluid resuscitation regimen to treat severe hemorrhagic shock in soldiers on the battlefield or civilians at a natural disaster site or injured from a terrorist attack. Indeed, the majority of approved resuscitation fluids have no intrinsic tissue protection and can trigger life-threatening inflammatory and hypercoagulable imbalances that negatively impact on the resuscitative outcome. A further challenge in designing new drug products and resuscitation therapies, in particular for the military, is hampered by logistical considerations imposed by the combat conditions themselves such as weight and practicability to transport, ease of deployment, administration in low-light environments and stability of drugs in the field, notwithstanding ensuring their safety and clinical effectiveness to increase the survival times of wounded soldiers after prolonged evacuation.

In warfare, bullets and penetrating fragments from exploding munitions frequently cause life-threatening hemorrhage. Acute hemorrhage is the leading cause of mortality in battlefield injuries and responsible for 50% of deaths in potentially treatable combat casualties. One major unmet medical need on the battlefield is how to prevent cardiac destabilization and arrest during severe hemorrhage before control of bleeding is possible. Stabilizing heart and circulatory deficiencies before shock is of paramount importance. Successful treatment of cardiac arrest requires an electrically stable and mechanically viable heart to be re-established. Currently there is no clinically effective method of stabilizing and protecting the heart from fibrillating and arresting before hemorrhagic shock.

Indeed, many pharmacological interventions employed to convert the heart to sinus rhythm may unfortunately inflict additional injury and compromise cardiac resuscitability In those severe traumatic hemorrhagic cases where the heart does not destabilize and arrest, the loss of blood volume, blood pressure and organ perfusion can lead to severe organ ischemia and eventually multiple organ dysfunction and failure (MOF) and death. MOF is the leading cause of mortality secondary to shock (hemorrhage/trauma) and resuscitation, and involves the lungs, kidneys, intestinal tract, pancreas, liver, brain and heart. Importantly, MOF is not an end-point per se but a process involving an overwhelming self-destructive, local and systemic, inflammatory responses and immunologic functions. Despite decades of research, resuscitation fluids restore tissue perfusion, however they have no specific anti-inflammatory, immunosuppression or pro-survival properties. Importantly, the activation of shock-induced inflammatory response occurs during the shock itself, during early crystalloid or colloid-based resuscitation therapy, and during final resuscitation efforts with blood replacement.

It is not known whether protection from injury from trauma could be elicited by a form of artificial hibernation. Natural hibernators possess the ability to lower their metabolic energy demand for days to months. Hibernation, like sleep, is a form of dormancy and helps to keep the animal's metabolic supply and demand ratio in balance. Remarkably, no damage occurs during these prolonged "ischemic" states, nor does the cardiac rhythm deteriorate into ventricular fibrillation. However, there is no known method of stimulating a similar response in humans, particularly trauma patients, despite the potential for substantial saving of life or minimising injury.

WO00/56145, WO04/056180 and WO04/056181 describe compositions useful to limit damage to a cell, tissue or organ by administering them in a clinical setting prior to a medical procedure. These compositions are also usually administered following diagnosis of the patient and directly to the cell, tissue or organ. However, much damage or injury to cells, tissues or organs may arise before the patient gets to the hospital and/or at hospital, for example, before substantive medical attention is available or a condition can be diagnosed.

SUMMARY OF THE INVENTION

The present invention is directed toward overcoming or at least alleviating one or more of the difficulties and deficiencies of the prior art.

In one aspect the invention is directed to a method of reducing injury to cells, tissues or organs of a body following trauma by administering a composition to the body following trauma, including: (i) a potassium channel opener or agonist and/or an adenosine receptor agonist; and (ii) a local anaesthetic.

According to this aspect, a further composition comprising components (i) and (ii) may be administered to the body following administration of the composition.

Either composition may include Magnesium cations (divalent) and/or may be hypertonic.

In another aspect the invention is directed to a composition for reducing injury to cells, tissues or organs of a body following trauma including: (i) a potassium channel opener or agonist and/or an adenosine receptor agonist; and (ii) a local anaesthetic. In one embodiment of this aspect, the composition may include divalent magnesium cations and/or may be hypertonic.

DETAILED DESCRIPTION OF THE INVENTION

The invention is directed to improved resuscitation therapies for trauma victims in hospital, emergency transport and out-of-hospital environments. In particular, the invention has application to minimise life-threatening complications of persons suffering injury to cells, tissues or organs resulting from burns, shock, stroke, heart attack or other physical events, including complications from surgical or clinical interventions, as a consequence of trauma. Injured soldiers on the battlefield or civilians at a natural disaster site or injured from a terrorist attack are situations where such treatment may be useful.

The invention applies to protecting, preserving or stabilising key organs such as the heart and brain, other neuronal tissues and cells, renal tissue, lung tissue, muscle tissue, liver and other tissues of the body.

In one form, the invention provides a method of reducing injury to the cells, tissues or organs of a body following trauma by administering a composition to the body following trauma including: (i) a potassium channel opener or agonist and/or an adenosine receptor agonist; and (ii) a local anaesthetic.

In another form of the invention, the invention is directed towards treating tachycardia and/or fibrillation. In one form, the invention treats heart arrhythmias of atrial or ventricular origin, especially ventricular fibrillation. The treatment of tachycardia and/or fibrillation, including ventricular fibrillation and arrhythmias, comprises administering a composition including: (i) a potassium channel opener or agonist and/or an adenosine receptor agonist; and (ii) a local anaesthetic, in amounts effective to arrest a heart. In one embodiment, the amount administered is effective to arrest the heart only momentarily. This is often sufficient to facilitate the heart cardioconverting back to normal rhythm. In an alternate embodiment, the amount administered is effective to substantially down-regulate the beating of the heart for a period of a few beats, before allowing the heart to regain its usual rhythm. The invention also extends to a method for treating tachycardia and/or fibrillation accordingly. Preferably, the composition is administered as a bolus. The administration of the composition is believed to quell the tachycardia and/or fibrillation allowing the heart to cardiovert to a normal and desirable sinus rhythm.

In a preferred embodiment, the invention comprises the further step of subsequently administering a second composition which includes (i) a potassium channel opener or agonist and/or an adenosine receptor agonist; and (ii) a local anaesthetic, in amounts below that effective to arrest a heart. The purpose of the second composition is to protect the heart and other tissues such as brain, liver, lung and kidney, or assist in doing so. In particular, this embodiment is directed towards reducing reperfusion injury or stunning. As outlined above, reperfusion injury is a common deleterious occurrence upon successfully converting a tachycardic/fibrillating heart to a normal and desirable sinus rhythm. In a preferred embodiment, the second composition is administered as another non-arresting bolus injection or delivered continuously via an intravenous drip or by another delivery device or route.

Without being bound by any theory or mode of action, the inventor has found that the composition according to the invention can be used to place the body, in effect, toward a state of suspended animation like a natural hibernator or to stabilise the body prior to diagnosis or until suitable medical attention can be provided to the trauma victim. The overall protection provided by therapy according to the invention is thought to involve a multi-tiered system from modulating membrane excitability to a multitude of intracellular signalling pathways, including heat shock and pro-survival kinase pathways. A primary focus is on reducing damage to the brain, heart and lungs, because this has been correlated with improved recovery and clinical outcomes. Nonetheless, broad-acting approaches reducing damage throughout the body in a non-specific way are desirable. Proposed mechanisms of the composition of the invention include (i) reduced ion imbalances, in particular sodium and calcium ion loading in the cells, which may help defend the cell's voltage when stressed; (ii) attenuation of local and systemic inflammatory response to injury, which is protective in itself to reduce injury as well as reduce secondary effects such as free radical production; and (iii) protection from entering into a hypercoagulable state, ie an anti-clotting or anti-thrombolytic activity. Moreover, it is believed that, in respect of the heart, the invention simultaneously provides improved atrial and ventricular matching of electrical conduction to metabolic demand, which may involve modulation of gap junction communication, and, in respect of the brain, improved brain function. It is also believed that the composition may reduce the body's demand for oxygen to varying degrees and thus reduce damage to the body's cells, tissues or organs. In another form, the invention provides a composition for reducing injury to cells, tissues or organs of a body following trauma including (i) a potassium channel opener or agonist and/or an adenosine receptor agonist; and (ii) a local anaesthetic. The composition may further include other components as identified below. In some embodiments, the potassium channel opener or agonist and/or adenosine receptor agonist is replaced by another component such as a calcium channel blocker. The composition preferably contains an effective amount of (i) and (ii) for a single dose to reduce injury.

More surprisingly, it has been observed that administration of a composition with arresting or near-arresting concentrations of components (i) and (ii) to a subject experiencing ventricular fibrillation assists the heart to regain normal sinus rhythm without the requirement for electrical shock treatment.

The invention may also be used to treat or inhibit arrhythmias including ventricular fibrillation during or prior to an angiogram test or an exercise test. Similarly it has application during emergency transport of an injured patient and for on-site emergency treatment (ie, at the site of injury or heart-attack such as an airport, sports stadium, hospital, battlefield or disaster site). It can also be used before, during and/or after coronary interventions such as angioplasty, cardiac catheter procedures, or insertion of a pacemaker or leads or a device, or for surgical procedures including paediatric or adult heart surgery, hip, knee, vascular or brain surgery, aortic dissections, carotid endaterectomy or general surgery.

In the embodiments of the invention described above and below, component (i) of the composition may be an adenosine receptor agonist. While this obviously includes adenosine itself, the "adenosine receptor agonist" may be replaced or supplemented by a compound that has the effect of raising endogenous adenosine levels. This may be particularly desirable where the compound raises endogenous adenosine levels in a local environment within a body. The effect of raising endogenous adenosine may be achieved by a compound that inhibits cellular transport of adenosine and therefore removal from circulation or otherwise slows its metabolism and effectively extends its half-life (for example, dipyridamole) and/or a compound that stimulates endogenous adenosine production such as purine nucleoside analogue Acadesine™ or AICA-riboside (5-amino-4-imidazole carboxamide ribonucleoside). Acadesine is also a competitive inhibitor of adenosine deaminase (Ki=362 microMolar in calf intestinal mucosa.) Acadesine™ is desirably administered to produce a plasma concentration of around 50 microM (uM) but may range from 1 microM to 1 mM or more preferably from 20 to 200 uM. Acadesine™ has shown to be safe in humans from doses given orally and/or intravenous administration at 10, 25, 50, and 100 mg/kg body weight doses.

In one form of the invention, the composition, and optionally the second composition, also contains divalent magnesium cations. In one embodiment, the concentration of magnesium is up to about 2.5 mM and in another embodiment magnesium is present in higher concentrations, for example up to about 20 mM. The magnesium is present as a physiologically and pharmaceutically acceptable salt, such as for example magnesium chloride and magnesium sulphate.

In another form the composition according to the invention is hypertonic. Preferably the composition contains 7.5% NaCl. The inventor has found that only a small volume of this hypertonic composition may be administered to the subject in need thereof. This is particularly advantageous where the composition according to the invention has application during emergency or for emergency transport. According to this aspect, only a small amount of the composition according to the invention needs to be available, for example, in a medical kit or ambulance. Thus the composition is easier to store and/or transport. This "low volume" composition has unique features of fluid replacement and specific anti-inflammatory, immunosuppression pro-survival properties. The composition according to this aspect of the invention pharmacologically "buys" time for wounded soldiers on the battlefield or civilians in urban "disaster zones" which allow for safer evacuation, triage, and initiation of supportive therapies. The ability of a solution to change the shape or tone of cells by altering their internal water volume is called tonicity (tono=tension). A Hypertonic solution contains a higher concentration of electrolytes than that found in body cells and, therefore, relatively less water in this compartment than inside the body cells. In such a hypertonic environment, osmotic pressure causes water to flow out of the cell into the hypertonic environment. Thus a hypertonic solution creates a hyperosmotic environment and the higher osmotic pressure in this environment relative to the surrounding cells in tissues causes fluid to flow from the cells towards such a system. If too much water is removed in this way, the cell may have difficulty functioning.

The invention described in this specification largely relates to methods of treatment, and methods of manufacturing a medicament for treatment involving a composition which is described as containing these components (i) and (ii). For convenience, this composition will be referred to in this specification as the "composition of the invention", although there are a number of combinations of components embodying the invention which are compositions according to the invention. Moreover, as explained particularly in WO00/56145, the components (i) and (ii) may be present in a concentration which arrests, or does not arrest a heart. These two compositions are used in different ways in the invention described in the specification, and are referred to respectively as an "arresting" concentration of the composition and a "non-arresting" concentration of the composition. In one form, the arresting composition contains adenosine and lignocaine, each at greater than 0.1 mM (and preferably below 20 mM). The arresting composition may in some circumstances be referred to as a "cardioplegia solution". In one form of the non-arresting composition, adenosine and lignocaine are both below 0.1 mM and preferably 50 nM to 95 uM, or more preferably from 1 uM to 90 uM.

In a further form, the invention provides use of (i) a potassium channel opener or agonist and/or an adenosine receptor agonist; and (ii) a local anaesthetic, for the preparation of a medicament for reducing injury to cells, tissues or organs of a body following trauma. The use preferably includes administering the medicament in one or more of the ways set out elsewhere in this specification.

In another form, the invention provides a method of, in effect, placing the body in or toward a hibernating-like state of suspended animation following trauma. This is achieved by administering a composition as described above.

The term "trauma" is used herein in its broadest sense and refers to a serious or critical injury, wound or shock to the body. Trauma may be caused by unexpected physical damage (or injury) to the body as a result of, for example, transport or industrial accidents, birth, surgery, heart attack, stroke, burns, complications due to surgery or other medical interventions etc. Trauma may result from injury to a body, both in a hospital or out of hospital. Trauma is often associated with trauma medicine practiced in hospital (such as in hospital emergency rooms), during emergency transport or at out-of-hospital environments where a trauma has occurred, such as domestic or industrial accidents, transport accidents, the battlefield, and terrorist attacks. In many cases, trauma therapy may also include resuscitation therapy.

The term "tissue" is used herein in its broadest sense and refers to any part of the body exercising a specific function including organs and cells or parts thereof, for example, cell lines or organelle preparations. Other examples include circulatory organs such as the heart, blood vessels and vasculature, respiratory organs such as the lungs, urinary organs such as the kidneys or bladder, digestive organs such as the stomach, liver, pancreas or spleen, reproductive organs such as the scrotum, testis, ovaries or uterus, neurological organs such as the brain, germ cells such as spermatozoa or ovum and somatic cells such as skin cells, heart cells ie, myocytes, nerve cells, brain cells or kidney cells. The tissues may come from human or animal donors. The donor organs may also be suitable for xenotransplantation.

The term "organ" is used herein in its broadest sense and refers to any part of the body exercising a specific function including tissues and cells or parts thereof, for example, endothelium, epithelium, blood brain barrier, cell lines or organelle preparations. Other examples include circulatory organs such as the blood vessels, heart, respiratory organs such as the lungs, urinary organs such as the kidneys or bladder, digestive organs such as the stomach, liver, pancreas or spleen, reproductive organs such as the scrotum, testis, ovaries or uterus, neurological organs such as the brain, germ cells such as spermatozoa or ovum and somatic cells such as skin cells, heart cells i.e., myocytes, nerve cells, brain cells or kidney cells.

It will also be understood that the term "comprises" (or its grammatical variants) as used in this specification is equivalent to the term "includes" and should not be taken as excluding the presence of other elements or features.

Potassium channel openers are agents which act on potassium channels to open them through a gating mechanism. This results in efflux of potassium across the membrane along its electrochemical gradient which is usually from inside to outside of the cell. Thus potassium channels are targets for the actions of transmitters, hormones, or drugs that modulate cellular function. It will be appreciated that the potassium channel openers include the potassium channel agonists which also stimulate the activity of the potassium channel with the same result. It will also be appreciated that there are diverse classes of compounds which open or modulate different potassium channels; for example, some channels are voltage dependent, some rectifier potassium channels are sensitive to ATP depletion, adenosine and opioids, others are activated by fatty acids, and other channels are modulated by ions such as sodium and calcium (ie. channels which respond to changes in cellular sodium and calcium). More recently, two pore potassium channels have been discovered and thought to function as background channels involved in the modulation of the resting membrane potential.

Potassium channel openers may be selected from the group consisting of: nicorandil, diazoxide, minoxidil, pinacidil, aprikalim, cromokulim and derivative U-89232, P-1075 (a selective plasma membrane KATP channel opener), emakalim, YM-934, (+)-7,8-dihydro-6,6-dimethyl-7-hydroxy-8-(2-oxo-1-piperidinyl)-6H-pyrano[2,3-f]benz-2,1,3-oxadiazole (NIP-121), RO316930, RWJ29009, SDZ-PCO400, rimakalim, symakalim, YM099, 2-(7,8-dihydro-6,6-dimethyl-6H-[1,4]oxazino[2,3-f][2,1,3]benzoxadiazol-8-yl)pyridine N-oxide, 9-(3-cyanophenyl)-3,4,6,7,9,10-hexahydro-1,8-(2H,5H)-acridinedione (ZM244085), [(9R)-9-(4-fluoro-3-125iodophenyl)-2,3,5,9-tetrahydro-4H-pyrano[3,4-b]thieno[2,3-e]pyridin-8(7H)-one-1,1-dioxide] ([125I]A-312110), (−)-N-(2-ethoxyphenyl)-N'-(1,2,3-trimethylpropyl)-2-nitroethene-1,1-diamine (Bay X 9228), N-(4-benzoyl phenyl)-3,3,3-trifluoro-2-hydroxy-2-methylpropionamine (ZD6169), ZD6169 (KATP opener) and ZD0947 (KATP opener), WAY-133537 and a novel dihydropyridine potassium channel opener, A-278637. In addition, potassium channel openers can be selected from BK-activators (also called BK-openers or BK(Ca)-type potassium channel openers or large-conductance calcium-activated potassium channel openers) such as benzimidazolone derivatives NS004 (5-trifluoromethyl-1-(5-chloro-2-hydroxyphenyl)-1,3-dihydro-2H-benzimidazole-2-one), NS1619 (1,3-dihydro-1-[2-hydroxy-5-(trifluoromethyl)phenyl]-5-(trifluoromethyl)-2H-benzimidazol-2-one), NS1608 (N-(3-(trifluoromethyl)phenyl)-N'-(2-hydroxy-5-chlorophenyl)urea), BMS-204352, retigabine (also GABA agonist). There are also intermediate (eg. benzoxazoles, chlorzoxazone and zoxazolamine) and small-conductance calcium-activated potassium channel openers. Other compounds that are believed to open KATP channels include Levosimendan and hydrogen sulphide gas ($H_2S$) or the $H_2S$ donors (eg sodium hydrosulphide, NaHS).

In addition, potassium channel openers may act as indirect calcium antagonists, ie they act to reduce calcium entry into the cell by shortening the cardiac action potential duration through the acceleration of phase 3 repolarisation, and thus shorten the plateau phase. Reduced calcium entry is thought to involve L-type calcium channels, but other calcium channels may also be involved.

Adenosine (6-amino-9-β-D-ribofuranosyl-9H-purine) is particularly preferred as the potassium channel opener. Adenosine is capable of opening the potassium channel, hyperpolarising the cell, depressing metabolic function, possibly protecting endothelial cells, enhancing preconditioning of tissue and protecting from ischaemia or damage. Adenosine is also an indirect calcium antagonist, vasodilator, antiarrhythmic, antiadrenergic, free radical scavenger, arresting agent, anti-inflammatory agent (attenuates neutrophil activation), metabolic agent and possible nitric oxide donor. More recently, adenosine is known to inhibit several steps which can lead to slowing of the blood clotting process. In addition, elevated levels of adenosine in the brain has been shown to cause sleep and may be involved in different forms of dormancy. An adenosine analogue, 2-chloro-adenosine, may be used.

Suitable adenosine receptor agonists may be selected from: $N^6$-cyclopentyladenosine (CPA), N-ethylcarboxamido adenosine (NECA), 2-[p-(2-carboxyethyl)phenethyl-amino-5'-N-ethylcarboxamido adenosine (CGS-21680), 2-chloroadenosine, N6-[2-(3,5-demethoxyphenyl)-2-(2-methoxyphenyl]ethyladenosine, 2-chloro-N6-cyclopentyladenosine (CCPA), N-(4-aminobenzyl)-9-[5-(methylcarbonyl)-beta-D-robofuranosyl]-adenine (AB-MECA), ([IS-[1a,2b,3b,4a(S*)]'-4-[7-[[2-(3-chloro-2-thienyl)-1-methyl-propyl]amino]-3H-imidazole[4,5-b]pyridyl-3-yl]cyclopentane carboxamide (AMP579), $N^6$—(R)-phenylisopropyladenosine (R-PLA), amino phenylethyladenosine (APNEA) and cyclohexyladenosine (CHA). CCPA is a particularly preferred. Others include full adenosine A1 receptor agonists such as N-[3-(R)-tetrahydrofuranyl]-6-aminopurine riboside (CVT-510), or partial agonists such as CVT-2759 and allosteric enhancers such as PD81723. Other agonists may include $N^6$-cyclopentyl-2-(3-phenylaminocarbonyltriazene-1-yl)adenosine (TCPA), a very selective agonist with high affinity for the human adenosine A1 receptor and allosteric enhancers of A1 adenosine receptor includes the 2-amino-3-napthoylthiophenes.

In one aspect, the composition according to the invention includes an A1 adenosine receptor agonist and a local anaesthetic. CCPA is a particularly preferred A1 adenosine receptor agonist.

Some embodiments of the invention utilise direct calcium antagonists, the principal action of which is to reduce calcium entry into the cell. These are selected from at least five major classes of calcium channel blockers as explained in more detail below. It will be appreciated that these calcium antagonists share some effects with potassium channel openers, particularly ATP-sensitive potassium channel openers, by inhibiting calcium entry into the cell.

Calcium channel blockers are also called calcium antagonists or calcium blockers. They are often used clinically to decrease heart rate and contractility and relax blood vessels. They may be used to treat high blood pressure, angina or discomfort caused by ischaemia and some arrhythmias, and they share many effects with beta-blockers, which could also be used to reduce calcium. Beta-blockers (or beta-adrenergic blocking agents) include atenolol (Tenormin™), propranolol hydrochloride (such as Inderal™), esmolol hydrochloride (Brevibloc™), metoprolol succinate (such as Lopressor™ or Toprol XL™), acebutolol hydrochloride (Sectral™), carteolol (such as Cartrol™) penbutolol sulfate (Levatol™) and pindolol (Visken™).

Five major classes of calcium channel blockers are known with diverse chemical structures: 1. Benzothiazepines: eg Diltiazem, 2. Dihydropyridines: eg nifedipine, Nicardipine, nimodipine and many others, 3. Phenylalkylamines: eg Verapamil, 4. Diarylaminopropylamine ethers: eg Bepridil, 5. Benzimidazole-substituted tetralines: eg Mibefradil.

The traditional calcium channel blockers bind to L-type calcium channels ("slow channels") which are abundant in cardiac and smooth muscle which helps explain why these drugs have selective effects on the cardiovascular system. Different classes of L-type calcium channel blockers bind to different sites on the alpha1-subunit, the major channel-forming subunit (alpha2, beta, gamma, delta subunits are also present). Different sub-classes of L-type channel are present which may contribute to tissue selectivity. More recently, novel calcium channel blockers with different specificities have also been developed for example, Bepridil, is a drug with Na+ and K+ channel blocking activities in addition to L-type calcium channel blocking activities. Another example is Mibefradil, which has T-type calcium channel blocking activity as well as L-type calcium channel blocking activity.

Three common calcium channel blockers are diltiazem (Cardizem), verapamil (Calan) and Nifedipine (Procardia). Nifedipine and related dihydropyridines do not have significant direct effects on the atrioventricular conduction system or sinoatrial node at normal doses, and therefore do not have direct effects on conduction or automaticity. While other calcium channel blockers do have negative chronotropic/dromotropic effects (pacemaker activity/conduction velocity). For example, Verapamil (and to a lesser extent diltiazem) decreases the rate of recovery of the slow channel in AV conduction system and SA node, and therefore act directly to depress SA node pacemaker activity and slow conduction. These two drugs are frequency- and voltage-dependent, making them more effective in cells that are rapidly depolarizing. Verapamil is also contraindicated in combination with beta-blockers due to the possibility of AV block or severe depression of ventricular function. In addition, mibefradil has negative chronotropic and dromotropic effects. Calcium channel blockers (especially verapamil) may also be particularly effective in treating unstable angina if underlying mechanism involves vasospasm.

Omega conotoxin MVIIA (SNX-111) is an N type calcium channel blocker and is reported to be 100-1000 fold more potent than morphine as an analgesic but is not addictive. This conotoxin is being investigated to treat intractable pain. SNX-482 a further toxin from the venom of a carnivorous spider venom, blocks R-type calcium channels. The compound is isolated from the venom of the African tarantula, Hysterocrates gigas, and is the first R-type calcium channel blocker described. The R-type calcium channel is believed to play a role in the body's natural communication network where it contributes to the regulation of brain function. Other Calcium channel blockers from animal kingdom include Kurtoxin from South African Scorpion, SNX-482 from African Tarantula, Taicatoxin from the Australian Taipan snake, Agatoxin from the Funnel Web Spider, Atracotoxin from the Blue Mountains Funnel Web Spider, Conotoxin from the Marine Snail, HWTX-I from the Chinese bird spider, Grammotoxin SIA from the South American Rose Tarantula. This list also includes derivatives of these toxins that have a calcium antagonistic effect.

Direct ATP-sensitive potassium channel openers (eg nicorandil, aprikalem) or indirect ATP-sensitive potassium channel openers (eg adenosine, opioids) are also indirect calcium antagonists and reduce calcium entry into the tissue. One mechanism believed for ATP-sensitive potassium channel openers also acting as calcium antagonists is shortening of the cardiac action potential duration by accelerating phase 3 repolarisation and thus shortening the plateau phase. During the plateau phase the net influx of calcium may be balanced by the efflux of potassium through potassium channels. The enhanced phase 3 repolarisation may inhibit calcium entry into the cell by blocking or inhibiting L-type calcium channels and prevent calcium (and sodium) overload in the tissue cell.

Calcium channel blockers can be selected from nifedipine, nicardipine, nimopidipine, nisoldipine, lercanidipine, telodipine, angizem, altiazem, bepridil, amlopidine, felodipine, isradipine and cavero and other racemic variations.

In a preferred form, the potassium channel opener or agonist and/or an adenosine receptor agonist has a blood half-life of less than one minute, preferably less than 20 seconds.

In some embodiments, the composition may include additional potassium channel openers or agonists, for example diazoxide or nicorandil.

The inventor has also found that the inclusion of diazoxide with a potassium channel opener or adenosine receptor agonist and a local anaesthetic reduces injury. Thus in another aspect, the composition according to the invention further includes diazoxide.

Diazoxide is a potassium channel opener and in the present invention it is believed to preserve ion and volume regulation, oxidative phosphorylation and mitochondrial membrane integrity (appears concentration dependent). More recently, diazoxide has been shown to provide cardioprotection by reducing mitochondrial oxidant stress at reoxygenation. At present it is not known if the protective effects of potassium channel openers are associated with modulation of reactive oxygen species generation in mitochondria. Preferably the concentration of the diazoxide is between about 1 to 200 uM. Typically this is as an effective amount of diazoxide. More preferably, the concentration of diazoxide is about 10 uM.

The inventor has also found that the inclusion of nicorandil with a potassium channel opener or adenosine receptor agonist and a local anaesthetic reduces injury. Thus in another aspect, the composition according to the invention further includes nicorandil.

Nicorandil is a potassium channel opener and nitric oxide donor which can protect tissues and the microvascular integrity including endothelium from ischemia and reperfusion damage. Thus it can exert benefits through the dual action of opening KATP channels and a nitrate-like effect. Nicorandil can also reduce hypertension by causing blood vessels to dilate which allows the heart to work more easily by reducing both preload and afterload. It is also believed to have anti-inflammatory and anti-proliferative properties which can further attenuates ischemia/reperfusion injury.

The composition according to the invention also includes a compound for inducing local anaesthesia, otherwise known as a local anaesthetic. The local anaesthetic may be selected from mexiletine, diphenylhydantoin, prilocaine, procaine, mepivocaine, quinidine, disopyramide and Class 1B antiarrhythmic agents such as lignocaine or derivatives thereof, for example, QX-314.

Preferably the local anaesthetic is Lignocaine. In this specification, the terms "lidocaine" and "lignocaine" are used interchangeably. Lignocaine is preferred as it is capable of acting as a local anaesthetic probably by blocking sodium fast channels, depressing metabolic function, lowering free cytosolic calcium, protecting against enzyme release from cells, possibly protecting endothelial cells and protecting against myofilament damage. At lower therapeutic concentrations lignocaine normally has little effect on atrial tissue, and therefore is ineffective in treating atrial fibrillation, atrial flutter, and supraventricular tachycardias. Lignocaine is also a free radical scavenger, an antiarrhythmic and has anti-inflammatory and anti-hypercoagulable properties. It must also be appreciated that at non-anaesthetic therapeutic concentrations, local anaesthetics like lignocaine would not completely block the voltage-dependent sodium fast channels, but would down-regulate channel activity and reduce sodium entry. As anti-arrhythmic, lignocaine is believed to target small sodium currents that normally continue through phase 2 of the action potential and consequently shortens the action potential and the refractory period.

As lignocaine acts by primarily blocking sodium fast channels, it will be appreciated that other sodium channel blockers may be used instead of or in combination with the local anaesthetic in the method and composition of the present invention. It will also be appreciated that sodium channel blockers include compounds that act to substantially block sodium channels or at least downregulate sodium channels. Examples of suitable sodium channel blockers include venoms such as tetrodotoxin and the drugs primaquine, QX, HNS-32 (CAS Registry #186086-10-2), NS-7, kappa-opioid receptor agonist U50 488, crobenetine, pilsicamide, phenyloin, tocamide, mexiletine, NW-1029 (a benzylamino propanamide derivative), RS100642, riluzole, carbamazepine, flecamide, propafenone, amiodarone, sotalol, bretylium, imipramine and moricizine, or any of derivatives thereof. Other suitable sodium channel blockers include: Vinpocetine (ethyl apovincaminate); and Beta-carboline derivative, nootropic beta-carboline (ambocarb, AMB).

In one aspect, the composition according to the invention consists essentially of (i) a potassium channel opener or agonist and/or an adenosine receptor agonist; and (ii) a local anaesthetic.

In another aspect, the composition according to the invention may further include an opioid. The further addition of an opioid may have similar if not improved effect on the reduction of injury.

Opioids, also known or referred to as opioid agonists, are a group of drugs that inhibit opium (Gr opion, poppy juice) or morphine-like properties and are generally used clinically as moderate to strong analgesics, in particular, to manage pain, both perk and post-operatively. Other pharmacological effects of opioids include drowsiness, respiratory depression, changes in mood and mental clouding without loss of consciousness.

Opioids are also believed to be involved as part of the 'trigger' in the process of hibernation, a form of dormancy characterised by a fall in normal metabolic rate and normal core body temperature. In this hibernating state, tissues are better preserved against damage that may otherwise be caused by diminished oxygen or metabolic fuel supply, and also protected from ischemia reperfusion injury.

There are three types of opioid peptides: enkephalin, endorphin and dynorphin. Opioids act as agonists, interacting with stereospecific and saturable binding sites, in the heart, brain and other tissues. Three main opioid receptors have been identified and cloned, namely mu, kappa, and delta receptors. All three receptors have consequently been classed in the G-protein coupled receptors family (which class includes adenosine and bradykinin receptors). Opioid receptors are further subtyped, for example, the delta receptor has two subtypes, delta-1 and delta-2.

Cardiovascular effects of opioids are directed within the intact body both centrally (ie, at the cardiovascular and respiratory centres of the hypothalamus and brainstem) and peripherally (ie, heart myocytes and both direct and indirect effects on the vasculature). For example, opioids have been shown to be involved in vasodilation. Some of the action of opioids on the heart and cardiovascular system may involve direct opioid receptor mediated actions or indirect, dose dependent non-opioid receptor mediated actions, such as ion channel blockade which has been observed with antiarrhythmic actions of opioids, such as arylacetamide drugs. It is also known that the heart is capable of synthesising or producing the three types of opioid peptides, namely, enkephalin, endorphin and dynorphin. However, only the delta and kappa opioid receptors have been identified on ventricular myocytes.

Without being bound by any mode of action, opioids are considered to provide cardioprotective effects, by limiting ischemic damage and reducing the incidence of arrhythmias, which are produced to counter-act high levels of damaging agents or compounds naturally released during ischemia. This may be mediated via the activation of ATP sensitive potassium channels in the sarcolemma and in the mitochondrial membrane and involved in the opening potassium channels. Further, it is also believed that the cardioprotective effects of opioids are mediated via the activation of ATP sensitive potassium channels in the sarcolemma and in the mitochondrial membrane. Thus it is believed that the opioid can be used instead or in combination with the potassium channel opener or adenosine receptor agonist as they are also involved in indirectly opening potassium channels.

It will be appreciated that the opioids include compounds (natural or synthetic) which act both directly and indirectly on opioid receptors. Opioids also include indirect dose dependent, non-opioid receptor mediated actions such as ion channel blockade which have been observed with the antiarrhythmic actions of opioids.

Accordingly, the opioid may be selected from enkephalins, endorphins and dynorphins. Preferably the opioid is an enkephalin which targets delta, kappa and/or mu receptors. More preferably the opioid is a delta opioid receptor agonist. Even more preferably the opioid is selected from delta-1-opioid receptor agonists and delta-2-opioid receptor agonists. [D-Pen 2, 5] enkephalin (DPDPE), is a particularly preferred delta-1-opioid receptor agonist.

In another aspect the composition of the invention consists essentially of (i) a potassium channel opener or agonist and/or an adenosine receptor agonist; (ii) a local anaesthetic and (iii) a delta-1-opioid. DPDPE is a particularly preferred delta-1-opioid receptor agonist.

The inventor has found that the inclusion of a compound for minimizing or reducing the uptake of water by a cell in a tissue with a potassium channel opener or adenosine receptor agonist and a local anaesthetic assists in reducing injury to a body, such as a composition comprising sucrose, adenosine and lignocaine.

Thus in a further aspect, the composition according to the invention may further include at least one compound for minimizing or reducing the uptake of water by a cell in the cell, tissue or organ.

A compound for minimizing or reducing the uptake of water by a cell in the tissue tends to control water shifts, ie, the shift of water between the extracellular and intracellular environments. Accordingly, these compounds are involved in the control or regulation of osmosis. One consequence is that a compound for minimizing or reducing the uptake of water by a cell in the tissue reduces cell swelling that is associated with Oedema, such as Oedema that can occur during ischemic injury.

Compounds for minimizing or reducing the uptake of water by a cell in a tissue are typically impermeants or receptor antagonists or agonists. An impermeant according to the present invention may be selected from one or more of the group consisting of: sucrose, pentastarch, hydroxyethyl starch, raffinose, mannitol, gluconate, lactobionate, and colloids. Colloids include albumin, hetastarch, polyethylene glycol (PEG), Dextran 40 and Dextran 60. Other compounds that could be selected for osmotic purposes include those from the major classes of osmolytes found in the animal kingdom including polyhydric alcohols (polyols) and sugars, other amino acids and amino-acid derivatives, and methylated ammonium and sulfonium compounds.

Cell swelling can also result from an inflammatory response which may be important during organ retrieval, preservation and surgical grafting. Substance P, an important pro-inflammatory neuropeptide is known to lead to cell oedema and therefore antagonists of substance P may reduce cell swelling. Indeed antagonists of substance P, (-specific neurokinin-1) receptor (NK-1) have been shown to reduce inflammatory liver damage, i.e., oedema formation, neutrophil infiltration, hepatocyte apoptosis, and necrosis. Two such NK-1 antagonists include CP-96,345 or [(2S,3S)-cis-2-(diphenylmethyl)-N-((2-methoxyphenyl)-methyl)-1-azabi-cyclo(2.2.2.)-octan-3-amine (CP-96,345)] and L-733,060 or [(2S,3S)$_3$-([3,5-bis(trifluoromethyl)phenyl]methoxy)-2-phenylpiperidine]. R116301 or [(2R-trans)-4-[1-[3,5-bis(tri-fluoromethyl)benzoyl]-2-(phenylmethyl)-4-piperidinyl]-N-(2,6-dimethylphenyl)-1-acetamide(S)-Hydroxybutanedioate] is another specific, active neurokinin-1 (NK(1)) receptor antagonist with subnanomolar affinity for the human NK(1) receptor (K(i): 0.45 nM) and over 200-fold selectivity toward NK(2) and NK(3) receptors. Antagonists of neurokinin receptors 2 (NK-2) that may also reduce cell swelling include SR48968 and NK-3 include SR142801 and SB-222200. Blockade of mitochondrial permeability transition and reducing the membrane potential of the inner mitochondrial membrane potential using cyclosporin A has also been shown to decrease ischemia-induced cell swelling in isolated brain slices. In addition glutamate-receptor antagonists (AP5/CNQX) and reactive oxygen species scavengers (ascorbate, Trolox®, dimethylthiourea, Tempol®) also showed reduction of cell swelling. Thus, the compound for minimizing or reducing the uptake of water by a cell in a tissue can also be selected from any one of these compounds.

It will also be appreciated that the following energy substrates can also act as impermeants. Suitable energy substrate can be selected from one or more from the group consisting of: glucose and other sugars, pyruvate, lactate, glutamate, glutamine, aspartate, arginine, ectoine, taurine, N-acetyl-beta-lysine, alanine, proline, beta-hydroxy butyrate and other amino acids and amino acid derivatives, trehalose, floridoside, glycerol and other polyhydric alcohols (polyols), sorbitol, myo-innositol, pinitol, insulin, alpha-keto glutarate, malate, succinate, triglycerides and derivatives, fatty acids and carnitine and derivatives. In one embodiment, the at least one compound for minimizing or reducing the uptake of water by the cells in the tissue is an energy substrate. The energy substrate helps with recovering metabolism. The energy substrate can be selected from one or more from the group consisting of: glucose and other sugars, pyruvate, lactate, glutamate, glutamine, aspartate, arginine, ectoine, taurine, N-acetyl-beta-lysine, alanine, proline and other amino acids and amino acid derivatives, trehalose, floridoside, glycerol and other polyhydric alcohols (polyols), sorbitol, myo-innositol, pinitol, insulin, alpha-keto glutarate, malate, succinate, triglycerides and derivatives, fatty acids and carnitine and derivatives. Given that energy substrates are sources of reducing equivalents for energy transformations and the production of ATP in a cell, tissue or organ of the body, it will be appreciated that a direct supply of the energy reducing equivalents could be used as substrates for energy production. For example, a supply of either one or more or different ratios of reduced and oxidized forms of nicotinamide adenine dinucleotide (e.g. NAD or NADP and NADH or NADPH) or flavin adenine dinucleotides (FADH or FAD) could be directly used to supply bond energy for sustaining ATP production in times of stress. Preferably, beta-hydroxy butyrate is added to the composition of the invention for treatment of trauma or reducing injury.

In addition to providing energy substrates to the whole body, organ, tissue or cell, improvements in metabolising these substrates may occur in the presence of hydrogen sulphide ($H_2S$) or $H_2S$ donors (eg NaHS). The presence of hydrogen sulphide ($H_2S$) or H2S donors (eg NaHS) may help metabolise these energy substrates by lowering energy demand during arrest, protect and preserve the whole body, organ, tissue or cell during periods of metabolic imbalance such ischemia, reperfusion and trauma. Concentrations of Hydrogen sulfide above 1 microM (10-6 M) concentration can be a metabolic poison that inhibits respiration at Respiratory Complex IV, which is part of the mitochondrial respiratory chain that couples metabolising the high energy reducing equivalents from energy substrates to energy (ATP) generation and oxygen consumption. However, it has been observed at lower concentrations, below $10^{-6}$ M (eg $10^{-10}$ to $10^{-9}$M), hydrogen sulfide may reduce the energy demand of the whole body, organ, tissue or cell which may result in arrest, protection and preservation. In other words, very low levels of sulfide down-regulate mitochondria, reduce $O_2$ consumption and actually increase "Respiratory Control" whereby mitochondria consume less $O_2$ without collapsing the electrochemical gradient across the inner mitochondrial membrane. Thus there are observations that a small amount of sulfide, either directly or indirectly, may close proton leak channels and better couple mitochondrial respiration to ATP production more tightly, and this effect may improve the metabolism of high energy reducing equivalents from energy substrates. There is also the possibility that a sulphur cycle exists between the cell cytosol and mitochondria in mammals, including humans, providing the sulphur concentration is low. The presence of a vestige sulphur cycle would be consistent with current ideas on the evolutionary origin of mitochondria and their appearance in eukaryote cells from a symbiosis between a sulfide-producing host cell and a sulfide-oxidizing bacterial symbiont. Thus, hydrogen sulphide ($H_2S$) or $H_2S$ donors (eg NaHS) may be energy substrates themselves in addition to improving the metabolism of other energy substrates. Accordingly, in one form, the invention provides a composition as described above further including hydrogen sulphide or a hydrogen sulfide donor.

In one embodiment, the at least one compound for minimizing or reducing the uptake of water by the cells in the tissue is sucrose. Sucrose reduces water shifts as an impermeant. Impermeant agents such as sucrose, lactobionate and raffinose are too large to enter the cells and hence remain in the extracellular spaces within the tissue and resulting osmotic forces prevent cell swelling that would otherwise damage the tissue, which would occur particularly during storage of the tissue.

In another embodiment, the at least one compound for minimizing or reducing the uptake of water by the cells in the tissue is a colloid. Suitable colloids include, but not limited to, Dextran-70, 40, 50 and 60, hydroxyethyl starch and a modified fluid gelatin. A colloid is a composition which has a continuous liquid phase in which a solid is suspended in a liquid. Colloids can be used clinically to help restore balance to water and ionic distribution between the intracellular, extracellular and blood compartments in the body after an severe injury. Colloids can also be used in solutions for organ preservation. Administration of crystalloids can also restore water and ionic balance to the body but generally require greater volumes of administration because they do not have solids suspended in a liquid. Thus volume expanders may be colloid-based or crystalloid-based Preferably, the concentration of the compound for minimizing or reducing the uptake of water by the cells in the tissue is between about 5 to 500 mM. Typically this is an effective amount for reducing the uptake of water by the cells in the tissue. More preferably, the concentration of the compound for reducing the uptake of water by the cells in the tissue is between about 20 and 100 mM. Even more preferably the concentration of the compound for reducing the uptake of water by the cells in the tissue is about 70 mM.

In a further embodiment, the composition according to the invention may include more than one compound for minimizing or reducing the uptake of water by the cells in the tissue. For example, a combination of impermeants (raffinose, sucrose and pentastarch) may be included in the composition or even a combination of colloids, and fuel substrates may be included in the composition.

The composition according to the invention may be hypo, iso or hyper osmotic.

The inventor has also found that the inclusion of a compound for inhibiting transport of sodium and hydrogen ions across a plasma membrane of a cell in the tissue with a potassium channel opener or adenosine receptor agonist and a local anaesthetic assists in reducing injury.

Thus in another aspect, the composition according to the invention further includes a compound for inhibiting transport of sodium and hydrogen ions across a plasma membrane of a cell in the tissue.

The compound for inhibiting transport of sodium and hydrogen across the membrane of the cell in the tissue is also referred to as a sodium hydrogen exchange inhibitor. The sodium hydrogen exchange inhibitor reduces sodium and calcium entering the cell.

Preferably the compound for inhibiting transport of sodium and hydrogen across the membrane of the cell in the tissue may be selected from one or more of the group consisting of Amiloride, EIPA(5-(N-entyl-N-isopropyl)-amiloride), cariporide (HOE-642), eniporide, Triamterene (2,4,7-triamino-6-phenylteride), EMD 84021, EMD 94309, EMD 96785, EMD 85131, HOE 694. B11 B-513 and T-162559 are other inhibitors of the isoform 1 of the Na+/H+ exchanger.

Preferably, the sodium hydrogen exchange inhibitor is Amiloride (N-amidino-3,5-diamino-6-chloropyrzine-2-carboximide hydrochloride dihydrate). Amiloride inhibits the sodium proton exchanger (Na+/H+ exchanger also often abbreviated NHE-1) and reduces calcium entering the cell. During ischemia excess cell protons (or hydrogen ions) are believed to be exchanged for sodium via the Na+/H+ exchanger.

Preferably, the concentration of the compound for inhibiting transport of sodium and hydrogen across the membrane of the cell in the tissue is between about 1.0 nM to 1.0 mM. More preferably, the concentration of the compound for inhibiting transport of sodium and hydrogen across the membrane of the cell in the tissue is about 20 uM.

The inventor has also found that the inclusion of antioxidant with a potassium channel opener or adenosine receptor agonist and a local anaesthetic. Thus in another aspect, the composition of the present invention may further include an antioxidant.

Antioxidants are commonly enzymes or other organic substances that are capable of counteracting the damaging effects of oxidation in the tissue. The antioxidant component of the composition according to the present invention may be selected from one or more of the group consisting of: allopurinol, carnosine, histidine, Coenzyme Q 10, n-acetyl-cysteine, superoxide dismutase (SOD), glutathione reductase (GR), glutathione peroxidase (GP) modulators and regulators, catalase and the other metalloenzymes, NADPH and AND(P)H oxidase inhibitors, glutathione, U-74006F, vitamin E, Trolox (soluble form of vitamin E), other tocopherols (gamma and alpha, beta, delta), tocotrienols, ascorbic acid, Vitamin C, Beta-Carotene (plant form of vitamin A), selenium, Gamma Linoleic Acid (GLA), alpha-lipoic acid, uric acid (urate), curcumin, bilirubin, proanthocyanidins, epigallocatechin gallate, Lutein, lycopene, bioflavonoids, polyphenols, Trolox®, dimethylthiourea, Tempol®, carotenoids, coenzyme Q, melatonin, flavonoids, polyphenols, aminoindoles, probucol and nitecapone, 21-aminosteroids or lazaroids, sulphydryl-containing compounds (thiazolidine, Ebselen, dithiolethiones), and N-acetylcysteine. Other antioxidants include the ACE inhibitors (captopril, enalapril, lisinopril) which are used for the treatment of arterial hypertension and cardiac failure on patients with myocardial infarction. ACE inhibitors exert their beneficial effects on the reoxygenated myocardium by scavenging reactive oxygen species. Other antioxidants that could also be used include beta-mercaptopropionylglycine, O-phenanthroline, dithiocarbamate, selegilize and desferrioxamine (Desferal), an iron chelator, has been used in experimental infarction models, where it exerted some level of antioxidant protection. Spin trapping agents such as 5'-5-dimethyl-1-pyrrolione-N-oxide (DMPO) and (a-4-pyridyl-1-oxide)-N-t-butylnitrone (POBN) also act as antioxidants. Other antioxidants include: nitrone radical scavenger alpha-phenyl-tert-N-butyl nitrone (PBN) and derivatives PBN (including disulphur derivatives); N-2-mercaptopropionyl glycine (MPG) a specific scavenger of the OH free radical; lipooxygenase inhibitor nordihydroguaretic acid (NDGA); Alpha Lipoic Acid; Chondroitin Sulfate; L-Cysteine; oxypurinol and Zinc.

Preferably, the antioxidant is allopurinol (1H-Pyrazolo[3, 4-a]pyrimidine-4-ol). Allopurinol is a competitive inhibitor of the reactive oxygen species generating enzyme xanthine oxidase. Allopurinol's antioxidative properties may help preserve myocardial and endothelial functions by reducing oxidative stress, mitochondrial damage, apoptosis and cell death. Preferably, the concentration of the antioxidant is between about 1 nM to 100 uM.

The inventor has also found that the inclusion of particular amounts of calcium and magnesium ions with a potassium channel opener or adenosine receptor agonist and a local anaesthetic reduces injury. The effect of the particular amounts of calcium and magnesium ions is to control the amount of ions within the intracellular environment. Calcium ions tend to be depleted, exported or otherwise removed from the intracellular environment and magnesium ions tend to be increased or otherwise restored to the levels typically found in a viable, functioning cell.

Thus in another aspect, the composition according to the invention further includes a source of magnesium in an amount for increasing the amount of magnesium in a cell in body tissue. Preferably the magnesium is present at a concentration of between 0.5 mM to 20 mM, more preferably about 2.5 mM. It will be appreciated that these concentrations refer to the effective concentration of the magnesium in the composition that contacts the tissue, organ or cell.

In addition, typical buffers or carriers (which are discussed in more detail below) in which the composition of the invention is administered typically contain calcium at concentrations of around 1 mM as the total absence of calcium has been found to be detrimental to the cell, tissue or organ. In one form, the invention also includes using carriers with low calcium (such as for example less than 0.5 mM) so as to decrease the amount of calcium within a cell in body tissue, which may otherwise build up during injury/trauma/stunning. As described in the present invention, elevated magnesium and low calcium has been associated with protection during ischemic and reoxygenation of an organ. The action is believed to be due to decreased calcium loading. Preferably the calcium present is at a concentration of between 0.1 mM to 0.8 mM, more preferably about 0.3 mM.

In one embodiment, the composition includes elevated divalent magnesium ions. Magnesium sulphate and magnesium chloride is a suitable source.

In the case of a human subject requiring treatment, the following alternative compositions with corresponding concentrations of Adenosine (Ado), Lignocaine (Lido) and magnesium sulphate are provided, without limitation:

|      | Ado      | Lido      | MgSO4 7 H2O |
|------|----------|-----------|-------------|
| I    | 2.25 mM  | 1.844 mM  | 243.4 mM    |
| II   | 3.74 mM  | 3.688 mM  | 243.4 mM    |
| III  | 3.74 mM  | 7.376 mM  | 243.4 mM    |
| IV   | 5.61 mM  | 3.688 mM  | 243.4 mM    |
| V    | 5.61 mM  | 7.376 mM  | 243.4 mM    |
| VI   | 22.5 mM  | 18.44 mM  | 243.4 mM    |
| VII  | 37.4 mM  | 36.88 mM  | 243.4 mM    |
| VIII | 37.4 mM  | 73.76 mM  | 243.4 mM    |
| IX   | 56.1 mM  | 36.88 mM  | 243.4 mM    |
| X    | 56.1 mM  | 73.76 mM  | 243.4 mM    |

The concentrations of each respective active ingredient in these compositions refer to the concentrations in the composition before administration. It will be appreciated that the concentrations may be diluted by body fluids or other fluids that may be administered together with the composition. Typically, the composition will be administered such that the concentration of these ingredients at the tissue is about 100-fold less than the concentrations in the table above. For example, containers (such as vials) of such a composition may be diluted 1 to a 100 parts of blood, plasma, crystalloid or blood substitute for administration.

In one embodiment, the composition according to the invention includes Adenosine and Lignocaine. Typically, the concentration of Adenosine and Lidocaine in the composition is between about 1 mM to 100 mM. The final concentration of these components once administered may be between about 0.1 mM to 10 mM.

In another embodiment, the composition includes a cellular transport enzyme inhibitor, such as dipyridamole, to prevent metabolism or breakdown of components in the composition.

In a further aspect, the invention provides a composition including a local anaesthetic and one or more of:
  potassium channel opener;
  adenosine agonist;
  opioid;
  at least one compound for reducing uptake of water;
  sodium hydrogen exchange inhibitor;
  antioxidant; and
  a source of magnesium in an amount for increasing the amount of magnesium in a cell in body tissue.

Preferably, this composition has two, three or four of the above. Preferred compounds for these components are listed above.

In another embodiment, the invention provides a composition including a potassium channel opener and/or an adenosine agonist and one or more of:
  local anaesthetic;
  opioid;
  at least one compound for reducing uptake of water;
  sodium hydrogen exchange inhibitor;
  antioxidant; and
  a source of magnesium in an amount for increasing the amount of magnesium in a cell in body tissue.

Preferably, this composition has two, three or four of the above. Preferred compounds for these components are listed above.

The processes of inflammation and thrombosis are linked through common mechanisms. Therefore, it is believed that understanding of the processes of inflammation will help with better management of thrombotic disorders including the treatment of acute and chronic ischaemic syndromes. In the clinical and surgical settings, a rapid response and early intervention to an organ or tissue damaged from ischemia can involve both anti-inflammatory and anti-clotting therapies. In addition to protease inhibitors which attenuate the inflammatory response, further anti-inflammatory therapies have included the administration of aspirin, normal heparin, low-molecular-weight heparin (LMWH), non-steroidal anti-inflammatory agents, anti-platelet drugs and glycoprotein (GP) IIb/IIIa receptor inhibitors, statins, angiotensin converting enzyme (ACE) inhibitor, angiotensin blockers and antagonists of substance P. Examples of protease inhibitors are indinavir, nelfinavir, ritonavir, lopinavir, amprenavir or the broad-spectrum protease inhibitor aprotinin, a low-molecular-weight heparin (LMWH) is enoxaparin, non-steroidal anti-inflammatory agent are indomethacin, ibuprofen, rofecoxib, naproxen or fluoxetine, an anti-platelet drug is Clopidogrel or aspirin, a glycoprotein (GP) IIb/IIIa receptor inhibitor is abciximab, a statin is pravastatin, an angiotensin converting enzyme (ACE) inhibitor is captopril and an angiotensin blocker is valsartin.

Accordingly, in another embodiment of the invention, a selection of these agents is added to a composition according to the invention to deliver improved management of inflammation and clotting. Alternatively, the composition according to the invention may be administered together with any one or more of these agents.

In particular, protease inhibitors attenuate the systemic inflammatory response in patients undergoing cardiac surgery with cardiopulmonary bypass, and other patients where the inflammatory response has been heightened such as AIDS or in the treatment of chronic tendon injuries. Some broad spectrum protease inhibitors such as aprotinin are also reduce blood loss and need for blood transfusions in surgical operations such as coronary bypass.

Compounds that substantially prevent the breakdown of adenosine in the blood such as nucleoside transport inhibitors, such as dipyridamole could be are used as additives in the composition of the invention. The half life of adenosine in the blood is about 10 seconds so the presence of a medicament to substantially prevent its breakdown will maximise the effect of the composition of the present invention.

Optionally, the composition according to the invention may also include Dipyridamole is advantageously included in a concentration from about 0.01 microM to about 10 mM, preferably 0.05 to 100 microM. Dipyridamole and has major advantages with respect to cardioprotection. Dipyridamole may supplement the actions of adenosine by inhibiting adenosine transport and breakdown leading to increased protection of cells, tissues and organs of the body during times of stress. Dipyridamole may also be administered separately for example by 400 mg daily tablets to produce a plasma level of about 0.4 microgram/ml, or 0.8 microM concentration.

The composition according to the present invention is highly beneficial at about 10° C. but can also be used to prevent injury over a wider temperature range up to about 37° C. The composition according to the invention may be used at a temperature range selected from the following: 0° C. to 5° C., 5° C. to 20° C., 20° C. to 32° C. and 32° C. to 38° C.

The composition may be administered intravenously or be administered both intravenously and intraperitoneally or in special circumstances directly accessing a major artery such as the femoral artery or aorta in patients who have no pulse from massive exsanguination. In one embodiment, the composition of the invention may be administered intravenously and intraperineally simultaneously, the perineum acting as, in effect, a reservoir of composition for the bloodstream as well as acting on organs in the vicinity with which it comes into contact. This is particularly suitable for a trauma victim, such as one suffering shock.

As described herein, in particular embodiments of the invention, the composition of the present invention protects and preserves tissue of a body after trauma, such as heart attacks, strokes etc, with good to excellent recoveries of function or viability of body tissue after reperfusion.

Affecting viability of a tissue during preservation and recovery of the body tissue, such that affected tissue remains viable or living during those processes and is capable of returning to its function, particularly after the tissue has been subject to shock, is crucial.

Preferably, reducing injury to a body relates to maintaining affected tissue in a viable state, such that the tissue is capable of returning to its function, after trauma. Maintaining or stabilising the tissue in a viable state includes maintaining the membrane potential of tissue cells at or around resting level, so as to reduce sodium or calcium loading of the cell which is a cause of injury during ischaemia and reperfusion. Preservation is known as the act or process of preserving the tissue or keeping from injury, destruction or decay. In this application, the composition according to the invention acts to minimise any potential injury, destruction or decay of the tissue of a body which may be caused by trauma.

Injury can be broadly characterised as reversible and irreversible cell injury. For example, reversible cell injury can lead to heart dysfunction usually from arrhythmias and/or stunning. Stunning is normally characterised as loss of left pump function during restoration of blood flow following periods of ischemia. If severe, it can lead to the death of the heart, usually from arrhythmias, even though the heart cells themselves are not initially dead. Irreversible injury by definition arises from actual cell death which may be fatal depending upon the extent of the injury. The amount of cell death can be measured as infarct size. During recovery from cardioplegic arrest, if the conditions are adequate, the heart can be restored substantially to normal function of the tissue by reperfusion, with minimal infarct size. The most common ways to assess return of function of a heart are by measuring pressures that the heart can generate:

heart pump flow; and the electrical activity of the heart.

This data is then compared to data measured from pre-arrest conditions.

The composition of the present invention is particularly useful in reducing injury to heart tissue during heart surgery (open-heart or robotic heart surgery), including heart transplants, and neonate/infant hearts. Other applications include reducing heart damage before, during or following cardiovascular intervention which may include a heart attack, angioplasty or angiography. For example, the composition may be administered to subjects who have suffered or are developing a heart attack and used at the time of administration of blood clot-busting drugs such as streptokinase. As the clot is dissolved, the presence of the composition may protect the heart from further injury such as reperfusion injury. The composition may be particularly effective as a cardioprotectant in those portions of the heart that have been starved of normal flow, nutrients and/or oxygen for different periods of time. For example, the pharmaceutical composition may also be used to treat heart ischaemia which could be pre-existing or induced by cardiovascular intervention. Other applications include assisting in diagnostic procedures such as assessment of a subject's health while exercising on a treadmill or, if subjects cannot exercise on a treadmill, to assist in visualising areas of the body such as the heart that may have partially or fully blocked blood vessels, or damaged heart cells. In addition, the invention may be used during different visualization procedures such as X-ray (routine and computerized tomography) or magnetic resonance imaging (MRI) of a subject's body or organs and tissues within the body or isolated from the body. In addition to providing better visualisation of potential areas of injury or damage, the invention may be used to temporarily lower the heart rate of a subject and thereby reduce movement (ie. from increasing heart relaxation) and permit faster scan times during the diagnostic assessment of potential injury in a blood vessel, tissue or organ of the body, particularly in the heart. Lowering heart rate and permitting faster scan times may also lower the doses of radiation required to visualize the potential areas of injury or damage.

Accordingly, in another embodiment of the invention, there is provided a method of preserving a vessel, tissue or organ of the body, such as a heart, comprising administering a composition as described above before, during or after medical intervention affecting the vessel, tissue or organ of the body, such as a heart. The composition used in this embodiment of the invention may have an arresting or a non-arresting concentration of active components in it. In one form, the method includes administering a non-arresting concentration of the composition and, in another form, it has an arresting concentration of the composition (preferably as a bolus) followed by a non-arresting concentration of the composition.

In another embodiment, the present invention may be administered with or contain blood or blood products or artificial blood or oxygen binding molecules or solutions to improve the body's oxygen transport ability and survival by helping to reduce hypoxic and ischemic damage from blood loss. The oxygen-containing molecules, compounds or solutions may be selected from natural or artificial products. For example, an artificial blood-based product is perfluorocarbon-based or other haemoglobin-based substitute. Some of the components may be added to mimic human blood's oxygen transport ability such Hemopure™, Gelenpol™, Oxygent™, and PolyHeme™. Hemopore is based on a chemically stabilized bovine hemoglobin. Gelenpol is a polymerized hemoglobin which comprises synthetic water-soluble polymers and modified heme proteins. Oxygent is a perflubron emulsion for use as an intravenous oxygen carrier to temporarily substitute for red blood cells during surgery. Polyheme is a human hemoglobin-based solution for the treatment of life-threatening blood loss.

It is believed that the oxygenation of the body from a variety of ways including but not limited to oxygen gas mixture, blood, blood products or artificial blood or oxygen binding solutions maintains mitochondrial oxidation and this helps preserve the myocyte and endothelium of the organ. Without being bound by any particular mode or theory, the inventor has found that gentle bubbling with 95% $O_2$/5% $CO_2$ helps maintains mitochondrial oxidation which helps preserve the myocyte and coronary vasculature.

In one preferred embodiment of this aspect of the present invention with respect to whole body or organs outside the body, the composition is aerated with a source of oxygen before and/or during use. The source of oxygen may be an oxygen gas mixture where oxygen is the predominant component. The oxygen may be mixed with, for example, $CO_2$. Preferably, the oxygen gas mixture is 95% $O_2$ and 5% $CO_2$.

In another aspect of the present invention there is provided a method for reducing injury including:
 providing in a suitable container a composition according to the invention;
 providing one or more nutrient molecules selected from the group consisting of blood, blood products, artificial blood and a source of oxygen;
 optionally aerating the composition with the oxygen (for example, in the case of isolated organs) or combining the nutrient molecules with the composition, or both; and
 placing the tissue in contact with the combined composition under conditions sufficient to reduce injury.

Preferably the oxygen source is an oxygen gas mixture. Preferably oxygen is the predominant component. The oxygen may be mixed with, for example $CO_2$. More preferably, the oxygen gas mixture is 95% $O_2$ and 5% $CO_2$. Preferably the composition is aerated before and/or during contact with the tissue.

The composition according to this aspect of the invention may be in liquid form. Liquid preparations of the pharmaceutical composition may take the form of, for example, solutions, syrups, or suspensions, or may be presented as a dry product for constitution with water or other suitable vehicle. Such liquid preparations may be prepared by conventional means with pharmaceutically acceptable additives such as suspending agents, emulsifying agents, non-aqueous vehicles, preservatives and energy sources. In another form, the invention comprises a composition in tablet form and in another form, the invention comprises an aerosol which could be administered via oral, skin or nasal routes.

In another aspect of the invention, there is provided a method of protecting heart tissue from reperfusion injury, including inflammatory and blood clotting and coagulation effects often experienced during reperfusion following an ischaemic event, such as in the post-operative period or longer-term recovery. The method comprises administering a solution comprising a non-arresting form of the composition according to the present invention, optionally following a bolus of an arresting form.

The invention also provides a method for reducing infarction size and/or reducing inflammation and blood coagulation responses in heart tissue during ischaemia and/or reperfusion comprising administration of the same solution.

The body may be a human or an animal such as a livestock animal (eg, sheep, cow or horse), laboratory test animal (eg, mouse, rabbit or guinea pig) or a companion animal (eg, dog or cat), particularly an animal of economic importance. Preferably, the body is human.

The invention also provides a method for managing pain, including neuropathic pain, including administering an effective amount of a composition according to the invention described above.

The present invention is particularly advantageous in reducing injury in the body, for example in the treatment of the heart in circumstances of myocardial infarction or heart attack, or during surgical procedures, for example during open-heart surgery.

The method of the present invention involves contacting a tissue with the composition according to the invention, for a time and under conditions sufficient for the tissue to be preconditioned, arrested, protected and/or preserved. The composition may be infused or administered as a bolus intravenous, intracoronary or any other suitable delivery route as pre-treatment for protection during a cardiac intervention such as open heart surgery (on-pump and off-pump), angioplasty (balloon and with stents or other vessel devices) and as with clot-busters (anti-clotting drug or agents).

The composition may be administered intravenously or be administered both intravenously and intraperitoneally or in special circumstances directly accessing a major artery such as the femoral artery or aorta in patients who have no pulse from massive exsanguination, or in the carotid artery or another artery during aortic dissection to protect the brain from hypoxia or ischemia. In one embodiment, the composition of the invention may be administered intravenously and intraperineally simultaneously, the perineum acting as, in effect, a reservoir of composition for the bloodstream as well as acting on organs in the vicinity with which it comes into contact. This is particularly suitable for a trauma victim, such as one suffering shock. Moreover, where the composition contains two or more components, these may be administered separately but simultaneously. Substantially simultaneous delivery of the component to the target site is desirable. This may be achieved by pre-mixing the components for administration as one composition, but that is not essential. The invention is directed towards the simultaneous increase in local concentration (for example an organ such as the heart) of the components of a composition according to the invention (for example, where a first component is (i) a potassium channel opener or agonist and/or an adenosine receptor agonist; and (ii) a local anaesthetic). One preferred form of the composition is a combination of adenosine and lignocaine.

The invention may be practised by administering the compound using a perfusion pump, often associated with a procedure known as "miniplegia" or "microplegia", in which minimal amount of actives are titrated by means of a finely adjustable pump directly via a catheter. In the invention, a protocol utilises miniplegia as described above, where micro amounts are titrated directly to the heart, using the patient's own oxygenated blood. The reference to a "setting" is a measure on the pump, such as a syringe pump, of the amount of substance being delivered directly to the organ, such as a heart.

The composition can also be infused or administered as a bolus intravenous, intracoronary or any other suitable delivery route for protection during cardiac intervention such as open heart surgery (on-pump and off-pump), angioplasty (balloon and with stents or other vessel devices) and as with clot-busters to protect and preserve the cells from injury.

The composition may also be infused or administered as a bolus intravenous, intracoronary or any other suitable delivery route for protection following a cardiac intervention such as open heart surgery (on-pump and off-pump), angioplasty (balloon and with stents or other vessel devices) and as with clot-busters to protect and preserve the cells from injury.

Accordingly, the tissue may be contacted by delivering the composition according to the invention intravenously to the tissue. This involves using blood as a vehicle for delivery to the tissue. In particular, the composition according to the invention may be used for blood cardioplegia. Alternatively, the composition may be administered directly as a bolus by a puncture (eg, by syringe) directly to the tissue or organ, particularly useful when blood flow to a tissue or organ is limiting. The composition for arresting, protecting and preserving a tissue may also be administered as an aerosol, powder, solution or paste via oral, skin or nasal routes.

Alternatively, the composition may be administered directly to the tissue, organ or cell or to exposed parts of the internal body to reduce injury. In particular, the composition according to the invention may be used for crystalloid cardioplegia.

The composition according to the invention may be delivered according to one of or a combination of the following delivery protocols: intermittent, continuous and one-shot.

Accordingly, in another aspect of the invention, there is provided a composition for arresting, protecting and preserving a tissue of a body upon administration of a single dose of the composition, the composition including a primary potassium channel opener or agonist and/or adenosine receptor agonist and a local anaesthetic. The invention also provides a method for arresting and protecting an tissue comprising administering as a single dose an effective amount of that composition.

In another aspect of the invention, there is provided a composition for arresting, protecting and preserving a tissue by intermittent administration of the composition, the composition including an effective amount of a primary potassium channel opener or agonist and/or adenosine receptor agonist and a local anaesthetic. A suitable administration schedule is a 2 minute induction dose every 20 minutes throughout the arrest period. The actual time periods can be adjusted based on observations by one skilled in the art administering the composition, and the animal/human model selected. The invention also provides a method for intermittently administering a composition for arresting, protecting and preserving a tissue.

The composition can of course also be used in continuous infusion with both normal and injured tissues or organs, such as heart tissue. Continuous infusion also includes static storage of the tissue, whereby the tissue is stored in a composition according to the invention, for example the tissue may be placed in a suitable container and immersed in a solution according to the invention for transporting donor tissues from a donor to recipient.

The dose and time intervals for each delivery protocol may be designed accordingly. For example, a composition according to the invention may be delivered as a one-shot to the tissue to initially arrest of the tissue. A further composition according to the invention may then be administered continuously to maintain the tissue in an arrested state. Yet a further composition according to the invention may be administered continuously to reperfuse the tissue or recover normal function.

As mentioned previously, the composition according to the invention may be used or contact the tissue at a temperature range selected from one of the following: from about 0° C. to about 5° C., from about 5° C. to about 20° C., from about 20° C. to about 32° C. and from about 32° C. to about 38° C. It is understood that "profound hypothermia" is used to describe a tissue at a temperature from about 0° C. to about 5° C. "Moderate hypothermia" is used to describe a tissue at a temperature from about 5° C. to about 20° C. "Mild hypothermia" is used to describe a tissue at a temperature from about 20° C. to about 32° C. "Normothermia" is used to describe a tissue at a temperature from about 32° C. to about 38° C., though the normal body temperature is around 37 to 38° C.

While it is possible for each component of the composition to contact the tissue alone, it is preferable that the components of the pharmaceutical composition be provided together with one or more pharmaceutically acceptable carriers, diluents, adjuvants and/or excipients. Each carrier, diluent, adjuvant and/or excipient must be pharmaceutically acceptable such that they are compatible with the components of the pharmaceutical composition and not harmful to the subject. Preferably, the pharmaceutical composition is prepared with liquid carriers, diluents, adjuvants and/or excipients.

The composition according to the invention may be suitable for administration to the tissue in liquid form, for example, solutions, syrups or suspensions, or alternatively they may be administered as a dry product for constitution with water or other suitable vehicle before use. Such liquid preparations may be prepared by conventional means.

The composition according to the invention may be suitable for topical administration to the tissue. Such preparation may be prepared by conventional means in the form of a cream, ointment, jelly, solution or suspension.

The composition may also be formulated as depot preparations. Such long acting formulations may be administered by implantation (eg, subcutaneously or intramuscularly) or by intramuscular injection. Thus, for example, the composition according to the invention may be formulated with suitable polymeric or hydrophobic materials (eg, as an emulsion in an acceptable oil or ion exchange resins, or as sparingly soluble derivatives, for example, as a sparingly soluble salt.

Accordingly, this aspect of the invention also provides a method for reducing injury, which includes providing the composition together with a pharmaceutically acceptable carrier, diluent, adjuvant and/or excipient. A preferred pharmaceutically acceptable carrier is a buffer having a pH of about 6 to about 9, preferably about 7, more preferably about 7.4 and/or low concentrations of potassium. For example, the composition has a total potassium concentration of up to about 10 mM, more preferably about 2 to about 8 mM, most preferably about 4 to about 6 mM. Suitable buffers include Krebs-Henseleit which generally contains 10 mM glucose, 117 mM NaCl, 5.9 mM KCl, 25 mM $NaHCO_3$, 1.2 mM $NaH_2PO_4$, 1.12 mM $MCaCl_2$ (free $Ca^{2+}$=1.07 mM) and 0.512 mM $MgCl_2$ (free $Mg^{2+}$=0.5 mM), Tyrodes solution which generally contains 10 mM glucose, 126 mM NaCl, 5.4 mM KCl, 1 mM $CaCl_2$, 1 mM $MgCl_2$, 0.33 mM $NaH_2PO_4$ and 10 mM HEPES (N-[2-hydroxyethyl]piperazine-N'-[2-ethane sulphonic acid], Fremes solution, Hartmanns solution which generally contains 129 NaCl, 5 mM KCl, 2 mM $CaCl_2$ and 29 mM lactate and Ringers-Lactate. Other naturally occurring buffering compounds that exist in muscle that could be also used in a suitable ionic environment are carnosine, histidine, anserine, ophidine and balenene, or their derivatives. One advantage of using low potassium is that it renders the present composition less injurious to the subject, in particular paediatric subjects such as neonates/infants. High potassium has been linked to an accumulation of calcium which may be associated with irregular heart beats during recovery, heart damage and cell swelling. Neonates/infants are even more susceptible than adults to high potassium damage during cardiac arrest. After surgery a neonate/infant's heart may not return to normal for many days, sometimes requiring intensive therapy or life support.

It is also advantageous to use carriers having low concentrations of magnesium, such as, for example up to about 2.5 mM, but it will be appreciated that high concentrations of magnesium, for example up to about 20 mM, may be used if desired without substantially affecting the activity of the composition.

In another embodiment of the present invention there is provided use of a composition according to the present invention for reducing injury.

Preferably the composition is aerated before and/or during administration or contact with the tissue.

IN THE FIGURES

FIG. 1 shows ECG trace of rat heart (A) prior to hemorrhagic shock (B) during shock and (C) after bolus administration of 0.5 ml Adenosine/Lignocaine solution directly into the heart of the rat.

FIG. 2 shows in more detail the ECG trace of the rat heart from FIG. 1 (A) during hemorrhagic shock and after injection of Adenosine/Lignocaine solution directly into the heart of the rat and (B) 10 seconds following injection. The time of injection of the solution is indicated by the arrow (I). Arrow (II) denotes the proposed time at which further treatment may be required.

Figure 8:
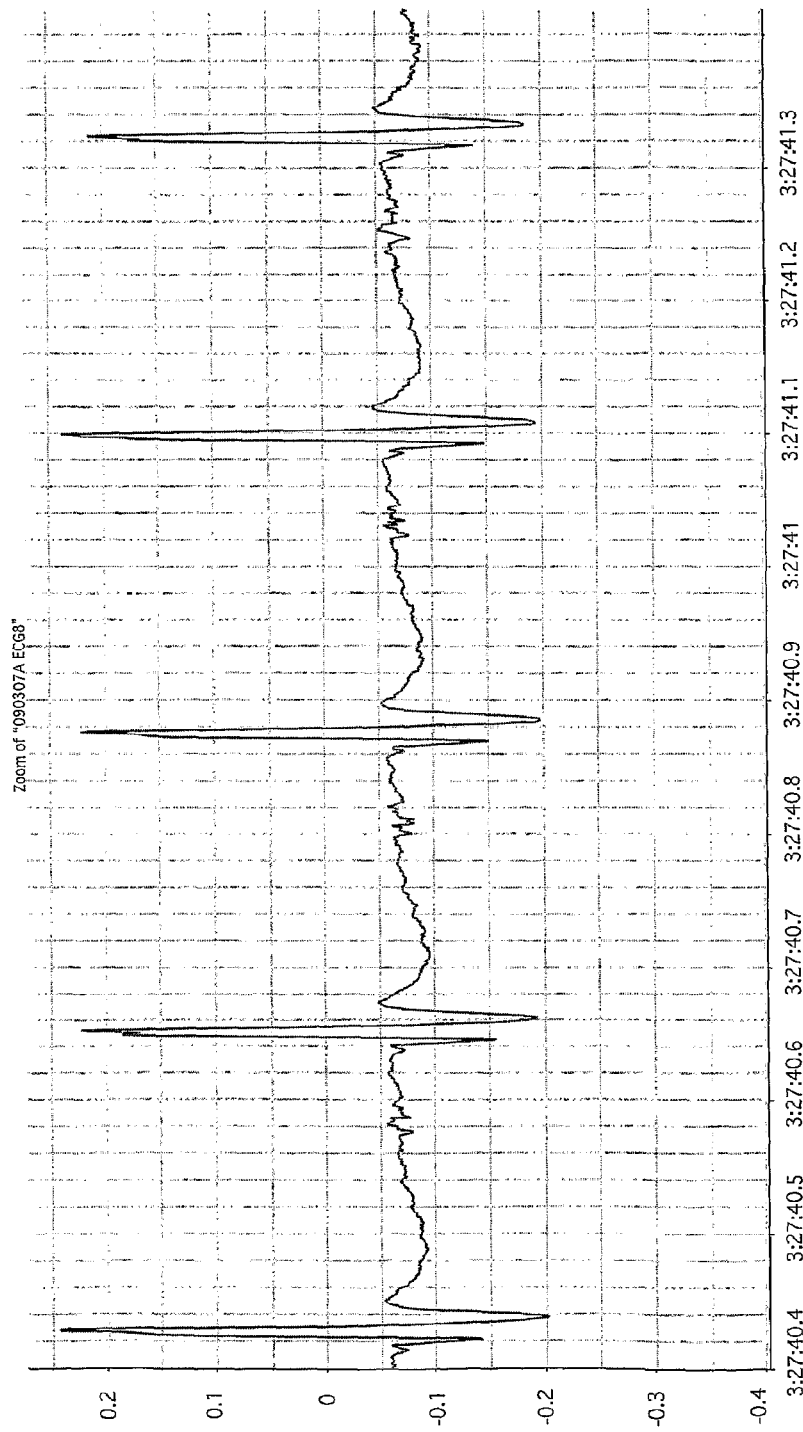

FIG. 8 shows an ECG trace of rat heart 10 mins after bolus administration of ALM (Adenosine; Lignocaine; Magnesium)

Figure 9:
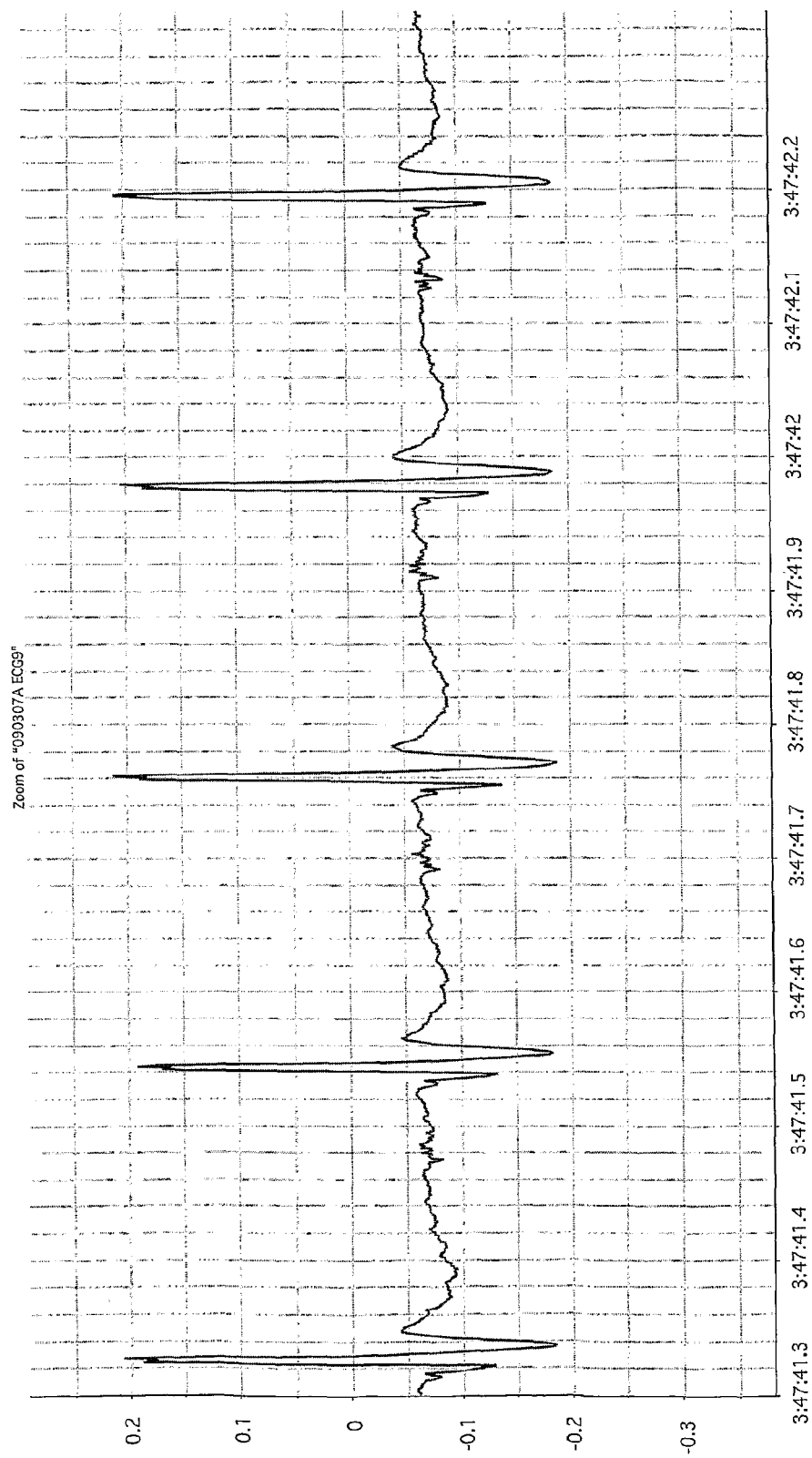
Figure 10:
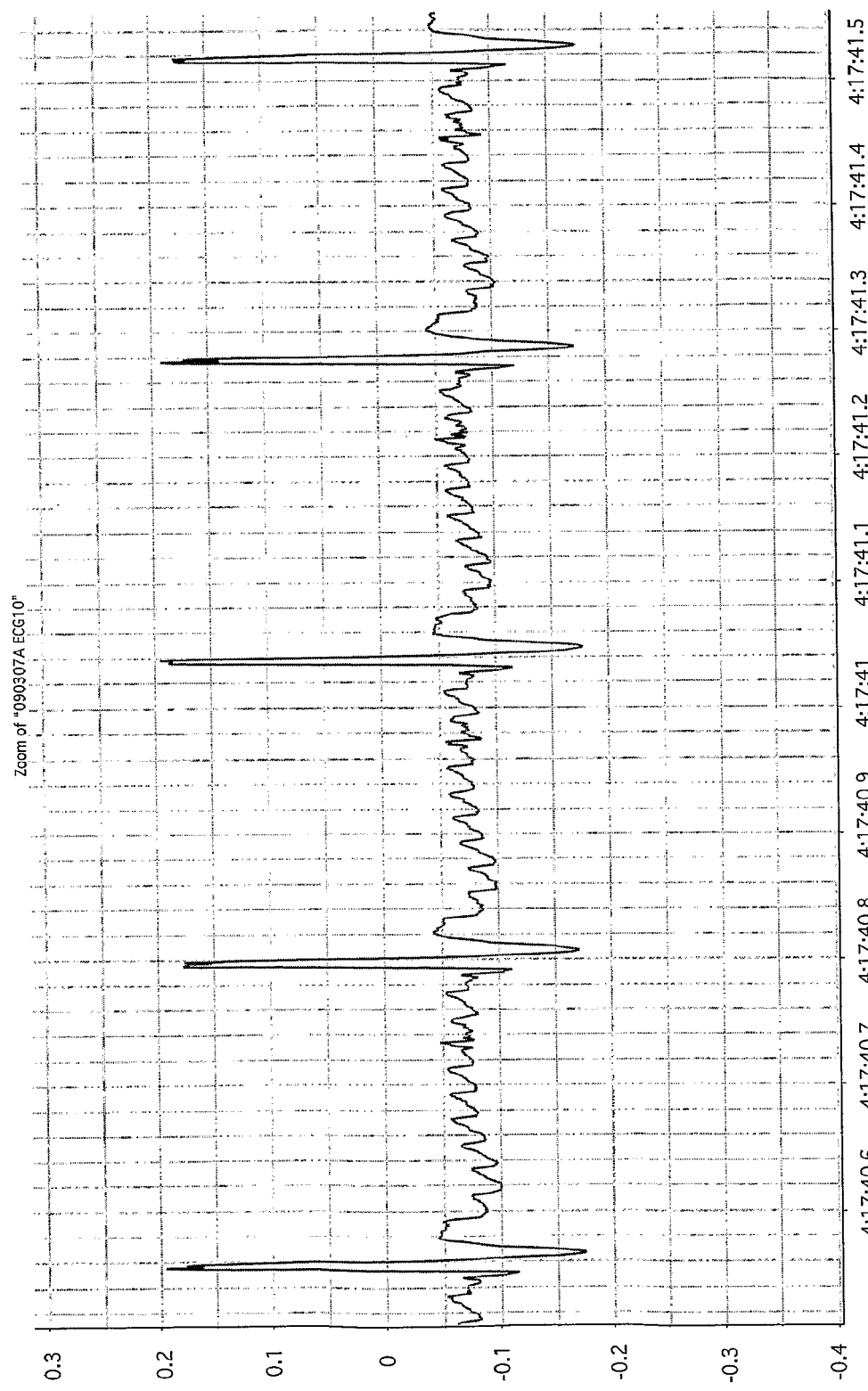
Figure 11:
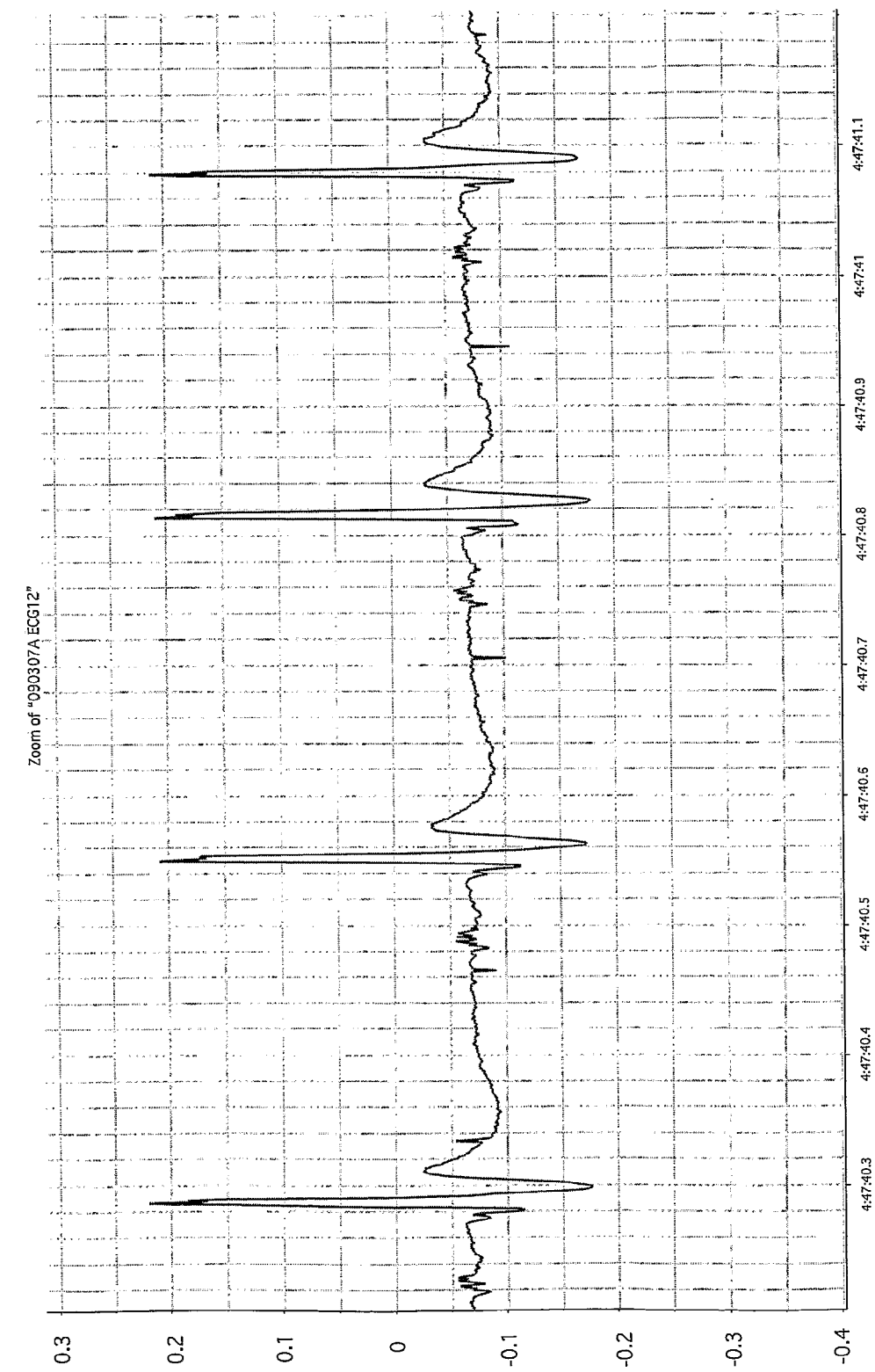

FIG. 9 shows an ECG trace of rat heart 30 mins after bolus administration of ALM FIG. 10 shows an ECG trace of rat heart 60 mins after bolus administration of ALM FIG. 11 shows an ECG trace of rat heart 90 mins after bolus administration of ALM FIG. 12 shows ECG trace of rat heart (A) prior to Hemorrhagic shock (45% blood loss); (B) 60 min following hemorrhagic shock and intravenous administration of Adenosine/Lignocaine resuscitation fluid (C) 180 mins following hemorrhagic shock and intravenous administration of Adenosine/Lignocaine resuscitation fluid.

FIG. 13 shows in more detail the ECG monitoring of the rat heart from FIG. 12 following hemorrhagic shock (A) after administration of 0.5 ml 7.5% saline and (B) after administration of 0.5 ml Adenosine/Lignocaine resuscitation fluid.

EXAMPLES

The following are provided as non-limiting examples of suitable compositions of the invention for the purpose of illustrating the invention.

Animals and Reagents:

Male Sprague Dawley rats (300-350 g) from the James Cook University Breeding Colony are fed ad libitum and housed in a 12-hour light/dark cycle. On the day of the experiment rats are anesthetized with an intraperitoneal injection of Nembutal (Sodium Thiopentone (Thiobarb); 100 mg/kg) and the anaesthetic administered as required throughout the protocol. Animals are treated in accordance with the Guide for the Care and Use of Laboratory Animals published by the US national Institutes of Health (NIH Publication No. 85-23, revised 1996).

Lignocaine hydrochloride is sourced as a 2% solution (ilium) from the local Pharmaceutical Suppliers (Lyppard, Queensland). All other chemicals, including adenosine (A9251>99% purity), are sourced from Sigma Aldrich (Castle Hill, NSW).

Surgical Protocol:

Anesthetized non-heparinized animals are positioned in a specially designed plexiglass cradle. A tracheotomy is performed and the animals artificially ventilated at 75-80 strokes per min on humidified room air using a Harvard Small Animal Ventilator (Harvard Apparatus, Mass., USA) to maintain blood $pO_2$, $pCO_2$ and pH in the normal physiological range (Ciba-Corning 865 blood gas analyzer).

Body temperature is maintained at 37° C. (Homeothermic Blanket Control Unit, Harvard Apparatus, Mass., USA). A rectal probe is used to measure core body temperature. The left femoral vein is cannulated using PE-50 tubing for drug withdrawal and infusions while the right femoral artery is cannulated for blood collection and blood pressure monitoring (UFI 1050 BP coupled to a MacLab). All cannulae contains heparinized saline (100 U/ml saline). Electrocardiogram (ECG) leads are implanted subcutaneously in a lead II ECG configuration. Rats are stabilized for 15-20 minutes prior to blood withdrawal. Any animal that had dysrhythmias and/or a sustained fall in mean arterial blood pressure below 80 mmHg are discarded from the study.

Hemorrhagic Shock:

The following examples are directed to hemorrhagic shock. Hemorrhagic shock is induced by withdrawing blood from the femoral vein or artery at a rate of 3 ml/100 g rat over 10 min to lower the mean arterial blood pressure (MAP) to between 30 and 35 mmHg. For a 300 g rat the total blood volume is estimated to be 0.06×300+0.77=18.77 ml. Withdrawing 9 ml over a 10 min period (0.9 ml/min) would result in a blood volume loss of about 50%.

For experiments involving 60% blood loss, 112 ml is withdrawn over a 20 min period (0.56 ml/minute). The withdrawn blood is then kept in a glass syringe that had been pre-rinsed with 0.02 ml heparin (1000 U/ml). MAP is maintained between 30 and 35 mmHg by blood withdrawal or re-infusion as needed for three shock periods (1 hr or 2 hr or 3 hr, n=6 each shock period) prior to crystalloid resuscitation.

At the end of the hemorrhagic shock period, rats receive the resuscitation solutions outlined in each of the experiments below to achieve a MAP of 80-90 mmHg (Note: in some experiments the MAP is kept low to around 40-60 mmHg from the hypotensive effect of adenosine and lignocaine to better balance the body's energy supply and energy demand index).

Survival is assessed from haemodynamics (MAP, Heart rate) and ECG following resuscitation, which is monitored for up to 6 hours. Death is recognized by the disappearance of MAP, HR and loss of sinus rhythm, and verified by examination of the heart.

Example 1

Intravenous Administration of Adenosine/Lignocaine Resuscitation Solution

Rats are randomly assigned into 4 groups (10 rats per group, n=10) and prepared and subjected to hemorrhagic shock as described above. After 60 min shock, the rats are resuscitated as follows:

1.1 Large Volume Fluids: Slow Intravenous Fluid Augmentation

Group 1: 10 minute infusion of 9 ml/100 g of 0.9% NaCl (3 times the volume of shed blood) containing 10 uM adenosine (or adenosine analogues or agonists) and 30 microM lignocaine.

Group 2: 10 minute infusion of 9 ml/100 g of 0.9% NaCl 1.2 Small Volume Fluids: Rapid Intravenous Fluid Augmentation Group 3: bolus of 0.4 ml/100 g (1.2 ml for a 300 g rat) of 7.5% NaCl/6% dextran-70 containing adenosine (or adenosine analogues or agonists) and lidocainelignocaine Group 4: bolus of 0.4 ml/100 g (1.2 ml for a 300 g rat) of 7.5% NaCl/6% dextran-70.

Example 2

Intraperitoneal Support of Intravenous Fluid Augmentation

Rats are randomly assigned into the same number of groups as in Example 1 above with 10 rats in each group (n=10). Rats are prepared and subjected to hemorrhagic shock as described above. After 60 min shock, the rats are resuscitated as described in Example 1 above plus an intraperitoneal bolus of 5 ml of 0.2 mM adenosine (or adenosine analogues or agonists) and 0.5 mM lignocaine.

Example 3

Slow Intravenous Administration of Resuscitation Solution Containing Adenosine/Lignocaine Plus Additional Component Rats are randomly assigned into 18 groups with 10 rats in each group (n=10). Rats are prepared and subjected to hemorrhagic shock as described above. After 60 min shock, the rats are resuscitated using a 10 minute infusion of 9 ml (3 times the volume of shed blood) of the following solutions:

Group 1: 10 uM adenosine (or adenosine analogues or agonists) and 30 uM lignocaine plus 50 uM diazoxide Group 2: 10 uM adenosine (or adenosine analogues or agonists) and 30 uM lignocaine plus 1 uM dipyridamole (MW 504.6), Group 3: 10 uM adenosine (or adenosine analogues or agonists) and 30 uM lignocaine plus 1 uM [D-Pen 2, 5] enkephalin (DPDPE)

Group 4: 10 uM adenosine (or adenosine analogues or agonists) and 30 uM lignocaine plus high magnesium sulphate (5 mM), Group 5: 10 uM adenosine (or adenosine analogues or agonists) and 30 uM lignocaine plus low magnesium sulphate (0.5 mM)

Group 6: 10 uM adenosine (or adenosine analogues or agonists) and 30 uM lignocaine plus substrates/fuels (10 mM glucose, 1 mM pyruvate)

Group 7: 10 uM adenosine (or adenosine analogues or agonists) and 30 uM lignocaine plus antioxidant (1 mM allopurinol)

Group 8: 10 uM adenosine (or adenosine analogues or agonists) and 30 uM lignocaine plus 10 uM amiloride Group 9: 10 uM adenosine (or adenosine analogues or agonists) and 30 uM lignocaine plus 50-100 mM raffinose.

Group 10: 10 uM adenosine (or adenosine analogues or agonists) and 30 uM lignocaine plus 50-100 mM sucrose.

Group 11: 10 uM adenosine (or adenosine analogues or agonists) and 30 uM lignocaine plus 50-100 mM pentastarch.

Group 12: 10 uM adenosine (or adenosine analogues or agonists) and 30 uM lignocaine plus Dextran-30 at physiological pH.

Group 13: 10 uM adenosine (or adenosine analogues or agonists) and 30 uM lignocaine plus Dextran-40 at physiological pH.

Group 14: 10 uM adenosine (or adenosine analogues or agonists) and 30 uM lignocaine plus Dextran-50 at physiological pH.

Group 15: 10 uM adenosine (or adenosine analogues or agonists) and 30 uM lignocaine plus Dextran-60 at physiological pH.

Group 16: 10 uM adenosine (or adenosine analogues or agonists) and 30 uM lignocaine plus hydroxyethyl starch at physiological pH.

Group 17: 10 uM adenosine (or adenosine analogues or agonists) and 30 uM lignocaine plus modified fluid gelatin at physiological pH.

Group 18: 10 uM adenosine (or adenosine analogues or agonists) and 30 uM lignocaine plus 50 uM diazoxide, 1 uM dipyridamole (MW 504.6), 1 uM [D-Pen 2, 5] enkephalin (DPDPE), high and low magnesium sulphate (5 and 0.5 mM), substrates/fuels (10 mM glucose, 1 mM pyruvate), antioxidant (1 mM allopurinol), NaH inhibitor (10 uM amiloride), 50-100 mM sucrose and Dextran-40 at physiological pH.

Example 4

Rapid Intravenous Administration of Resuscitation Solution Containing Adenosine/Lignocaine Plus Additional Component Rats are randomly assigned into 16 groups (n=10) and prepared and subjected to hemorrhagic shock as described above. After 60 min shock, the rats are resuscitated using a bolus of 0.4 ml/100 g (1.2 ml for a 300 g rat) of the following solutions:

Group 1: 7.5% NaCl/6% dextran-70 containing 0.2 mM adenosine (or adenosine analogues or agonists) and 0.5 mM lignocaine plus 50 uM nicorandil.

Group 2: 7.5% NaCl/6% dextran-70 containing 0.2 mM adenosine (or adenosine analogues or agonists) and 0.5 mM lignocaine plus 1 uM dipyridamole (MW 504.6).

Group 3: 7.5% NaCl/6% dextran-70 containing 0.2 mM adenosine (or adenosine analogues or agonists) and 0.5 mM lignocaine plus 1 uM [D-Pen 2, 5] enkephalin (DPDPE).

Group 4: 7.5% NaCl/6% dextran-70 containing 0.2 mM adenosine (or adenosine analogues or agonists) and 0.5 mM lignocaine plus high magnesium sulphate (5 mM).

Group 5: 7.5% NaCl/6% dextran-70 containing 0.2 mM adenosine (or adenosine analogues or agonists) and 0.5 mM lignocaine plus low magnesium sulphate (0.5 mM).

Group 6: NaCl/6% dextran-70 containing 0.2 mM adenosine (or adenosine analogues or agonists) and 0.5 mM lignocaine plus substrates/fuels (10 mM glucose, 1 mM pyruvate).

Group 7: NaCl/6% dextran-70 containing 0.2 mM adenosine (or adenosine analogues or agonists) and 0.5 mM lignocaine plus 1 mM allopurinol.

Group 8: NaCl/6% dextran-70 containing 0.2 mM adenosine (or adenosine analogues or agonists) and 0.5 mM lignocaine plus 10 uM amiloride.

Group 9: NaCl/6% dextran-70 containing 0.2 mM adenosine (or adenosine analogues or agonists) and 0.5 mM lignocaine plus impermeants (50-100 mM raffinose, sucrose, pentastarch).

Group 10: 10 uM adenosine (or adenosine analogues or agonists) and 30 uM lignocaine plus 50-100 mM sucrose.

Group 11: 10 uM adenosine (or adenosine analogues or agonists) and 30 uM lignocaine plus 50-100 mM pentastarch.

Group 12: NaCl/6% dextran-70 containing 0.2 mM adenosine (or adenosine analogues or agonists) and 0.5 mM lignocaine plus colloids (Dextran-30, 40, 50 and 60, hydroxyethyl starch and a modified fluid gelatin) at physiological pH.

Group 13: 10 uM adenosine (or adenosine analogues or agonists) and 30 uM lignocaine plus Dextran-40 at physiological pH.

Group 14: 10 uM adenosine (or adenosine analogues or agonists) and 30 uM lignocaine plus Dextran-50 at physiological pH.

Group 15: 10 uM adenosine (or adenosine analogues or agonists) and 30 uM lignocaine plus Dextran-60 at physiological pH.

Group 16: 10 uM adenosine (or adenosine analogues or agonists) and 30 uM lignocaine plus 50 uM diazoxide, 1 uM dipyridamole (MW 504.6), 1 uM [D-Pen 2, 5] enkephalin (DPDPE), high and low magnesium sulphate (5 and 0.5 mM), substrates/fuels (10 mM glucose, 1 mM pyruvate), antioxidant (1 mM allopurinol), NaH inhibitor (10 uM amiloride), impermeants (50-100 mM sucrose and Dextran-40 at physiological pH.

Example 5

Intraperitoneal Support of Slow Intravenous Fluid Augmentation

Rats are prepared, subjected to hemorrhagic shock and resuscitated as described in Example 3 together with an intraperitoneal bolus of 5 ml of 0.2 mM adenosine (or adenosine analogues or agonists) and 0.5 mM lignocaine.

Example 6

Intraperitoneal Support of Rapid Intravenous Fluid Augmentation

Rats are prepared, subjected to hemorrhagic shock and resuscitated as described in Example 4 together with an intraperitoneal bolus of 5 ml of 0.2 mM adenosine (or adenosine analogues or agonists) and 0.5 mM lignocaine.

Example 7

The Effect of Lowering Body Temperature on the Different Resuscitation Strategies The above examples (examples 1 to 6) are repeated at 35, 33, 20, and 4° C. The formulations are equilibrated with air or, if found to be efficacious in preliminary testings, may be aerated or have an oxygen containing perfluorocarbon based, or haemoglobin based substitute present or blood, a blood product or artificial blood. Components may be added to mimic human blood's oxygen transport ability such as Hemopure™ Gelenpol™, Oxygent™, PolyHeme™.

Example 8

Treating VF During Cardiac Surgery (On-Pump)

Different ways of utilising the invention are illustrated in 5 groups labelled A-E of patients as follows:

Group A: Patients receiving standard local hospital hypothermic (cardioplegic delivery temp 10° C.) high potassium cardioplegia plus potassium "hot shot" (arresting dose).

Group B: Patients receiving standard local hospital warm (cardioplegic delivery temp 33° C.) high potassium cardioplegia plus potassium "hot shot" (arresting dose).

Group C: Patients receiving hypothermic adenosine and lignocaine (cardioplegic delivery temp 10° C.) cardioplegia (normal potassium 5 mM) plus HiberStart (non arresting dose) to reanimate the heart.

Group D: Patients receiving warm adenosine and lignocaine (cardioplegic delivery temp 33° C.) cardioplegia (normal potassium 5 mM) plus a non-arresting dose of adenosine and lignocaine to reanimate the heart. L or ALM in Group B and D to study the effect of pretreating the heart before arrest.

Group E: Hearts are pretreated/preconditioned using a solution of adenosine and lignocaine with or without magnesium (1.0-20 mM) and then the heart is arrested and reanimated as in Group D. Hearts may also be postconditioned following reperfusion in combination with an arresting or non-arresting dose of adenosine and lignocaine solution with or without magnesium (1.0-20 mM).

The cardioplegia composition and protocol for human patients in Groups A-E are as follows.

1) Composition of high potassium cardioplegia solution for Groups A & B:

Induction cardioplegia 20 mM K+ solution (final): BAXTER (Code AHK5524). Each 500 ml contains: Sodium Chloride BP 4.5 g, Potassium Chloride BP 3 g, Magnesium Chloride BP 2.6 g, Lignocaine HCl BP 250 mg. Before use, Sodium Bicarbonate (25 mmol/500 ml) and monosodium Aspartate (14 mmol/500 ml) added, with pH ~3.7 and osmolality ~547 mOsm.

Maintenance cardioplegia 9 mM K+ solution (final): BAXTER (Code AHK5525). Each 500 nil contains: Sodium Chloride BP 4.5 g, Potassium Chloride BP 1 g, Magnesium Chloride BP 2.6 g. Before use, Sodium Bicarbonate (25 mmol/500 ml) and monosodium Aspartate (14 mmol/500 ml) added, with pH ~3.7 and osmolality ~547 mOsm.

During reanimation, the arrest solution is same as K+ maintenance but the myocardial heart temperature during induction, maintenance and terminal shot is 32 to 38° C. The heart remains arrested at this time.

2) Composition of adenosine and lignocaine ("AL") cardioplegia solution for Groups C, D and E:

The optimal concentrations of AL will be found from a dose response curve. A is about 0.2 to 2 mM and L is about 0.2 to 4 mM. These concentrations have been shown to be safe in humans. Magnesium may be 1.0-20 mM. The arresting induction is at higher levels of A and L and maintenance dose may be lower e.g. at half the concentration to induce arrest. Final K+ infused into the heart around final 3-6 mM (normally around 5 mM). The temperature profiles of the induction and maintenance volumes are similar to the temperature protocol described for Group A & B.

During reanimation, the adenosine and lignocaine solution does not arrest the heart but protects and preserves the heart during reanimation. It may beat prior to release of cross clamp. Concentrations of AL and M are A 10-40 micromolar, L: 30-50 micromolar and magnesium sulphate of 10-20 mM and the temperatures 32 to 38° C.

3) Composition of cardioplegia solution for Group E: Same as Group D above but with pretreatment/preconditioning doses of adenosine and lignocaine concentrations with or without magnesium sulphate during reperfusion or during postconditioning+adenosine and lignocaine concentrations with or without magnesium sulphate.

If a MPS Quest cardioplegia perfusion pump system using microplegia (1 part and 9 parts of blood) is available, the following adenosine and lignocaine concentrations with and without magnesium can be used to test the arresting and maintenance doses to be used in the study.

Inducing Arrest:
54 mg A+132 mg L in the 50 ml cassette (0.5 mM and 1.0 mM final concs in the blood hitting the heart). The studies by Mentzer et al have shown that 2 mM ado is safe in cardioplegia in humans.

Maintenance:
26 mg A+66 mg L in the 50 ml cassette (0.2 mM ado and 0.5 mM lido).

Reanimation:
AL plus Mg++(also called "ALM") used at 10 uM A, 30 uM L and 16 mM MgSO4 cassette.

Treatment of Patients Enrolled in the Study Who Suddenly Experience Life-Threatening Arrhythmias (Ventricular Tachycardia and/or Fibrillation):

If a patient has a sudden cardiac event such as a heart attack and the heart's beating rhythm abruptly changes (eg. converts to ventricular tachycardia or ventricular fibrillation) in hospital prior to or after surgery, a bolus dose of adenosine and lignocaine with or without magnesium is given intravenously (or intracardiac) to resuscitate the heart prior to using the defibrillator (if a defibrillator is required). If the patient has life-threatening severe arrhythmias (ventricular fibrillation or ventricular tachycardia) while in the operating room or intensive care ward a bolus dose of adenosine and lignocaine with or without magnesium is given intravenously (or intracardiac) to resuscitate the heart prior to using the defibrillator (if a defibrillator is required).

Example 9

Protecting Against Heart Arrhythmias and Treating VF During and Following Off-Pump Cardiac Surgery in Humans Preclinical studies showed that an intravenous infusion adenosine and lignocaine with or without magnesium is highly protective to the heart during myocardial ischemia in the in vivo rat and canine model. A three-pronged attack is envisaged: 1) maintain the resting cell's membrane potential or voltage during times of ischemia, 2) down-regulate metabolism, and 3) blunt the inflammatory and hypercoagulable responses. Defending the membrane potential close to the resting polarized state reduces ionic and metabolic imbalances; down regulating the cell's metabolism lowers the demand, and attenuating the inflammatory and blood clotting responses, reduces further damage during reperfusion. Targeting all three provides greater protection from life-threatening arrhythmias and other ischemia-related damage to both the myocardium and coronary vasculature. (Canyon, S and Dobson, G P 2004 "Protection against ventricular arrhythmias and cardiac death using adenosine and lignocaine during regional ischemia in the in vivo rat", American Journal of Physiology, 287: H1286-H1295).

Intravenous infusion of adenosine and lignocaine using a lower lignocaine dose was highly cardioprotective. Adenosine and lignocaine with lower lignocaine concentrations resulted in no deaths, virtually abolished severe arrhythmias and decreased infarct size in the rat model of acute ischemia.

A composition of the invention administered in patients undergoing beating-heart surgery will be via an intravenous route through a dedicated port on a central venous line. The composition comprises 305 μg/kg/min adenosine plus 60 μg/kg/min lignocaine and is administered intravenously 5 min before and during each coronary artery anastomosis. A single lignocaine bolus (1 mg/kg) is injected for 3 min immediately before the first administration of the AL solution.

For example, for a 70 kg patient: 0.305×70=21.35 mg adenosine per min and 0.06×75=4.2 mg Lignocaine per minute is administered. Prior to adenosine and lignocaine solution 70 mg of lignocaine-HCL is given as a bolus.

Limits of infusion: If constantly infused for 1 hour: total amount of adenosine and lignocaine administered if constantly infused for 60 min equates to 60×21.35=1281 mg adenosine and 60×4.2 mg=252 mg lignocaine (+70 mg bolus=322 mg). Half-life of adenosine is 4 to 10 seconds in human blood. We envisage a total adenosine and lignocaine infusion time of 30 min to complete 3 anastomoses, average time 10 min each Another example is at an infusion rate of 0.3 mg/kg/min in a 70 Kg subject, we need to infuse 21 mg/min. If the infusion mixture is 300 mg in 540 ml (Ie 0.56 mg/ml), for this subject we need to run at 37.5 ml/min or 2.250 l/hr.
Pre-Clinical Studies:

In a rat study, 0.0567 g Adenosine and 0.565 ml lignocaine-HCl (20 mg/ml) to 10 ml saline were infused IV 1 ml/hour into a 300 g rat. So for our 35 min pretreatment and ischemia period we only use 35/60×1 ml=0.58 ml of 10 ml solution we make.

Start with a 1 mg/kg bolus of lido-HCl followed by a infusion of the adenosine and lignocaine solution. The adenosine infusion rate translates to 0.311 mg/kg/min (ie 1 ml/hour infusion rate or 1/60 ml per min or 1/60×5.6 mg/ml (in 10 ml we make)×1000/300 (for 300 g rat)=0.311 mg/kg/min). The lignocaine infusion rate translates to 0.0627 mg/kg/min (ie 1/60×1.13 mg/ml (in 10 ml we make)×1000/300=0.0627 mg/kg/min).
Human Study:

For the 70 kg human study make a 500 ml (50 times) bag with 0.0567×70/0.3=13.23 g Adenosine and 0.565×70/0.3=132 ml lignocaine-HCl (20 mg/ml) and deliver the solution at an IV rate of 50 ml per hour. This delivers the same amount of drug per unit mass. For 5 anastomoses and pre-treating each for 5 min before and say each anastomoses takes 20 min (MAX) then that is 5×(20+5) min=125 min (MAX)

Therefore at 50 ml/hour, infuse about 50/60×125=104 ml per patient for 125 min total anastomoses time. Example of IV infusion Protocol: To make 300 ml (not 500 ml) it would be 3/5×13.23 g Ado and 3/5×132 ml lignocaine HCl and infuse iv at 50 ml per hour. For a 70 kg human, Adenosine infusion rate: 0.311 mg/kg/min or 21.77 mg/human patient/min and Lignocaine-HCl infusion rate: 0.0627 mg/kg/min or 4.39 mg/human patient/min.

6 min before first anastomoses inject bolus of lignocaine (1 mg/kg) followed by AL solution for 5 min. Stop infusion after each anastomoses has been completed. When the surgeon is ready for the next anastomoses, begin infusion IV 5 min before. And repeat the same for each anastomoses.
Timing of Administration:

5 min before surgery, continued during regional ischaemia and stop following completion of the anastomosis.

Example 10

Treating VF and Using Adenosine and Lignocaine with and without Magnesium During 'On-Pump' Cardiac Surgery Currently over 99% of all surgical cardioplegia solutions contain high potassium (15-20 mM), which arrests the heart unnaturally by depolarising the membrane potential from −83 mV to about −50 mV. At these depolarizing potentials sodium can increase inside cells via the Na$^+$ 'window' current, which, in turn, leads to a rise in intracellular Ca$^{2+}$ through the reversal of the Na/Ca$^{2+}$ exchanger. The potentially damaging accumulation of Ca$^{2+}$ may occur during the cardioplegic period (induction and maintenance phase) and/or during the reanimation-reperfusion phase following arrest. High potassium-linked Ca$^{2+}$ loading has been linked to myocardial stunning, ventricular arrhythmias, ischaemic injury, microvascular injury, tissue oedema, free radical production and functional loss during the reperfusion period. Depolarising potassium is also a potent coronary vasoconstrictor and this may further compound any antecedent vulnerability of the heart to injury during cardioplegic arrest, maintenance and recovery.

Example 11

Treatment for Life-Threatening Ventricular Tachycardia and/or Fibrillation

A large number of sudden deaths are caused by acute ventricular tachyarrhythmias (ventricular tachycardia and/or fibrillation) and often triggered by acute coronary events in association with heart disease or in persons without known cardiac disease. The most common pathophysiological cascade in the appearance of fatal arrhythmias is that ventricular tachycardia degenerates to ventricular fibrillation and later to asystole or cardiac arrest and death. If a patient experiences a sudden cardiac event such as a heart attack and the heart's beating rhythm abruptly changes (eg. converts to ventricular tachycardia or ventricular fibrillation) in hospital prior to or after surgery, a bolus dose of adenosine and lignocaine with or without magnesium is given intravenously (or intracardiac) to resuscitate the heart prior to using the defibrillator (if a defibrillator is required). If the patient has life-threatening severe arrhythmias (ventricular fibrillation or ventricular tachycardia) while in the operating room or intensive care ward a bolus dose of adenosine and lignocaine with or without magnesium is given intravenously (or intracardiac) to resuscitate the heart prior to using the defibrillator (if a defibrillator is required).

The method to treat human subjects suffering from an unexpected cardiac event leading to irregular arrhythmias such as acute ventricular tachyarrhythmias and pharmacologically convert the heart to normal beating or sinus rhythm using adenosine and lignocaine with and without magnesium is as follows.

Hearts will be arrested using a microplegia method of hyperkalemic cardioplegia induction, maintenance and reanimation. Microplegia is an alternative method to infusing the myocardium with the standard 4:1 mixture of blood and cardioplegia to arrest the heart. Microplegia aims to induce and maintain aerobic arrest of the heart by delivering continuous oxygen rich blood coupled with micro titrations of potassium (arrest) and magnesium (additive) solutions. Aerobic arrest offers superior myocardial protection over that of standard 4:1 cardioplegia regimens and tighter control of blood glucose levels. Most importantly, with the addition of adenosine and lignocaine to the additive mixture, an even higher level of myocardial protection is expected to produce long-lasting perioperative benefits to the patient. The composition of adenosine and lignocaine makes cardiac surgery safer for the patient and more predictable for the surgeon.

This example compares potassium arrest induction and maintenance cardioplegia and a non-arrest reanimation solution using adenosine and lignocaine with and without magnesium. The maintenance solution may also contain adenosine and lignocaine but the principal mode of arrest in these groups will be high potassium. In another separate group, adenosine and lignocaine will be the principal mode of arrest, protection and preservation for induction and maintenance cardioplegia and reanimation will be compared to the potassium arrest, maintenance and reanimation groups. In cases, where the heart does not return to proper function after reanimation a bolus of adenosine and lignocaine with or without magnesium will be given in the perfusion line (or intracardiac) to resuscitate the heart prior to using the defibrillator (if a defibrillator is required).
Microplegia Delivery Protocol:

Patients scheduled for on-pump coronary artery bypass surgery, valve surgery or combined procedure; or re-operations of the same. Patients receive anaesthesia and cardiac surgery as per usual practice. The use of inotropes, vasoconstrictors is "protocol-driven" and based on criteria for use as agreed upon by the surgical/anaesthesia team. The following are cassette formulations designed for arrest, maintenance and reanimation of the heart in, for example, the Quest MPS® Microplegia System.

The Arrest Cassette:
1. 80 mEq of undiluted Potassium=40 mL.
2. High Setting: 25 mEq/L.
3. Low Setting: 10 mEq/L.

The Additive Cassette:
1. 12 mg Adenosine=4 mL.
2. 25 mg Lignocaine=1 mL.
3. 5 gm Magnesium Sulfate=10 mL.
4. 30 mL crystalloid prime (e.g. Plasmalyte).
5. Total Volume in Additive Cassette: 45 mL.
6. Additive Setting: 10 mL/L.

Upon heparinization, fill the ice reservoir to the top with ice. Refill reservoir as needed. Delivery temp ~8-12° C. Temperature setting for warm induction is 37 degrees.

1. Cardiac arrest is induced with normothermic hyperkalemic blood microplegia. Patients receive hyperkalemic blood microplegia with 1) adenosine and lignocaine and magnesium in the additive cassette as a pre-treatment regimen, 2) lower adenosine and lignocaine, magnesium and potassium levels during the delivery of maintenance cardioplegia, and 3) adenosine and lignocaine and magnesium without potassium as a warm reperfusion dose.
2. Upon application of the cross clamp for the induction phase, ramp up flow for antegrade quickly to 500 mL/min then immediately back down to 320 to 350 mL/min. This ensures closure of the aortic valve. A total of 700-1000 mL of warm blood cardioplegia with high (25 mEq) potassium is delivered in antegrade fashion. Upon achieving quiescence, switch to retrograde warm and deliver an additional 700 mL.
3. Switch the water bath to cold (4° C.; the delivery temperature is between 8 and 12° C.). Lower additive setting (saline or adenocaine) to 2 mL/L. Whenever possible, continue microplegia administration throughout the case.
4. When approaching the last ten minutes of cross clamp, preparations are made to deliver the warm reperfusion dose by switching the water bath to warm at 37-38 degrees.
5. Warm reperfusion dose: Start or continue delivery of warm blood with or without adenosine and lignocaine in retrograde fashion. Administer warm retrograde microplegia until grafts are completed and then switch to antegrade delivery mode. This facilitates de-airing of the grafts and allow the right side of the heart to be perfused. The antegrade modality of delivery ensures that microplegia is adequately delivered and distributed to the myocardium (when all grafts are completed). After three to five minutes in the antegrade mode, when de-airing is complete, continue with warm antegrade until remaining volume in additive cassette is given (usually 500-1000 cc).

A number of end points and measurable outcomes are assessed for comparison:
1. Patient demographics and history including: age, gender, co-morbidities (i.e. diabetes, hypercholesterolemia, hypertension, smoking, COPD, renal failure).
2. Pre-op data including: diagnosis, BSA and lab values (BUN/Creatinine, INR, PT/PTT, INR, PLT. count, post-heparin glucose and HCT), number of intended grafts.
3. Intra-op data including:
   1) number of vessels bypassed
   2) length of bypass (start to wean time)
   3) cross-clamp time
   4) blood glucose levels, insulin dosing
   5) HCT during the case
   6) total volume of microplegia delivered, amount of additive and potassium given
   7) duration of warm reperfusion dose, volume of hotshot
   8) number of breakthrough events (re-animation of myocardium) and potassium level needed to re-arrest
   9) pre- and post-CPB ejection fraction
   10) return to sinus rhythm before cross-clamp removal (yes/no); incidence of ventricular fibrillation
   11) Incidence of atrial fibrillation
   12) Need for cardioversion (number of shocks, energy level of each)
   13) Need for any rearrest protocol [additional or extended hotshot (at surgeon's request), need to convert to adenocaine at the point of hotshot]
   14) Urine output from O.R. until first 24 hours post-op.
   15) Blood product usage (FFP, Platelets, RBCs and Cryo.) from O.R. until discharge.
   16) Blood glucose levels and insulin dosing (first 24 hours post-op).
   17) Plasma Troponin I levels at 6, 12, 24 hours post-op.
   18) Clinical evidence of acute myocardial infarction (Q-waves, arrythmias).
4. Time on ventilator (time to extubation).
5. Length of stay in ICU and total length of stay in hospital (time to discharge).
6. Treatment of post-op atrial fibrillation, counter-shocks (number and joules), and use of pacemakers measured according to the following schedule:
   1) From X-clamp removal to exit of O.R.
   2) First 24 hours post-op in TICU.
   3) From exit of TICU until discharge.
7. Use of inotropes and vasoconstrictors protocol driven and measured according to the following schedule:
   1) Rate of each upon leaving the O.R.
   2) Rate of each after first 24 hours post-op in TICU.

In some cases during reanimation of the heart after surgery, the heart will not respond and it fibrillates. A bolus dose of adenosine and lignocaine with or without magnesium will be given in the perfusion line or suitable entry point to the heart muscle (or intracardiac) to resuscitate the heart prior to using the defibrillator (if a defibrillator is required). If the patient has life-threatening severe arrhythmias in the intensive care ward a bolus dose of adenosine and lignocaine with or without magnesium will be given intravenously (or intracardiac) to resuscitate the heart prior to using the defibrillator (if a defibrillator is required).

Example 12

Treatment During Surgery

The compositions and methods of the invention can also be used during periods of reduced metabolic activity to reduce damage, such as cell quiescence (medically induced or otherwise). Cardiac surgery is one example. In this example, a known hyperkalemic cardioplegic is used, and the composition of the present invention is administered to reduce tissue damage during the operation.

This protocol uses miniplegia as described above, where micro amounts of the composition of the invention are mixed at various proportions with the patient's own oxygenated blood and perfused into the heart at different settings. The reference to a "setting" is a measure on the pump, such as a syringe pump, of the amount of substance being mixed in blood and delivered directly to the organ, in this example a heart.

Two cassettes were prepared as follows.

(1) The Arrest Cassette:
1. 40 mls of undiluted Potassium having 80 mEq—thus, 2 mEq/ml
2. High Setting: 25 mEq's per liter
3. Low Setting: 10 mEq's per liter The potassium in item 1 above was the primary cardioplegic agent. High potassium is the most well known and used cardioplegic, despite its known disadvantages and deleterious side-effects. An alternative cardioplegic is disclosed in WO 00/56145 (GP Dobson) comprising a potassium channel opener/agonist and/or an adenosine receptor agonist (eg. adenosine) together with a local anaesthetic (eg. lignocaine) in mM amounts. The contents of this specification are incorporated herein by reference in entirety. Although not exemplified here, the high potassium cardioplegic of item 1 above could be replaced by such a cardioplegic.

(2) The Additive Cassette:
1. 4 ml Adenosine having 12 mg—thus, 3 mg/ml
2. 10 mls Magnesium Sulfate=5 g (or a vial of $MgSO_4$ to equal 5 g)
3. 30 mls—whatever crystalloid prime is in a pump can be used (e.g. L/R, Plasmalyte™, Normosol™)
4. Total Volume in Additive Cassette: 44 mls
5. Additive Setting: 10 mls per liter This cassette is suitable for machines which support 50 ml cassettes.

Lignocaine is added to this cassette as described below to deliver the improved results. Lignocaine is added at a concentration of 0.1 to 10 times that of adenosine, preferably 0.5 to 2 times.

The data below is from experiments where no lignocaine was added to this cassette until the recovery phase shortly before cross-clamp removal. However, in another embodiment of the invention, lignocaine is added to this cassette from its first use so that a combination of adenosine and lignocaine is administered during the maintenance or quiescent phase of a procedure. It is found that this further improves the prospects of heart recovery and/or reduced postoperative complications.

The procedure used to administer the composition in this example was as follows, with an overall objective of creating aerobic arrest, not ischemic arrest.
1. Upon heparinization, fill the ice reservoir to the top with ice. Reservoir need not be filled again unless x-clamp time exceeds 3 hours. Delivery temp will be about 12° C. Towards the last third of the x-clamp period, some metabolism of oxygen rich blood should occur.
2. Temperature setting is for warm induction: Warm (37° C.)
3. High setting for arrest: 25 mEq/liter of the hyperkalemic Arrest cassette induces a rapid arrest
4. Setting for Additive: 10 ml/liter before cross-clamp Upon Application of Cross-Clamp:
1. Increase flow for antegrade quickly to 500 mls then immediately back down to 320 to 350 mls/min so as to ensure closure of the aortic valve.
2. Give 700 mls warm antegrade. Once quiescence achieved, give 300 mls more and then switch to low K+ setting (ie 10 ml/liter).
3. Give 700 mls warm retrograde.
4. Switch water temp to cold. Administer cold retrograde for as long as possible. Lower arrest setting empirically the longer flow continues.
5. Lower additive setting to 2 ml/liter. Most preparation of the heart has occurred.
6. If you are doing a CABG and distals are performed first: after the first graft, hook up the graft to the pump via multi-catheter lines. The flow is then increased very slowly to achieve a pressure of 150 Torr and the flow is noted, which is useful information for the surgeon. This will accomplish several things:
   controlled mechanical device to determine patency of the graft utilizing the gold standard of pressure to flow ratio;
   surgeon has a means to check hemostasis of the anastomotic site; and
   capability to deliver antegrade to the target site and retrograde simultaneously if desired.
7. If the procedure involves work on a valve and coronaries, perform the coronaries first. This way a sick heart is provided with the nutrients it needs while the valve is being worked on.
8. Monitor K+ according to usual SOP and adjust potassium concentration to meet desired level.

When approaching the last 10 minutes of x-clamp, preparations are made for the warm shot. These include:
1 Water setting: Warm (37 degrees)
2 Arrest setting: O—to wash out the K+ and other metabolites
3 25 mg. Lignocaine is injected into Additive bag (in this embodiment being described, it has not been added earlier) to accomplish target delivery of the prophylactic antiarrhythmic composition—typically there is about 18-35 ml left in the Additive bag at this point depending on the length of time for the procedure, which provides a lignocaine concentration of about 1 mg/ml.
4 Additive setting: 15 to 18—the goal is to empty the Additive bag prior to removal of cross-clamp.

For warm shot: usually started 5 to 10 minutes prior to x-clamp removal
1 Start retrograde warm. Zero potassium, additive setting at 15. Make sure retrograde pressure is maintained at highest level (35 to 40 Torr)
2 When electrical activity begins, continue retrograde for another minute.
3 Switch to antegrade for 2 to 3 minutes (when not obscuring surgeons' vision). This will facilitate de-airing grafts, allowing the right side of the heart to be perfused and, usually, will achieve a stable heart rate.
4 Switch back to retrograde for duration of x-clamp.
5 If additive setting runs out, continue with pure warm blood through x-clamp removal.

With microplegic techniques, the more volume you give, the better the heart likes it as it is aerobic arrest. In many instances, if administered properly, the oxygen supply/demand ratio is reversed. Administration of over 1 and up to 6 liters is associated with the greatest reduction in post-operative fibrillation.

The clinical results attained with warm blood cardioplegia have suggested that earlier observations on impairment of some cell functions by hypothermia may be more relevant than previously thought. These include reduced:
1 Membrane stability
2 Ability to utilize glucose and fatty acids
3 Mitochondrial generation of adenosine tri-phosphate leading to depressed Cell membrane function
4 Activity of adenosine tri-phosphatase system, leading to impaired cell volume regulation 5 Decreased ability of the sarcoplasmic reticulum to bind calcium
6 Mitochondrial state respiration and activity of citrate synthetase
7 Control of intracellular pH
8 Activity of the sarcoplasmic reticulum with regard to calcium uptake Coupling warm induction with cold maintenance and warm shot towards the end of cross clamp provides superior results. Warm induction, especially with the addition of adenosine (a very powerful vasodilator, among other functions), opens up all the collaterals and provides the necessary conduit for arrest and additives to reach the myocyte and endothelium. With cold induction comes constriction and the inability to globally distribute cardioplegia down to the myocyte and endothelium.

Cold maintenance provides a reduction in metabolic uptake with the slow increase in temperature occurring during the natural course of cross clamp due to ice melting. Average temperature will drift to around 12 to 14° C. The warm shot at the end is a most important aspect of myocardial protection. By allowing the heart to experience warm blood (32 to 37° C.) as long as is possible, can mean the difference in regaining most of the heart's functional recovery as opposed to a flaccid, lifeless heart, requiring inotropes and electrical support. There is also evidence that subjecting a cold, flaccid, non-beating heart to the trauma of high flow warm blood, such as experienced when the cross clamp is removed, sets the heart up for sure fire reperfusion injury.

Over the course of the last 30 years, surgeons and perfusionists have refined their operative techniques, allowing them to "customize" how they approach each patient's particular needs and demands. The only area that has essentially remained a "cookie cutter" approach has been myocardial protection; essentially "one size fits all". Without being bound by any particular theory or mode of action, it is believed that the method of this preferred embodiment is more sensitive to not over-hemodiluting the patient and thus results in improved outcomes.

In one experiment, 2688 patients undergoing cardiac surgery using cardioplegia were assessed at 6 different hospitals using different surgeons and their different techniques to assess for variability in this delicate environment. All patients were treated with a standard hyperkalemic cardioplegic solution to induce arrest. Of the patients, 1279 were in the group subjected to typical standard crystalloid-cardioplegic protocol ("Standard"). 1409 were subjected to a microplegia protocol (ie one using minimal amounts of cardioplegic directly administered to the heart) using the same hyperkalemic cardioplegic and with a warm ALM Additive cassette as described above, ie having a composition according to the invention. The invention is not specific or limited to this form of cardioplegia, but it forms application of the method of the invention and is discussed here to assess and illustrate the effect of the invention.

The Additive cassette was used as described above, such that during the recovery phase it contained Adenosine, Lignocaine and Magnesium (hence the label "ALM"). The method of the invention is referred to as "ALM" as a convenient abbreviation only. ALM was administered at crossclamp removal in accordance with the protocol described above.

Table 1 sets out the characteristics of the 2688 patients and Table 2 sets out the occurrence of different post-operative complications measured.

TABLE 1

Patient Groups

|  | Standard | ALM |
| --- | --- | --- |
| Number of Patients | 1279 | 1409 |
| Age (Years) | 62 ± 10 | 65.7 ± 10 |
| Weight (kg) | 89 ± 16 | 79.5 ± 16 |
| Height (cm) | 174 ± 9 | 168 ± 10 |
| Body mass index | 30 ± 5 | 29 ± 5 |
| Male (%) | 53 | 60 |
| Peripheral vascular disease (%) | 18 | 21 |
| Diabetes mellitus (%) | 36 | 35 |
| Emergency surgery (%) | 8 | 10 |
| Extra corporeal bypass time (min) | 87 ± 29 | 110 ± 37 |

In Table 2, the clinical outcomes are tabulated for the patients identified in Table 1. The third column represents the ALM proportion of patients as a percentage of the proportion of standard cardioplegia patients for each outcome (ie second column as a percentage of the first column). All of the outcomes in the left column are negative outcomes, and thus their minimisation is desired.

TABLE 2

Clinical Observations

|  | Standard | ALM | ALM as % of standard |
| --- | --- | --- | --- |
| Intra-operative inotropes (%) | 93% | 13% | (14%) |
| Intra-operative pacing (%) | 86% | 33% | (38%) |
| Intra-operative transfusions (%) | 43% | 24% | (56%) |
| Length of Stay post-op (days) | 7 | 6 | (79%) |
| Post-op atrial fib. (%) | 34% | 3% | (9%) |

It can be seen that there was a substantial reduction in complications following the above protocol, especially in post-operative atrial fibrillation and the need for intraoperative inotropes. In particular, the reductions in these negative outcomes are: 86% reduction of intraoperative inotropes; 64% reduction in intraoperative pacing; 44% reduction in intraoperative transfusions; 21% reduction in length of stay post-operative days and 91% reduction in post-operative atrial fibrillation.

Example 13

Administration of Adenosine/Lignocaine Solution Following Shock

The following Adenosine/Lignocaine (AL) solution(s) were used in this example: AL solution=200 microM Adenosine, 500 microM Lignocaine in Krebs Henseleit solution Rats were subjected to hemorrhagic shock for 2 hrs and 10 mins as described above.

Figure 1A:
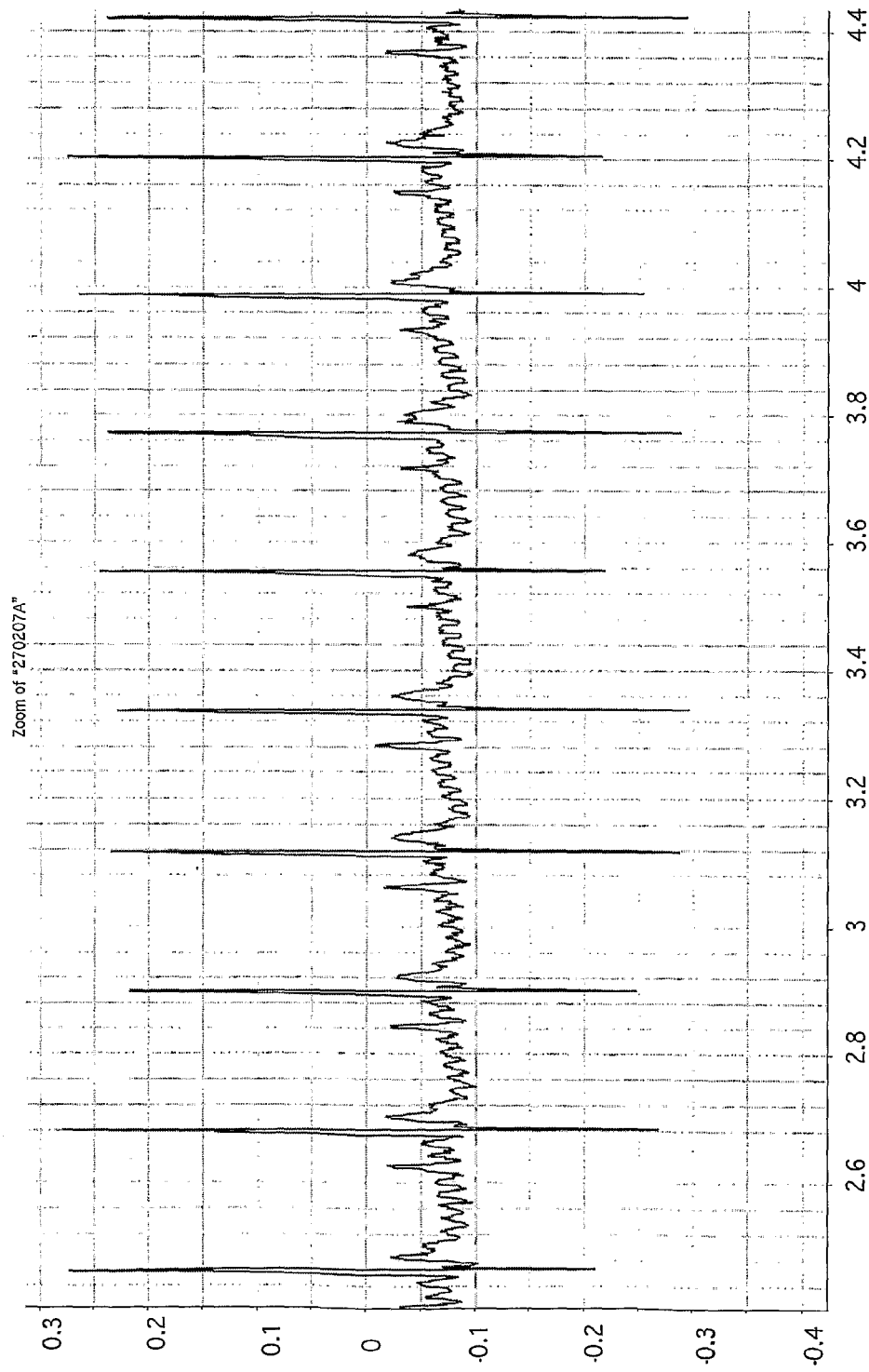
Figure 1B:
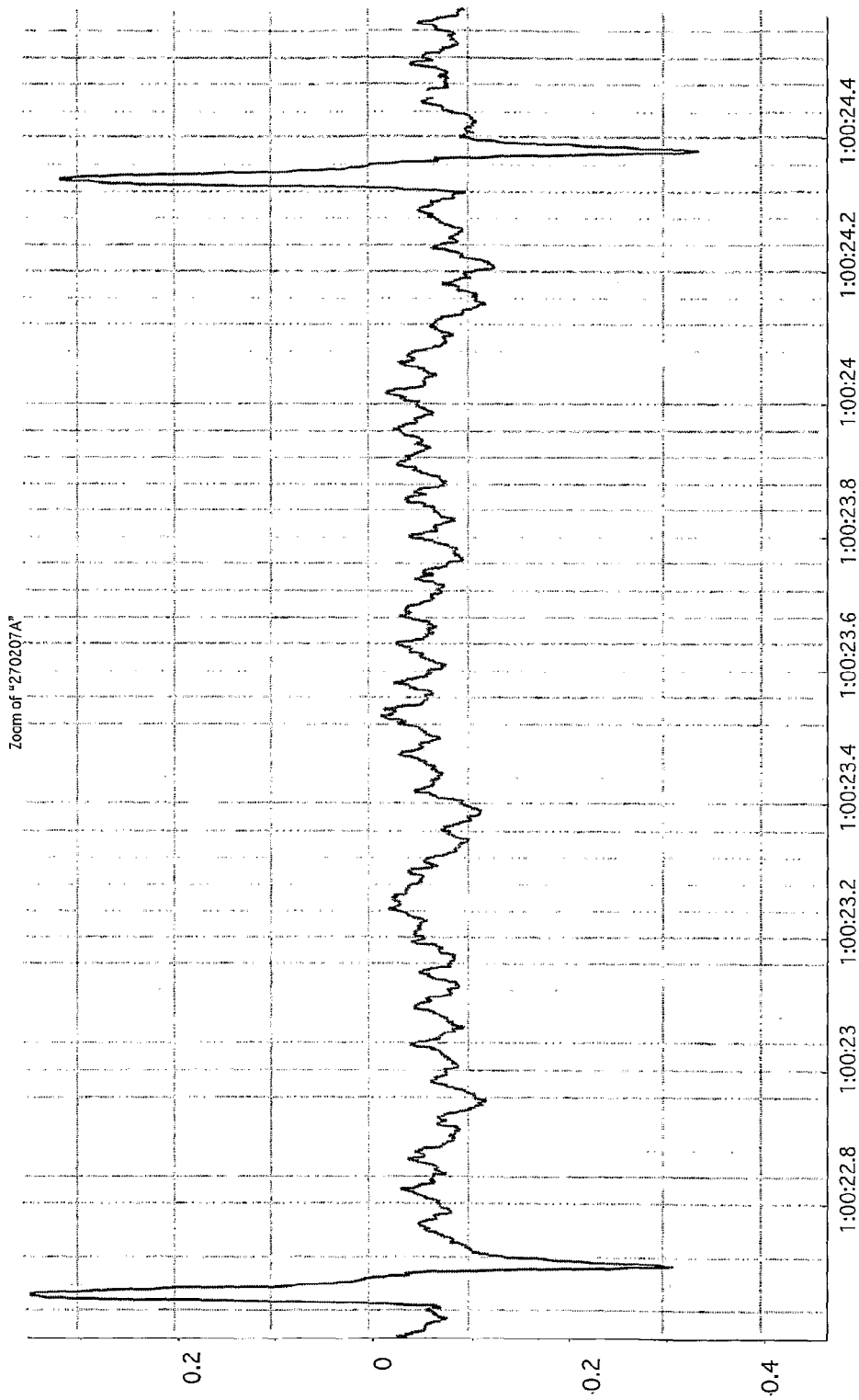
Figure 1C:
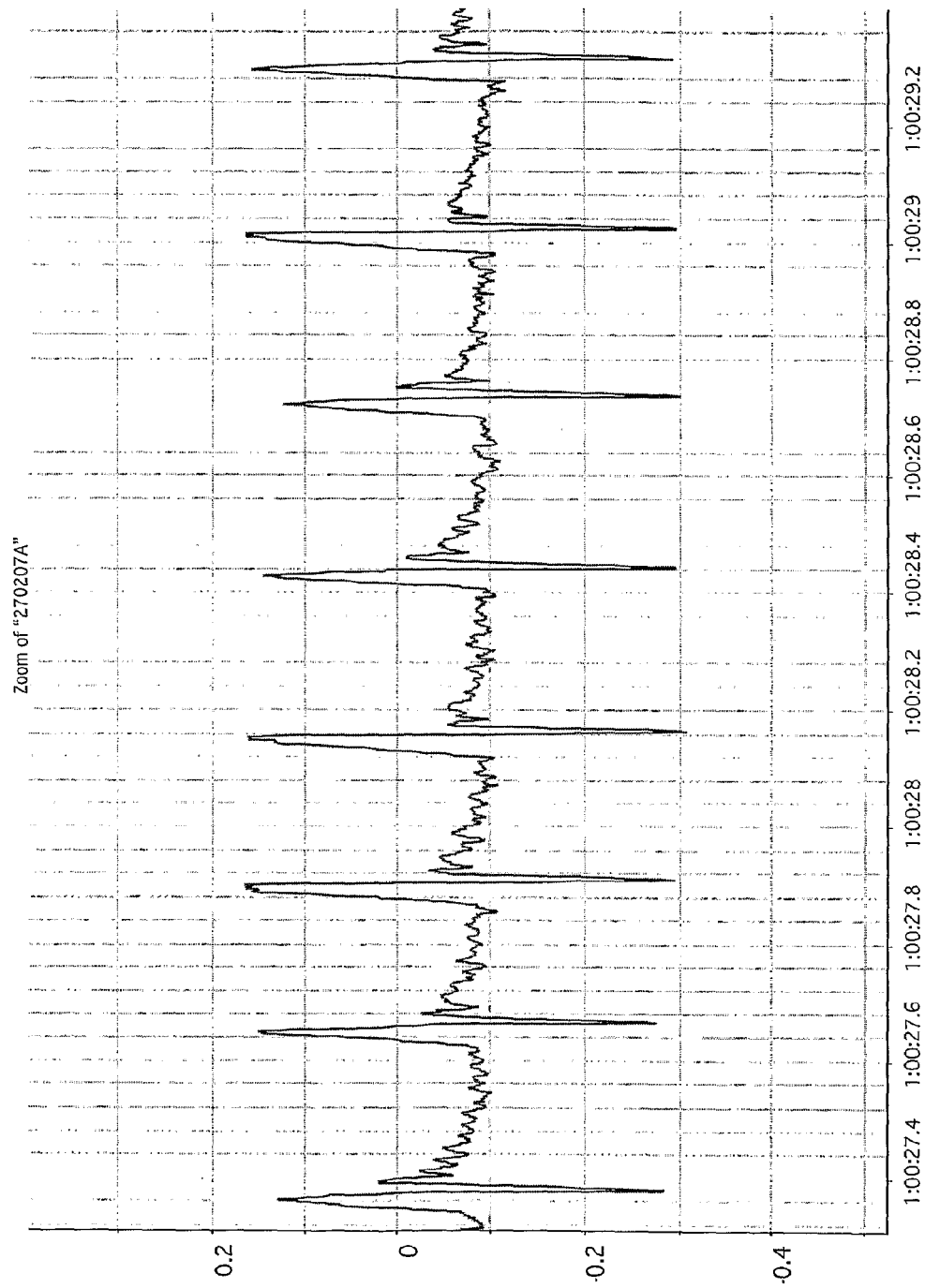

FIG. 1 shows the ECG monitoring of the rat heart during this experiment. FIG. 1A shows the rat heart as normal prior to hemorrhagic shock (Heart rate (HR)=375 bpm and MAP 114 mmHg). Following shock, the HR was reduced to 35 bpm BP<10 mmHg (FIG. 1B). 0.5 mL bolus of the AL solution was administered directly into the heart. FIG. 1C shows that the HR increased to 207 bpm 1.5 seconds following administration of the solution.

Figure 2A:
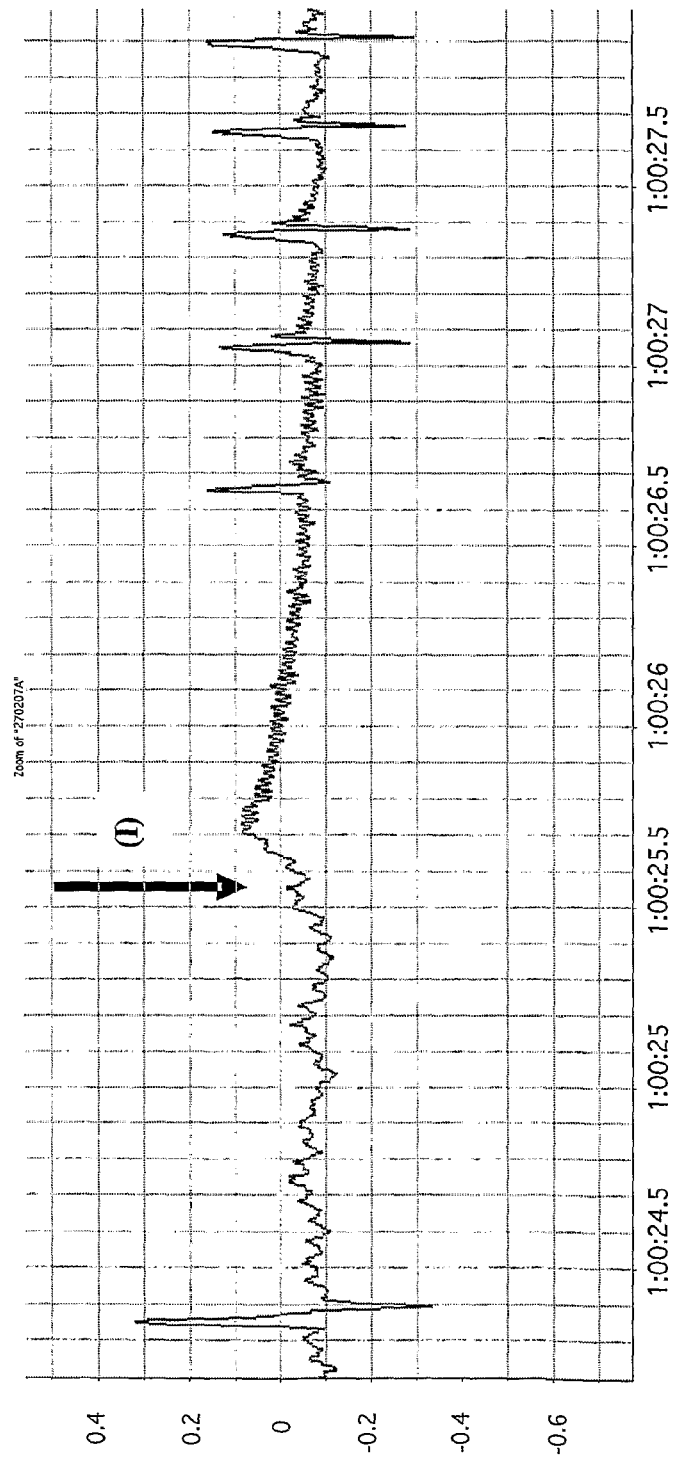
Figure 2B:
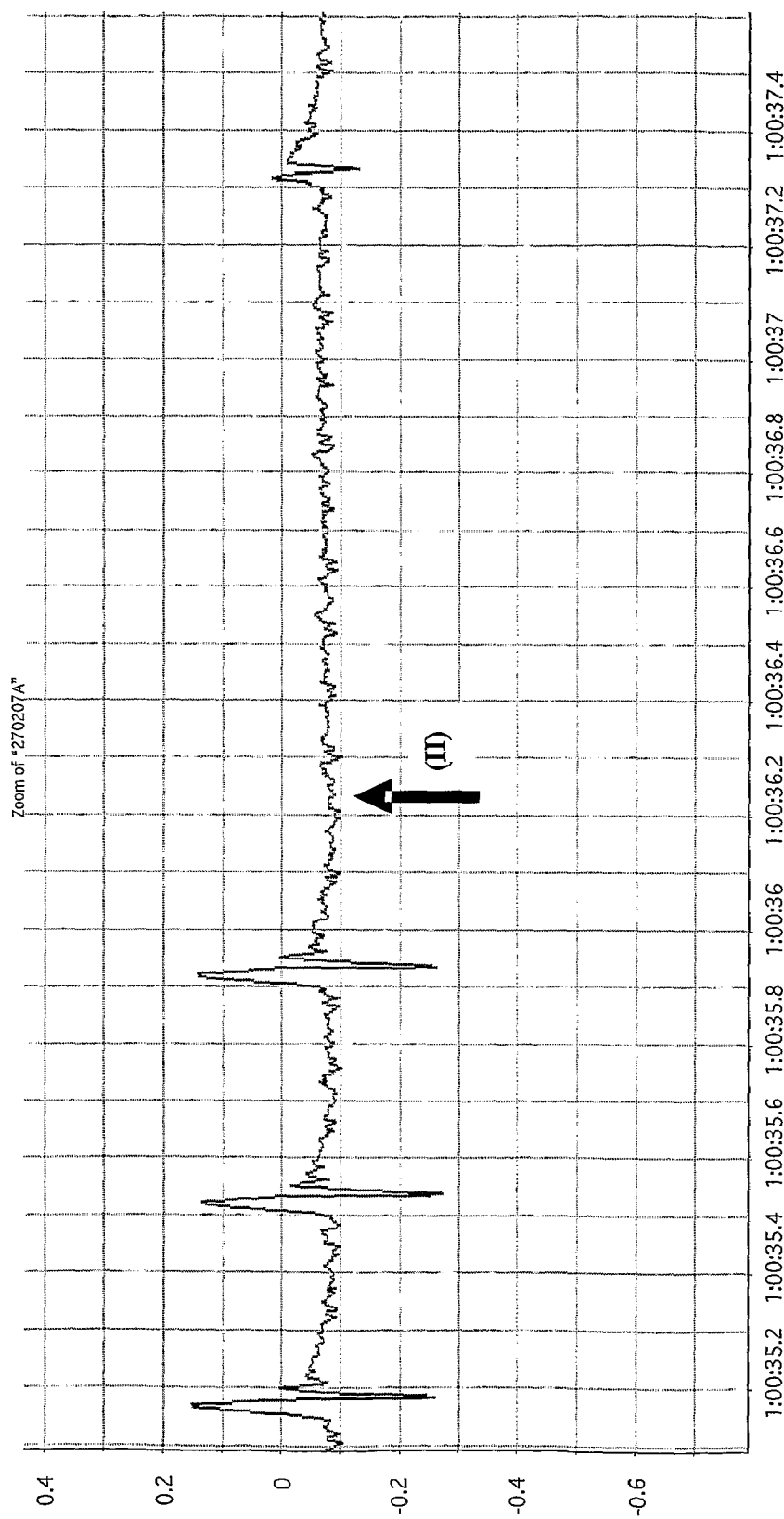

FIG. 2A shows in more detail the cardioversion of the rat heart during this experiment. In particular, 1.5 seconds following administration of the solution the rat heart rate increased from 35 bpm to 207 bpm. The point of administration of the solution is denoted as (I). FIG. 2B shows the heart rate of this rat slowing again 10 seconds after the administration of the solution.

Without being bound by any particular mode of action or theory, these results show that since the animal has very little blood volume a bolus of the AL solution can return the heart rate for an initial period. Further intervention as shown in FIG. 2B at (II), such as chest compressions and/or further shot of AL solution, would then be required to keep the subject alive, preferably with a blood volume replacement as well.

This example aims to pharmacologically induce a hypometabolic 'hibernating-like' state during resuscitation to better balance the whole body oxygen supply-demand ratio and to aggressively attenuate the inflammatory and hypercoagulable imbalances associated with traumatic hemorrhagic shock and resuscitation with particular emphasis on reducing damage to the vital organs such as brain, heart, lung and gut. The inflammatory state and edematous nature of the lung, the so-called "wet-lung", "shock lung", "Da-nang lung" or "acute respiratory distress syndrome" can occur in up to 50% of severely traumatized patients.

Example 14

Intravenous Therapy with Adenosine/Lignocaine Resuscitation Fluid Following Hemorrhagic Shock The following Adenosine/Lignocaine solution(s) were used in this example:

ALM (resuscitation solution)=10 uM Adenosine, 30 uM Lignocaine and 2.5 mM $MgSO_4$ in 7.5% NaCl solution.

Figure 3:
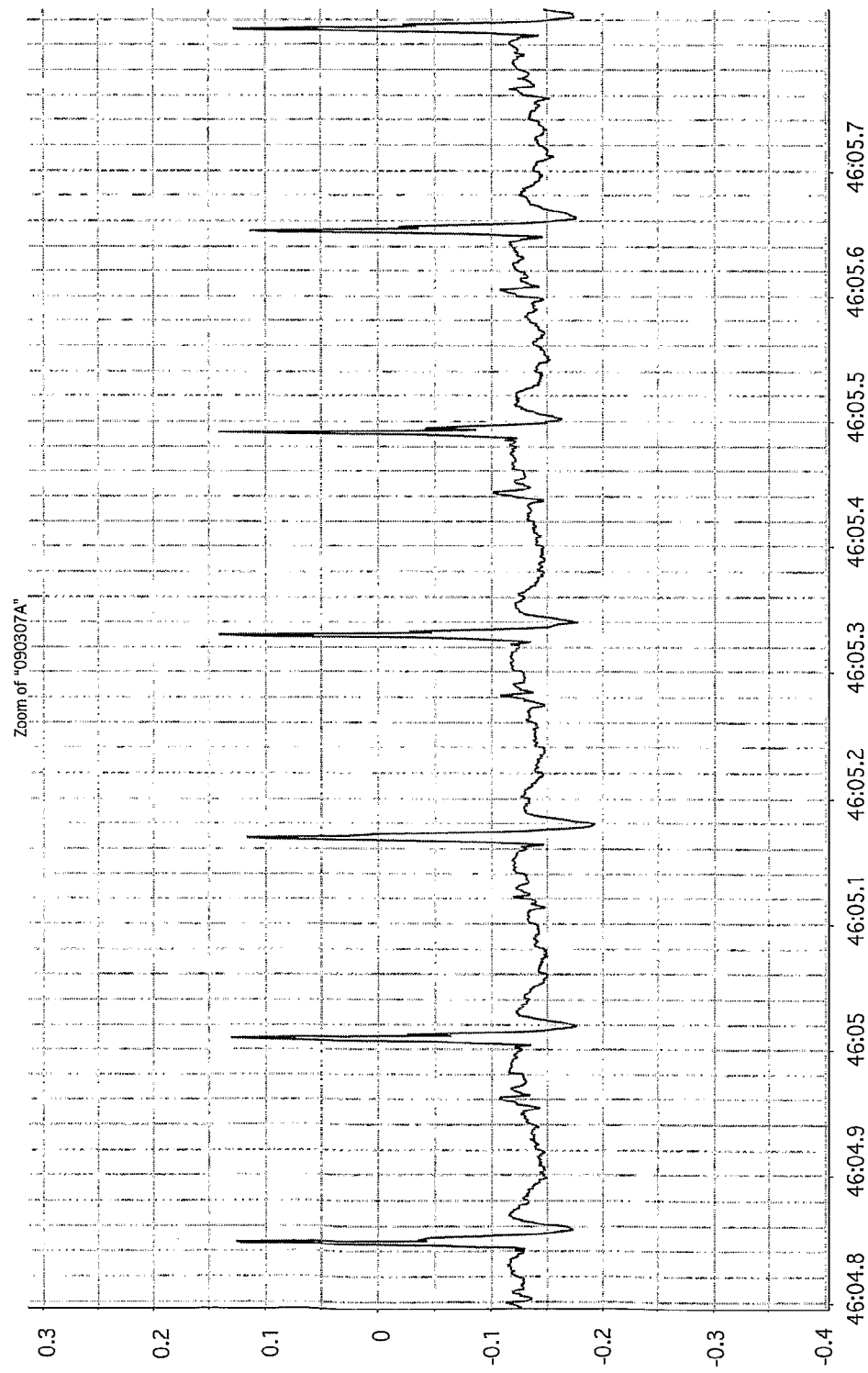
FIG. 3 shows an ECG trace of normal rat heart prior to commencement of hemorrhagic shock.

FIG. 3 shows the ECG trace of the rat during normal period. The MAP and HR measured at this time are shown in Table 3 below.

Rats were subjected to hemorrhagic shock involving approximately 45% blood loss as described above until MAP drops to around 30 to 35 mmHg. The maximum blood withdrawn was 8.6 ml over the course of the shock period.

Total blood volume estimated to be 0.06×304+0.77=19.01 ml. Therefore, % blood volume lost=8.6/19.01×100=~45%.

Figure 4:
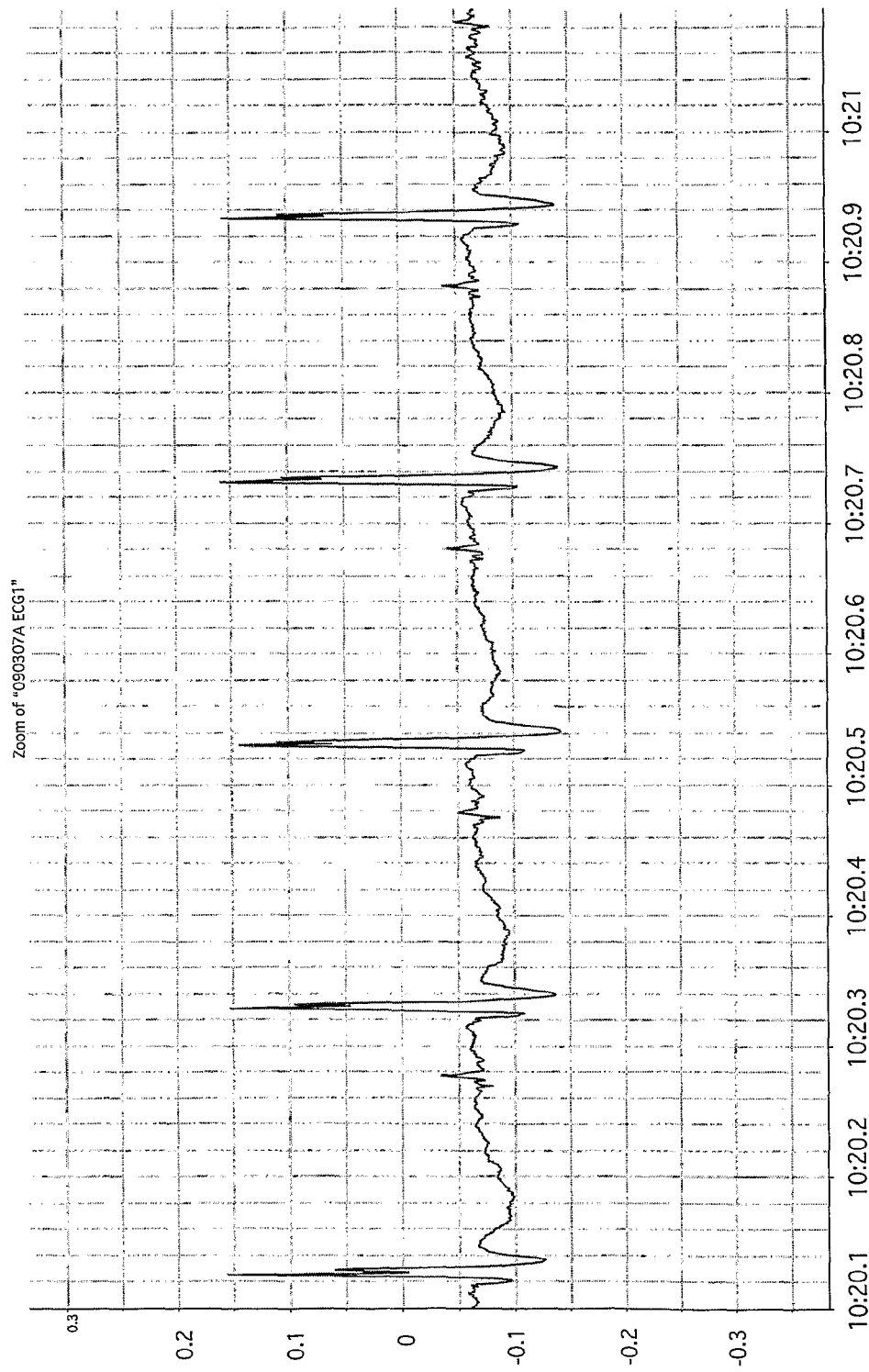
FIG. 4 shows ECG trace of rat at end of bleed period prior to commencement of "shock period"

FIG. 4 shows the ECG monitoring of the Rat heart at the end of the bleed period prior to the commencement of the "shock period". The MAP and HR measured at this time are shown in Table 3 below.

Figure 5:
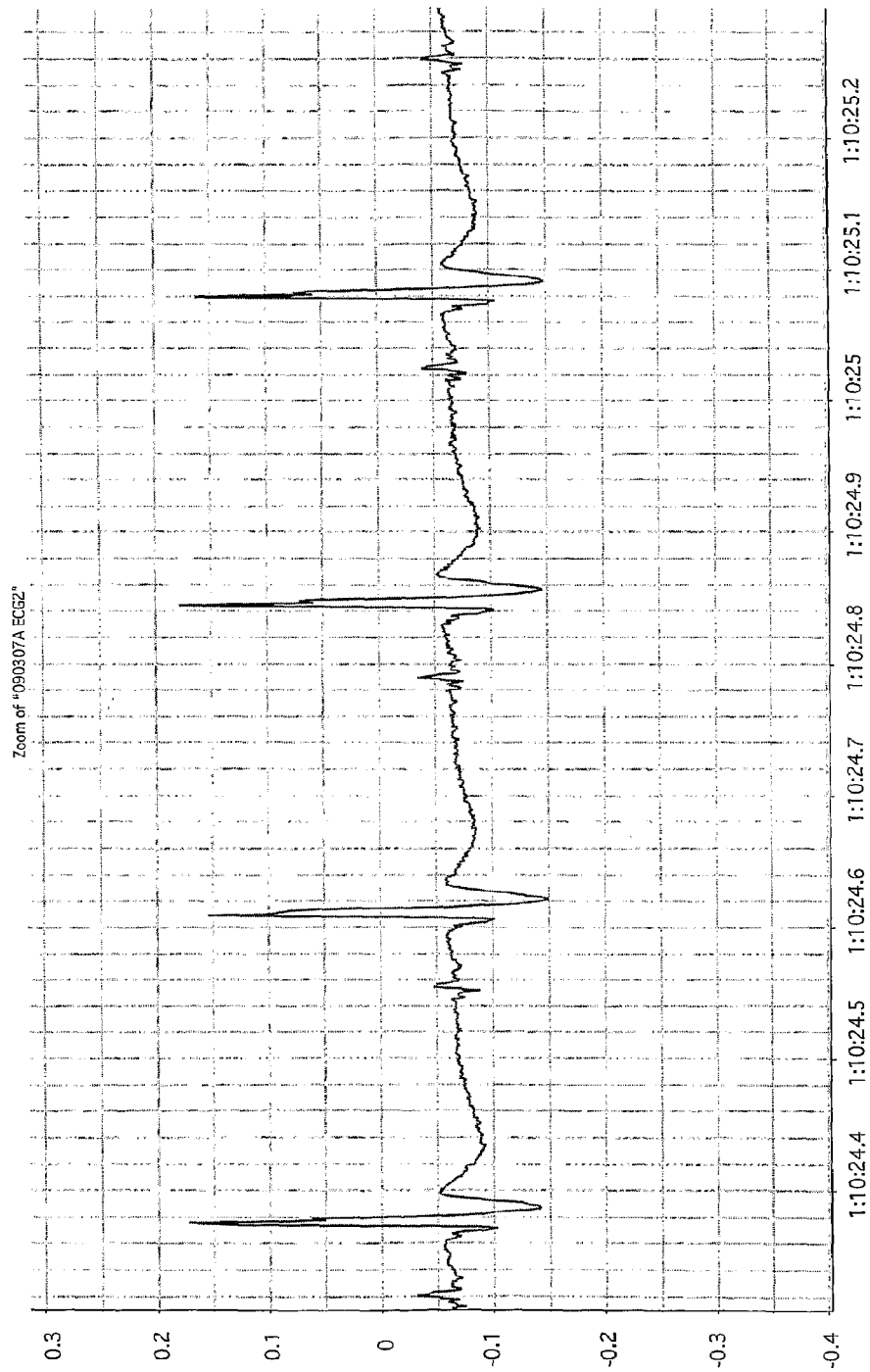
FIG. 5 shows ECG trace of rat heart at the end of first 60 mins shock period
Figure 6:
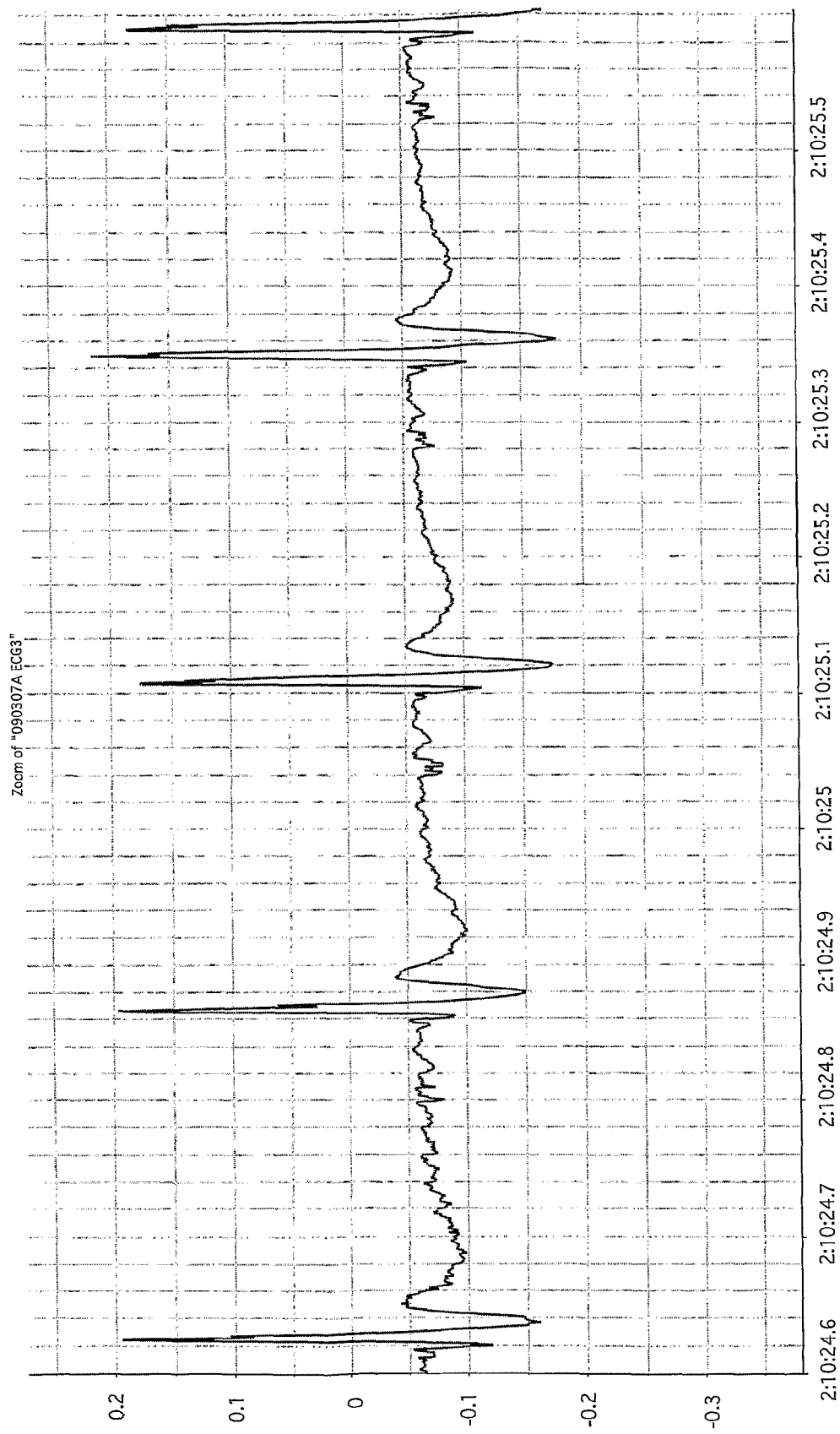
FIG. 6 shows ECG trace of rat heart at the end of 120 mins shock period
Figure 7:
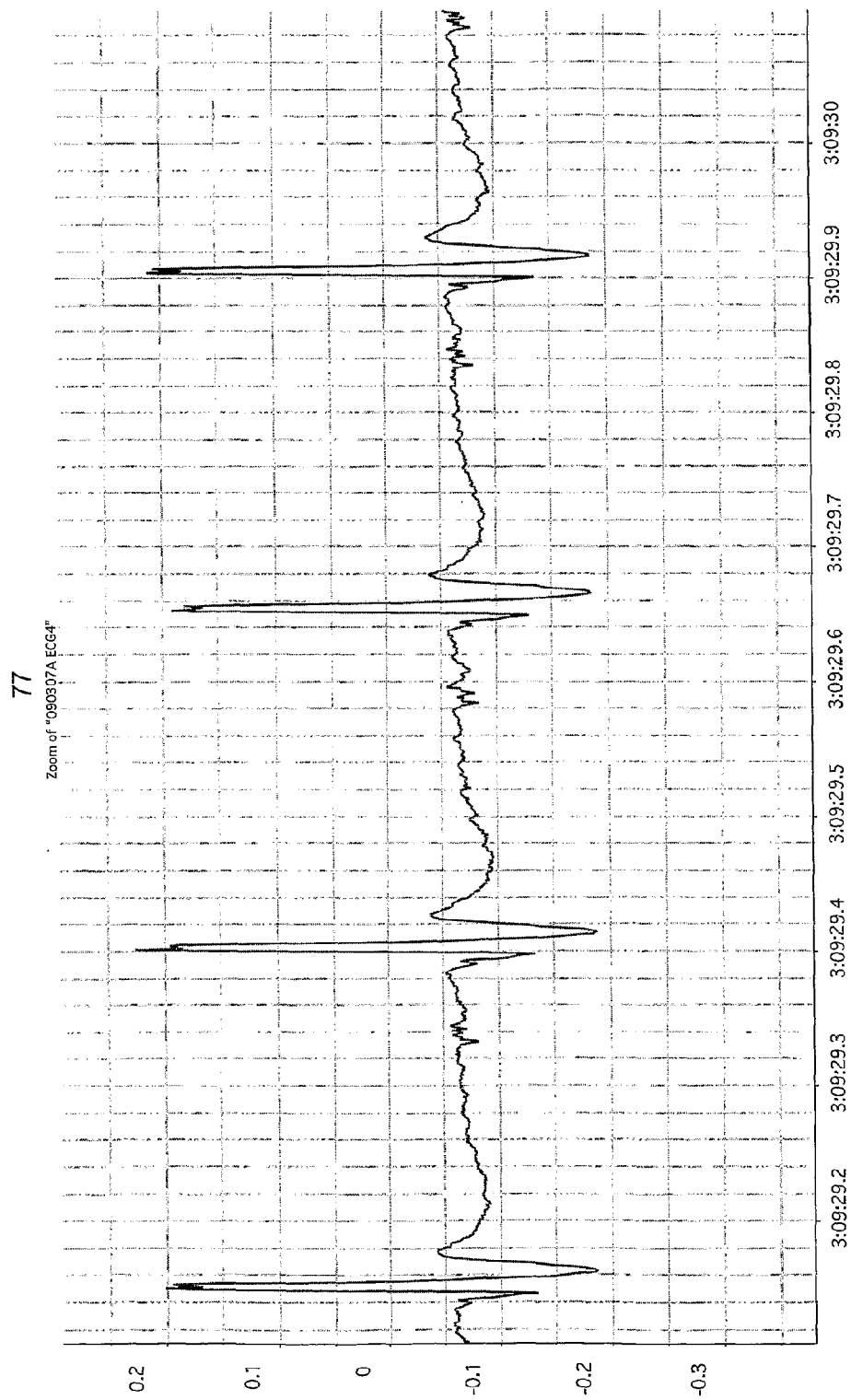
FIG. 7 shows an ECG trace of rat heart at the end of 3 hour shock period

The animal was kept in shock for 180 mins then either ALM or 7.5% saline is administered via iv bolus. The HR and MAP were measured during each 60 mins shock period, ie (I) 0-60 mins, (ii) 60-120 mins, (iii) 120-180 mins, and shown in Table 3 below. The ECG monitoring was continued (FIG. 5, FIG. 6 and FIG. 7).

At the end of the 3 hr shock period 1.0 ml bolus ALM (7.5% NaCl, 2.5 mM $MgSO_4$, 10 uM Adenosine, 30 uM Lidocaine) was infused slowly into the femoral vein.

ECG trace 10 mins after infusion is shown in FIG. 8. The HR and MAP measurements taken at this time are shown in Table 3 below.

ECG trace 30 mins after infusion is shown in FIG. 9. The HR and MAP measurements taken at this time are shown in Table 3 below.

ECG trace 60 mins after infusion is shown in FIG. 10. The HR and MAP measurements taken at this time are shown in Table 3 below.

ECG trace 90 mins after infusion is shown in FIG. 11. The HR and MAP measurements taken at this time are shown in Table 3 below.

TABLE 3

| | Mean systolic pressure (mmHg) | Mean diastolic pressure (mmHg) | MAP | Mean HR (bpm) |
|---|---|---|---|---|
| Normal (pre-hemorrhagic shock) | 119.69 | 89.77 | | 350 |
| Bleed Period | | | | |
| End of bleed period (pre-hemorrhagic shock) | — | — | 40 | 350 |
| Hemorrhagic shock period | | | | |
| Shock (0-60 mins)* | 66.48 | 33.01 | — | 281.58 |
| Shock (60-120 mins)* | 69.77 | 29.53 | — | 250.39 |
| Shock (120-180 mins)* | 67.41 | 28.33 | — | 245.80 |
| Shock (at 180 mins) | 65.58 | 27.46 | 40.17 | 239 |
| Recovery | | | | |
| 10 mins after ALM infusion | 91.66 | 36.62 | | 268.0 |
| 30 mins after ALM infusion | 79.59 | 28.31 | | 276.0 |
| 30-60 mins after ALM infusion* | 73.82 | 28.38 | 43.53 | 263.30 |
| 60 mins after ALM infusion | 71.35 | 28.13 | | 249 |
| 60-90 mins after ALM infusion* | 65.81 | 25.52 | | 252.96 |
| 90 mins after ALM recovery | 58.72 | 24.05 | | 228 |

*the mean values of each of the measurements taken over the indicated time period are shown Example 15

Comparative Example of Intravenous Therapy with Adenosine/Lignocaine Resuscitation Fluid and 7.5% Saline Following Hemorrhagic Shock The following Adenosine/Lignocaine solution(s) were used in this example:

ALM (resuscitation solution)=10 uM Adenosine, 30 uM Lignocaine and 2.5 mM $MgSO_4$ in 7.5% NaCl solution.

Rats were subjected to hemorrhagic shock involving approximately 45% blood loss as described in the previous example until MAP drops to around 30 to 35 mmHg.

Figure 12A:
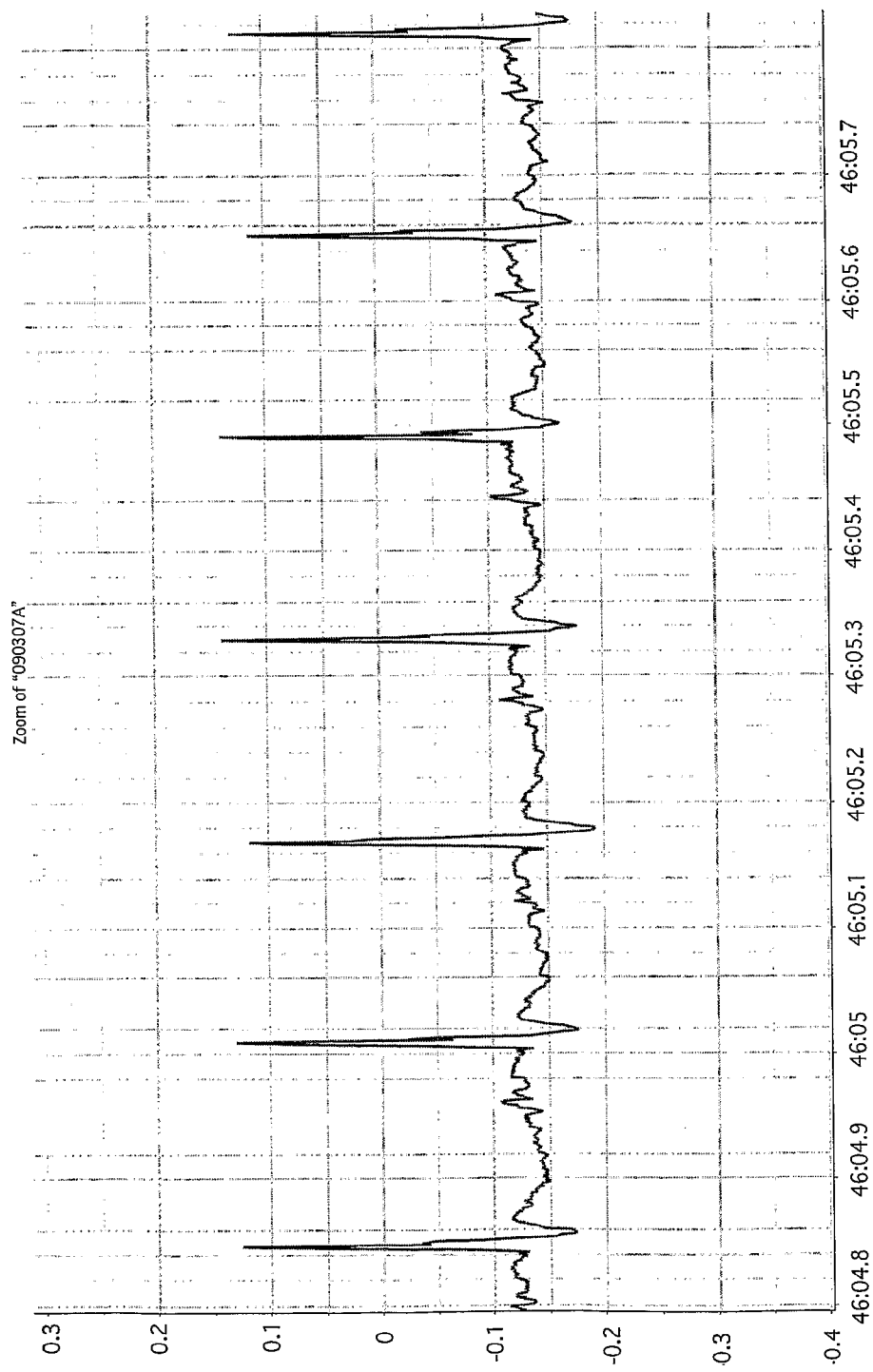
Figure 12B:
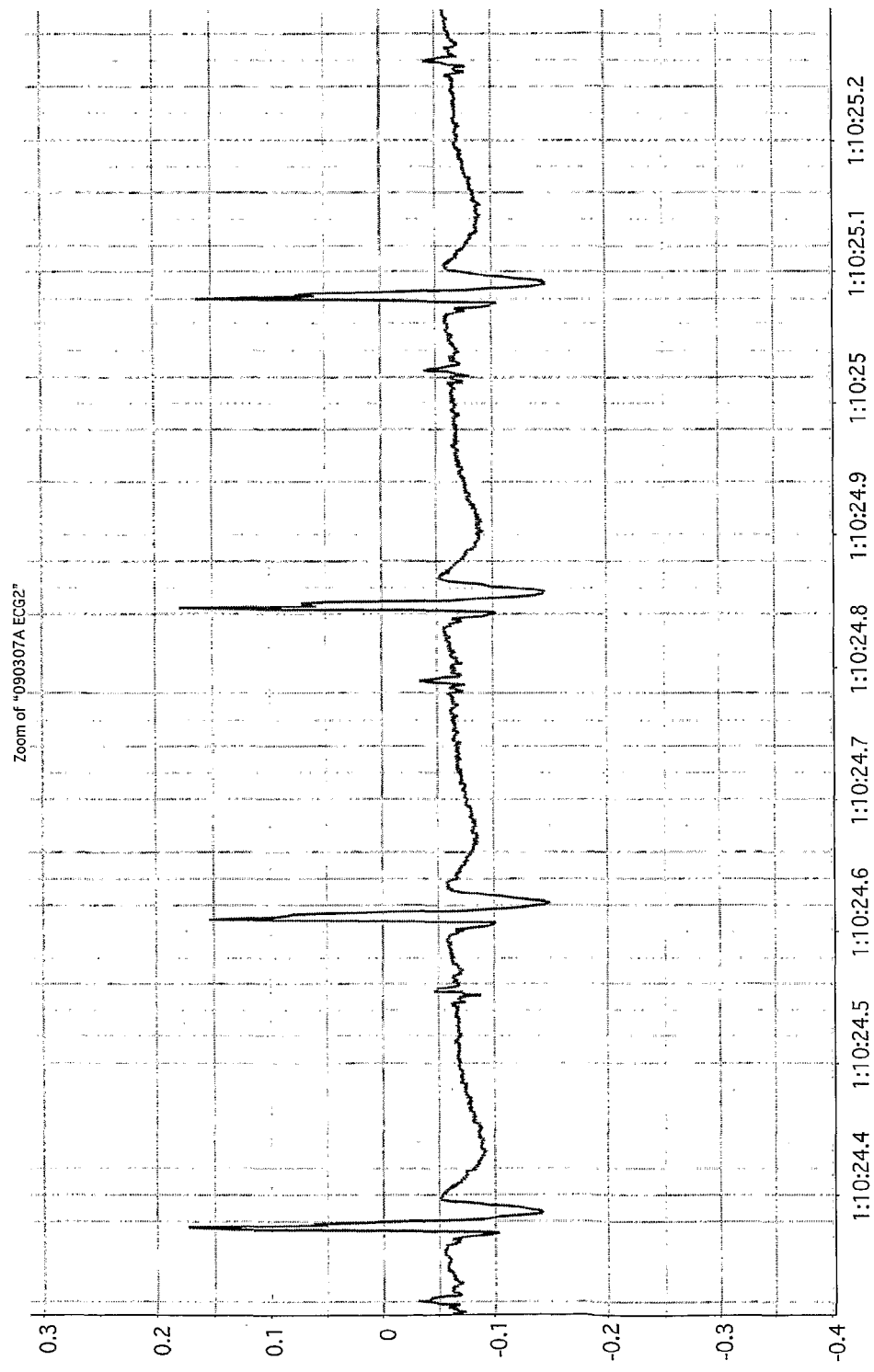
Figure 12C:
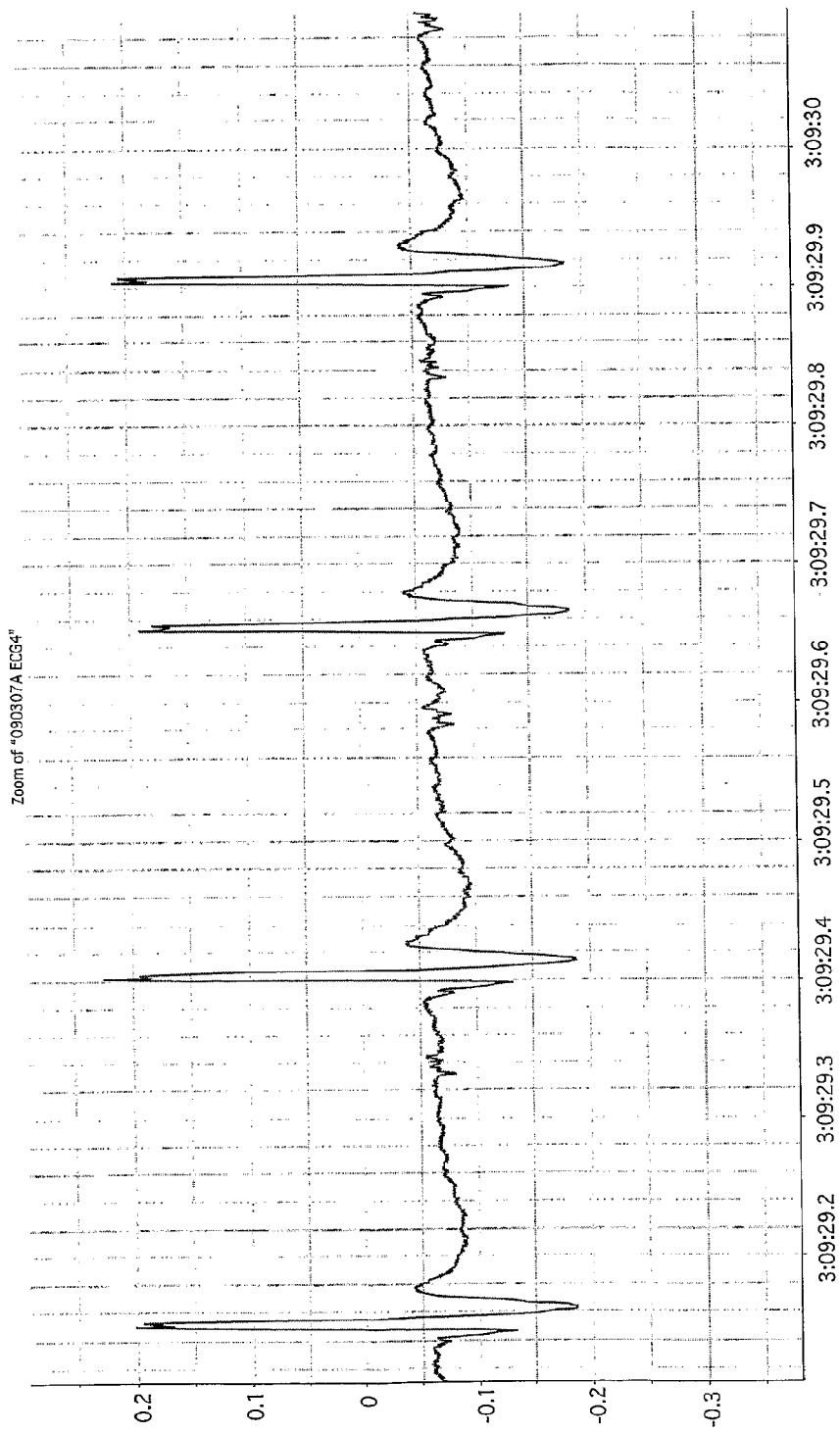

FIG. 12 shows the ECG trace of the rat during this experiment. FIG. 12A shows the rat heart as normal prior to hemorrhagic shock (HR approx 350 bpm; MAP 100 mmHg). FIG. 12B shows the ECG monitoring 60 mins after shock. The MAP and HR were measured at this time (MAP 44 mmHg; HR increased approx 280 bpm) (FIG. 12B). ECG monitoring is continued for a further 120 mins. FIG. 12C shows that the MAP remains relatively stabile after 180 mins of shock at 40 mmHg (HR approx 239 bpm).

Figure 13A:
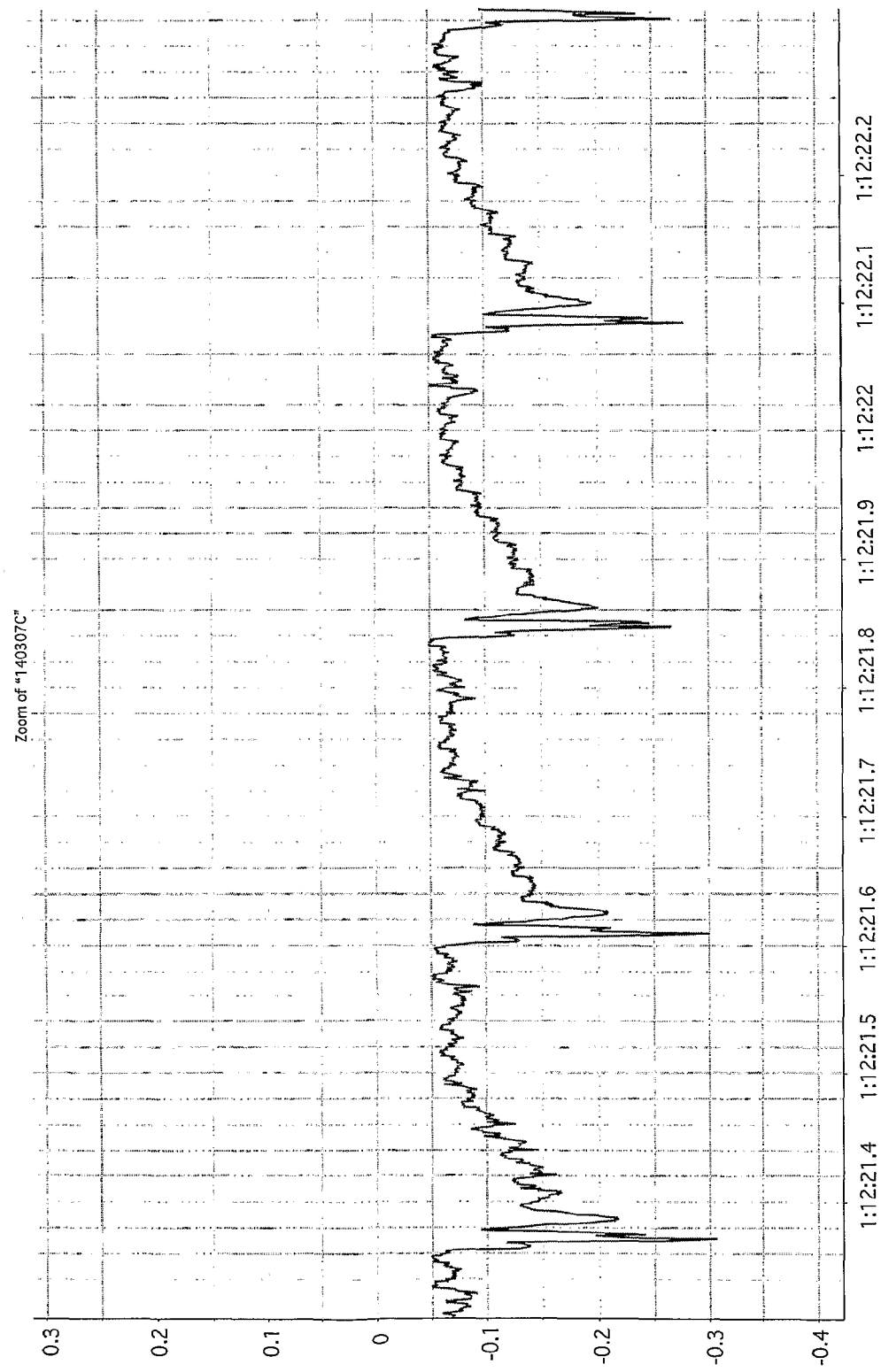
Figure 13B:
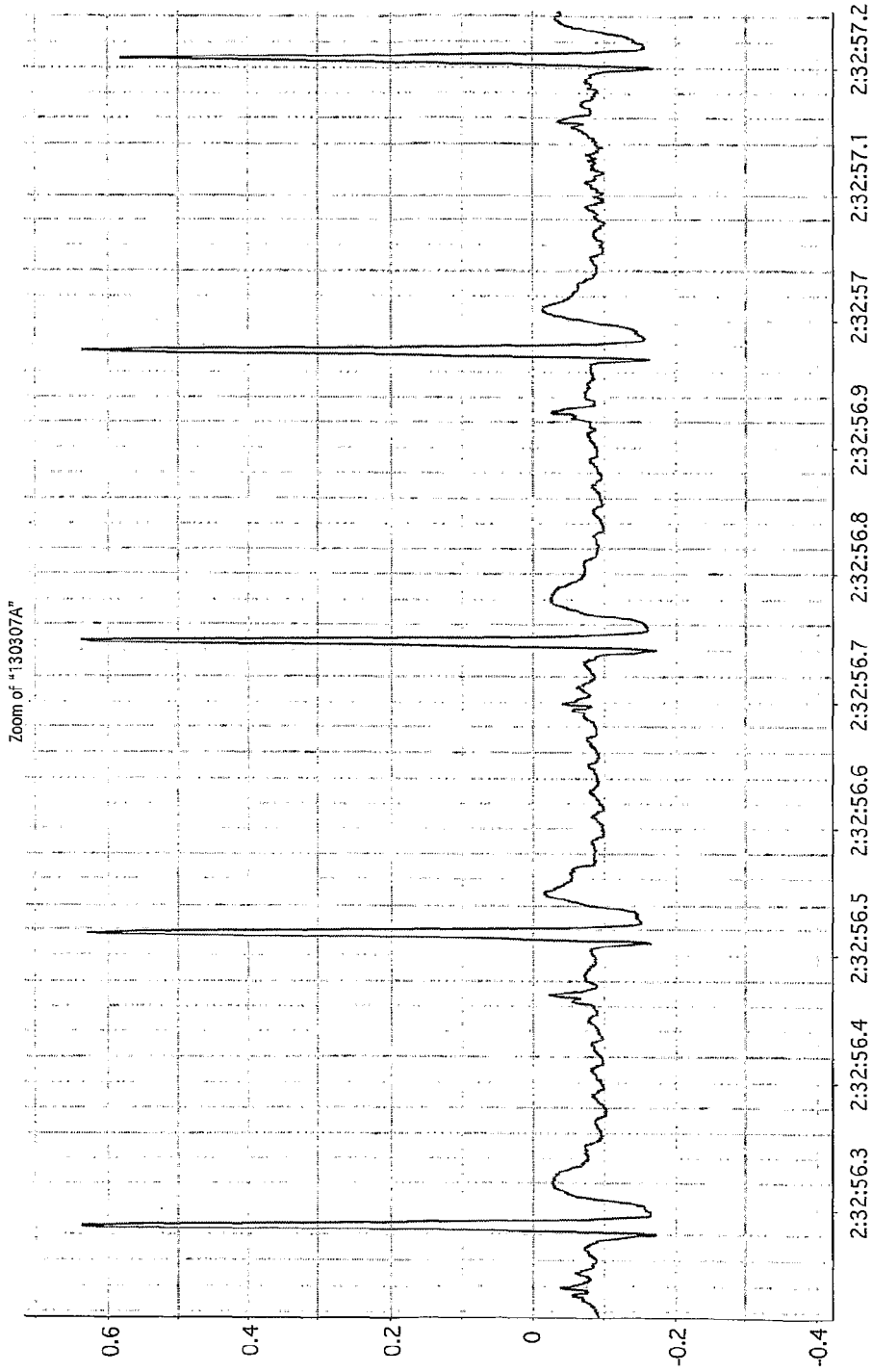

FIG. 13A shows the ECG trace of the rat following administration of 0.5 mL 7.5% saline after 180 mins shock. The HR dropped to around 39 bpm (MAP 30 mmHg). This was maintained for about 10 mins after administration of the 7.5% saline solution. The heart rate then increased to 270 bpm FIG. 13B shows the ECG trace of the rat following administration of 0.5 ml bolus of ALM after 180 mins shock. The HR increased to 261 bpm (MAP 35 mmHg) immediately.

This (and the previous example) shows that heart function can be maintained by periodic bolus administration of ALM to a subject that has suffered hemorrhagic shock. Without being bound by any particular theory or mode of action, this low volume solution could be used in situations where sufficient medical assistance is delayed. For example, the solution could be administered at periodic intervals by field medics at the site of an accident or in the battlefield to provide intraperitoneal support during complicated or prolonged evacuations or transport of the patient to a hospital. This example demonstrates that an intravenous (iv) bolus of the solution could be deployed immediately after severe blood loss to stabilize and protect the heart from ischemic depolarization and arrhythmias and to pharmacological down-regulate the major organs of the body before resuscitation. This possible battlefield scenario assumes a military medic or combat life-saver is able to assist the wounded soldier near the scene of trauma/injury.

It will be understood that the invention disclosed and defined in this specification extends to all alternative combinations of two or more of the individual features mentioned or evident from the text or drawings. All of these different combinations constitute various alternative aspects of the invention.

The invention claimed is:

1. A method of reducing injury to cells, tissues or organs in a person suffering from hemorrhagic shock as a consequence of trauma comprising:
    administering a composition to the person following the trauma, the composition comprising:
        (i) a potassium channel opener or agonist and/or an adenosine receptor agonist; and
        (ii) a local anaesthetic,
    wherein the person is suffering injury to cells, tissues or organs resulting from the hemorrhagic shock as a consequence of the trauma and administering the composition thereby reduces the injury to cells, tissues or organs.

2. The method according to claim 1, wherein the composition is hypertonic.

3. The method according to claim 2, wherein the composition includes 7.5% saline.

4. The method according to claim 1, wherein the composition is administered as one-shot.

5. The method according to claim 1, wherein the composition is administered directly to the tissue or organ.

6. The method according to claim 1, wherein component (i) is adenosine.

7. The method according to claim 1, wherein the local anaesthetic is lignocaine.

8. The method according to claim 6, wherein the local anaesthetic is lignocaine.

9. The method according to claim 1, wherein the composition further includes divalent magnesium cations.

10. The method according to claim 9, wherein the concentration of magnesium cations is up to about 20 mM.

11. The method according to claim 1, wherein the treatment comprises the further step of subsequently administering to the person a second composition, comprising:
    (i) a potassium channel opener or agonist, or an adenosine receptor agonist; and
    (ii) a local anaesthetic.

12. The method according to claim 11, wherein the second composition is administered continuously by infusion.

13. The method of claim 1, wherein the composition includes an antioxidant.

14. The method of claim 13, wherein the antioxidant is melatonin.

15. The method of claim 1, wherein the composition includes an impermeant.

16. The method of claim 15, wherein the impermeant is insulin.

17. The method according to claim 1, wherein (i) is adenosine and (ii) is lignocaine.

18. The method according to claim 11, wherein (i) is adenosine and (ii) is lignocaine.

* * * * *